(12) United States Patent
Rohr Daniel et al.

(10) Patent No.: US 11,744,654 B2
(45) Date of Patent: Sep. 5, 2023

(54) SYSTEMS AND METHODS FOR COUPLING COMPONENTS OF A MEDICAL SYSTEM

(71) Applicant: INTUITIVE SURGICAL OPERATIONS, INC., Sunnyvale, CA (US)

(72) Inventors: Matthew D. Rohr Daniel, San Francisco, CA (US); David W. Bailey, Portola Valley, CA (US); Stephen J. Blumenkranz, Los Altos, CA (US); Christopher R. Carlson, Belmont, CA (US); Matthew D. Inouye, Foster City, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1065 days.

(21) Appl. No.: 16/479,053

(22) PCT Filed: Feb. 6, 2018

(86) PCT No.: PCT/US2018/017085
§ 371 (c)(1),
(2) Date: Jul. 18, 2019

(87) PCT Pub. No.: WO2018/145100
PCT Pub. Date: Aug. 9, 2018

(65) Prior Publication Data
US 2021/0228289 A1    Jul. 29, 2021

Related U.S. Application Data

(60) Provisional application No. 62/584,546, filed on Nov. 10, 2017, provisional application No. 62/455,262,
(Continued)

(51) Int. Cl.
*A61B 34/30* (2016.01)
*B25J 9/10* (2006.01)
(Continued)

(52) U.S. Cl.
CPC ............... *A61B 34/30* (2016.02); *B25J 9/10* (2013.01); *A61B 34/37* (2016.02);
(Continued)

(58) Field of Classification Search
None
See application file for complete search history.

(56) References Cited

U.S. PATENT DOCUMENTS 5,348,000 A * 9/1994 Teves ............... A61M 16/0666
128/207.18
5,676,133 A * 10/1997 Hickle ............... A61M 16/009
128/206.25

(Continued)

FOREIGN PATENT DOCUMENTS

| WO | WO-2011143023 A1 | 11/2011 |
|---|---|---|
| WO | WO-2014138365 A1 | 9/2014 |
| WO | WO-2016191298 A1 | 12/2016 |

OTHER PUBLICATIONS

Extended European Search Report for Application No. EP18747563.7 dated Oct. 19, 2020, 10 pages.
(Continued)

*Primary Examiner* — Vicky A Johnson
(74) *Attorney, Agent, or Firm* — HAYNES AND BOONE, LLP

(57) ABSTRACT

The systems and methods of the present disclosure are for use in a medical procedure, in which a connection mechanism is provided with a first end connected to a medical system interface at a first joint and a second end connected to an anatomic orifice device at a second joint. The anatomic
(Continued)

orifice device is fixedly coupled to a patient. A flexible portion is provided between the first and second ends, the flexible portion being able to provide flexibility in at least one degree of freedom in response to movement of the anatomic orifice device.

17 Claims, 27 Drawing Sheets

Related U.S. Application Data filed on Feb. 6, 2017, provisional application No. 62/455,255, filed on Feb. 6, 2017.

(51) Int. Cl.
*A61B 34/20* (2016.01)
*A61B 34/37* (2016.01)
*A61B 17/00* (2006.01)

(52) U.S. Cl.
CPC ............ *A61B 2017/00477* (2013.01); *A61B 2034/2051* (2016.02); *A61B 2034/2061* (2016.02)

(56) References Cited

U.S. PATENT DOCUMENTS

| | | | |
|---|---|---|---|
| 6,380,732 B1 | 4/2002 | Gilboa et al. | |
| 6,389,187 B1 | 5/2002 | Greenaway et al. | |
| 6,484,724 B1 * | 11/2002 | Sloan | A61M 16/0463 128/202.27 |
| 7,316,681 B2 | 1/2008 | Madhani et al. | |
| 7,772,541 B2 | 8/2010 | Froggatt et al. | |
| 8,800,552 B2 | 8/2014 | Burns | |
| 8,900,131 B2 | 12/2014 | Chopra et al. | |
| 9,259,274 B2 | 2/2016 | Prisco et al. | |
| 9,452,276 B2 | 9/2016 | Duindam et al. | |
| 2005/0234293 A1 | 10/2005 | Yamamoto et al. | |
| 2006/0013523 A1 | 1/2006 | Childlers et al. | |
| 2007/0181130 A1 | 8/2007 | Worley | |
| 2008/0041391 A1 | 2/2008 | Worley et al. | |
| 2009/0248040 A1 | 10/2009 | Cooper et al. | |
| 2014/0005484 A1 | 1/2014 | Charles | |
| 2015/0306323 A1 | 10/2015 | Buenafe | |
| 2016/0242631 A1 | 8/2016 | Sholev | |
| 2016/0256232 A1 | 9/2016 | Awtar et al. | |
| 2017/0007792 A1 * | 1/2017 | Nye | A61M 16/0816 |

OTHER PUBLICATIONS

International Preliminary Report on Patentability for Application No. PCT/US2018/017085, dated Aug. 15, 2019, 9 pages.

International Search Report and Written Opinion for Application No. PCT/US2018/017085, dated Jun. 26, 2018, 12 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

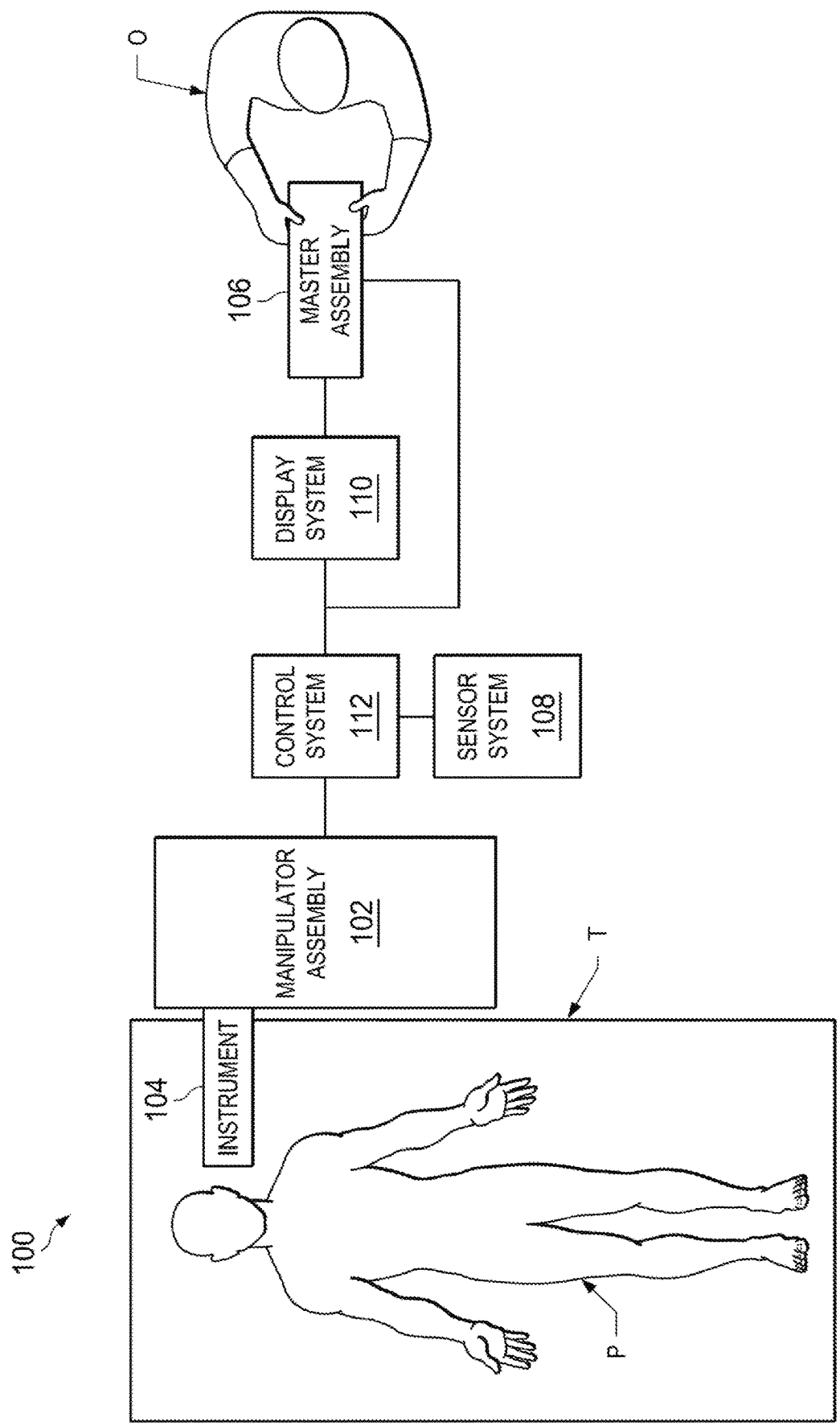

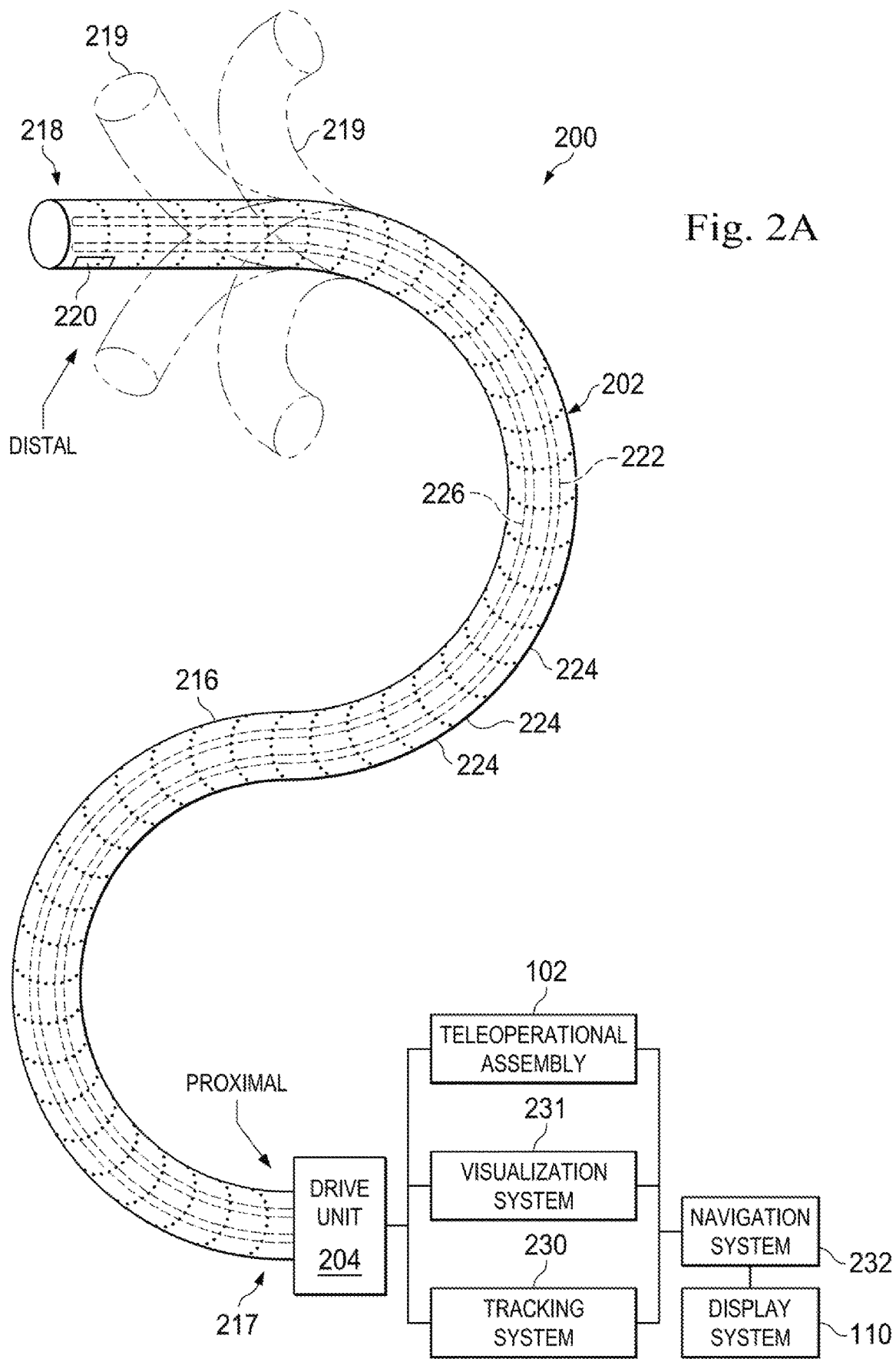

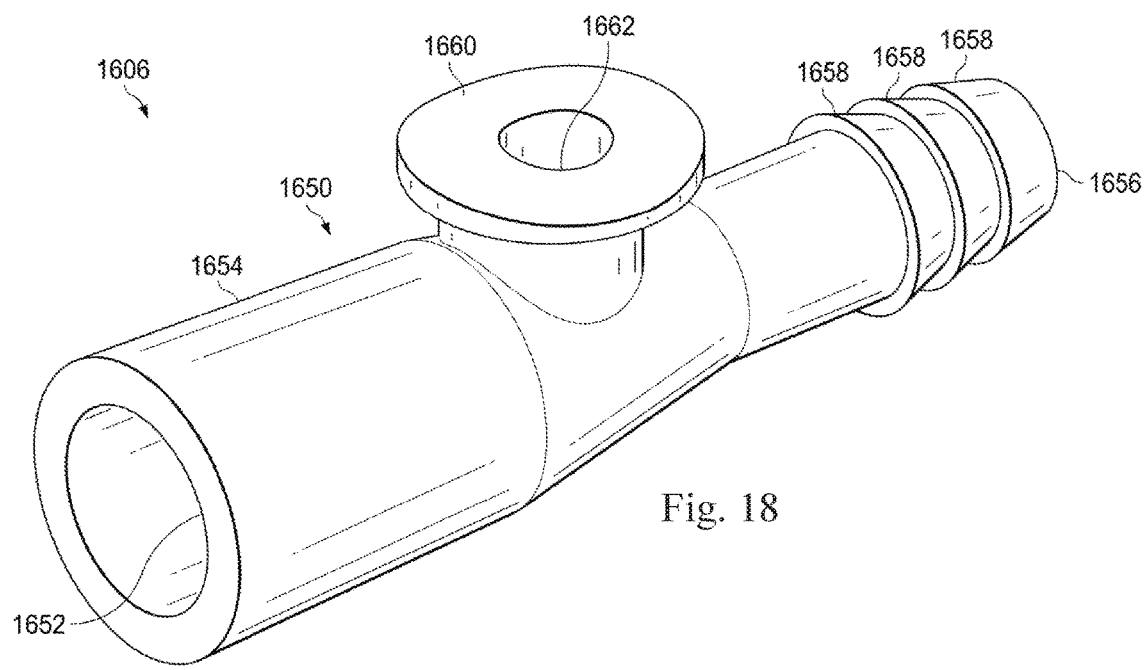
Fig. 18
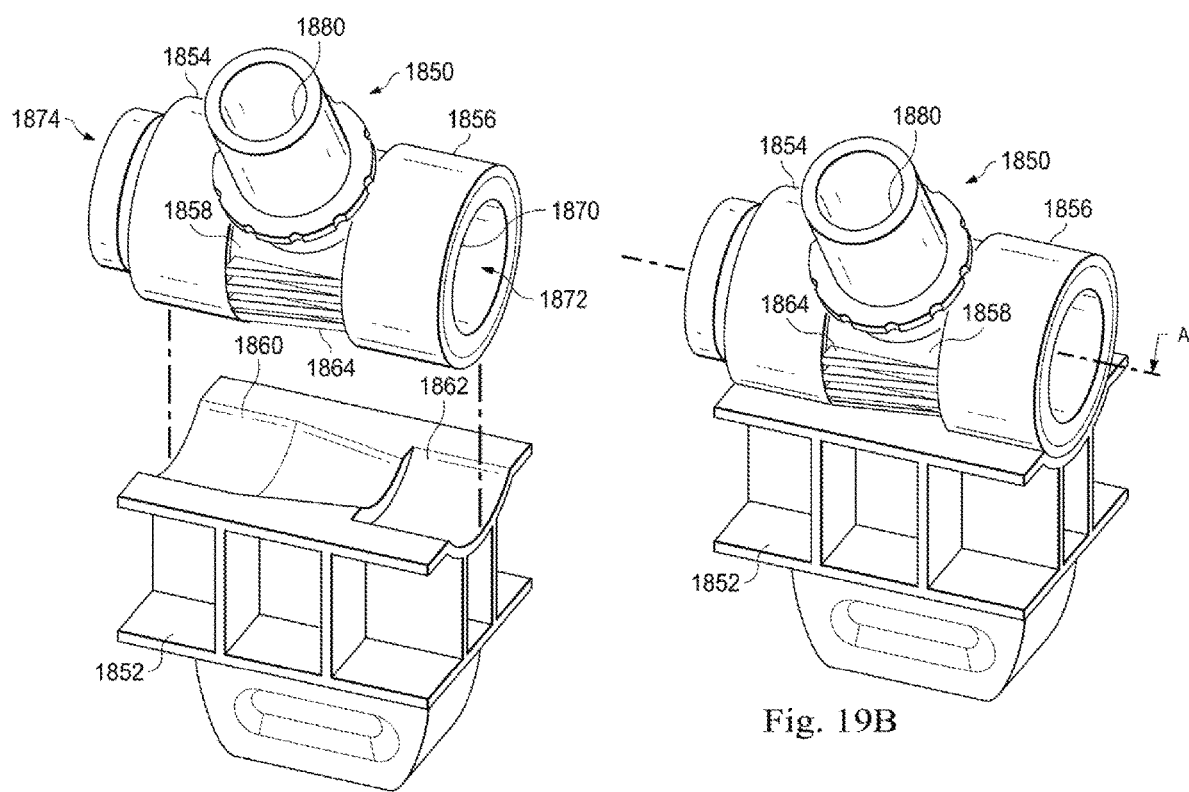
Fig. 19A
Fig. 19B

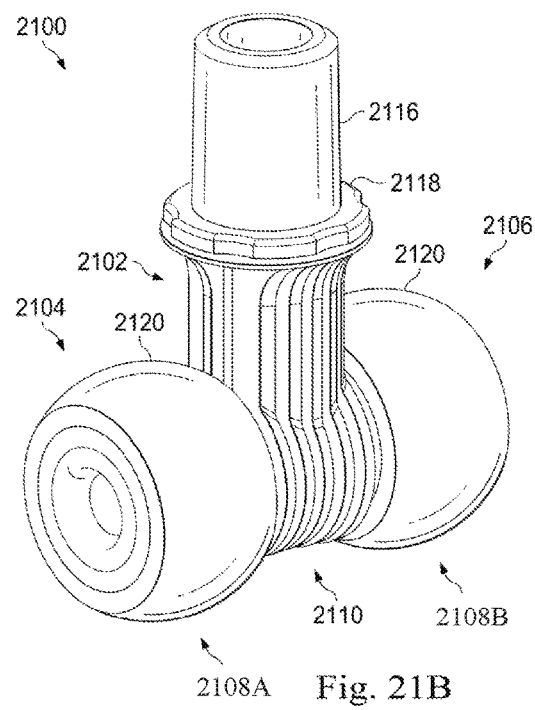
Fig. 21B
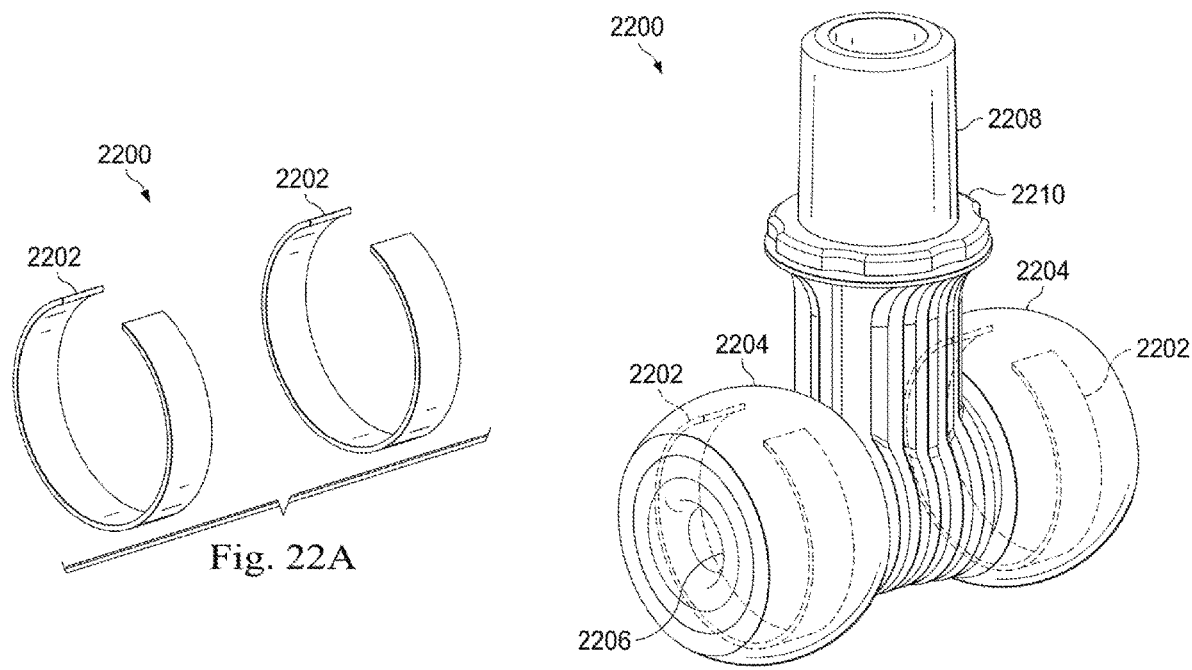
Fig. 22A
Fig. 22B

SYSTEMS AND METHODS FOR COUPLING COMPONENTS OF A MEDICAL SYSTEM

RELATED APPLICATIONS

This patent application is the U.S. national phase of International Application No. PCT/US2018/017085, filed Feb. 6, 2018, which designated the U.S. and claims priority to and the benefit of the filing date of U.S. Provisional Patent Application 62/455,255, entitled "Systems and Methods for Providing Flexible Connections Between Components of a Teleoperational Surgical Procedure," filed Feb. 6, 2017; U.S. Provisional Patent Application No. 62/455,262, entitled "Systems and Methods for Providing Flexible Connections Between Components of a Teleoperational Surgical Procedure," filed Feb. 6, 2017; and U. S. Provisional Patent Application No. 62/584,546, entitled "Systems and Methods for Coupling Components in a Minimally Invasive Medical System," filed Nov. 10, 2017, each of which is incorporated by reference herein in its entirety.

FIELD

The present disclosure is directed to systems and methods employing flexibly connected elements to provide accommodation for patient motion during a robotic medical procedure. In particular, the present disclosure is directed to providing controlled movement of flexible connections which accommodate movement between a robotic medical system and an airway management device (e.g., endotracheal tube) connected to the patient during patient movement. The present disclosure is also directed to systems and methods for providing controlled retention and release of the flexible connections during the robotic medical procedure. In particular, the present disclosure is directed to providing mechanical and electro-mechanical mechanisms that release (i.e., decouple), when necessary, the flexible connections between the robotic medical system and the airway management device. In the above exemplary ways, the present disclosure provides systems and methods to ensure safety of the patient during the robotic medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments (including surgical, diagnostic, therapeutic, or biopsy instruments to reach a target tissue location. One such minimally invasive technique is to use a flexible and/or steerable elongate device such as a flexible catheter that can be inserted into anatomic passageways and navigated towards a region of interest within the patient anatomy. Control of such an elongate device by medical personnel involves the management of several degrees of freedom including at least the management of insertion and retraction of the elongate device as well as steering of the device. In addition, different modes of operation may also be supported.

In one example, an endotracheal tube (ET tube) may be inserted through the nose or mouth of a patient and placed within the trachea. A medical instrument or device may then be inserted through the endotracheal tube and used to view the trachea and other bronchial passages and/or to conduct a biopsy and/or diagnose lung diseases and infections. The ET tube is used for airway management, for example for use during mechanical ventilation as well for prevention of damage to patient anatomy such as vocal cords during the medical procedure. A laryngeal mask airway (LMA) may also be used in place of an ET tube. Collectively, devices such as ET tubes and LMAs may be called airway management devices. Airway management devices may be one type of anatomic orifice devices that provide entryway management and support of a natural or surgically created orifice in a patient anatomy.

Conventionally, the medical instruments that are used in surgical or other medical procedures are manually controlled by an operator. During the manual procedures, the operator handles the medical instruments, the bronchial instruments, and/or diagnostic instruments by introducing them through the airway management device to perform the medical procedure. As a result, the operator is able to sense and, therefore, control parameters (e.g., force, pressure, displacement, etc.) that affect movement of the medical instrument in relation to the patient anatomy during expected motions such as breathing and also during unexpected motions such as coughing. Thus, the operator can compensate for patient movement, preventing relative movement of the medical instrument and the airway management device. However, when the procedures are robotic (e.g., teleoperational), airway management devices may be connected directly to a robotic medical system and may be fixed and stationary relative to the robotic system.

In this case, unexpected patient motion may cause the airway management devices to become displaced from the patient airway, which could result in loss of mechanical ventilation and/or damage to the patient's trachea. Thus, it would be desirable to provide a connection between the airway management device and the robotic medical system that ensures patient safety during the medical procedure.

SUMMARY

The embodiments of the invention are best summarized by the claims that follow the description.

Consistent with some embodiments, systems and methods of the present disclosure are for use in a robotic medical procedure. In one such embodiment, an apparatus for movably coupling a robotic medical system to an anatomic orifice device includes a first end portion configured to be connected to the robotic medical system and a second end portion configured to be connected to the anatomic orifice device. The anatomic orifice device is fixedly coupled to a patient. The apparatus further includes a medial portion between the first end portion and the second end portion that is configured to accommodate motion between the robotic medical system and the anatomic orifice device in at least one degree of freedom.

Consistent with some embodiments, systems and methods of the present disclosure are for use in a robotic medical procedure. In one such embodiment, an apparatus for movably coupling a robotic medical instrument system to an anatomic orifice device includes a hollow medial portion having a first end, a second end, and a passageway therebetween, and a coupling member coupled to the medial portion along a longitudinal axis of the medial portion, such that the passageway extends through the coupling member. The coupling member is comprised of a curved surface configured to rotatably connect the anatomic orifice device to the robotic medical system.

Consistent with some embodiments, systems and methods of the present disclosure are for use in a robotic medical procedure. In one such embodiment, an apparatus includes a connection mechanism that includes a first connector portion configured for attachment to a robotic medical system and a second connector portion configured for attachment to an anatomic orifice device coupled to a patient. The first connector portion is connected to the second connector portion. The apparatus further includes a sensing mechanism configured to sense a parameter associated with the patient relative to the robotic medical system, and the first connector portion is configured to be disconnected from the second connector portion based on the sensed parameter.

Consistent with some embodiments, systems and methods of the present disclosure are for use in a robotic medical procedure. In one such embodiment, a method for use of a medical apparatus comprising first and second connector portions includes attaching the first connector portion to a robotic medical system, and attaching the second connector portion to an anatomic orifice device. The anatomic orifice device is coupled to a patient. The first connector portion is connected to the second connector portion, a parameter associated with the patient relative to the robotic medical system is sensed, and the first connector portion is disconnected from the second connector portion based on the sensed parameter.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIGS. 6A-D illustrate various aspects of a connection mechanism according to an embodiment of the present disclosure.

FIGS. 7A-D illustrate various aspects of a connection mechanism according to an embodiment of the present disclosure.

FIGS. 8A-D illustrate various aspects of a connection mechanism according to an embodiment of the present disclosure.

FIGS. 9A-D illustrate various aspects of a kinematic connection mechanism according to an embodiment of the present disclosure.

FIGS. 10A-D illustrate various aspects of a kinematic connection mechanism according to an embodiment of the present disclosure.

Figure 11:
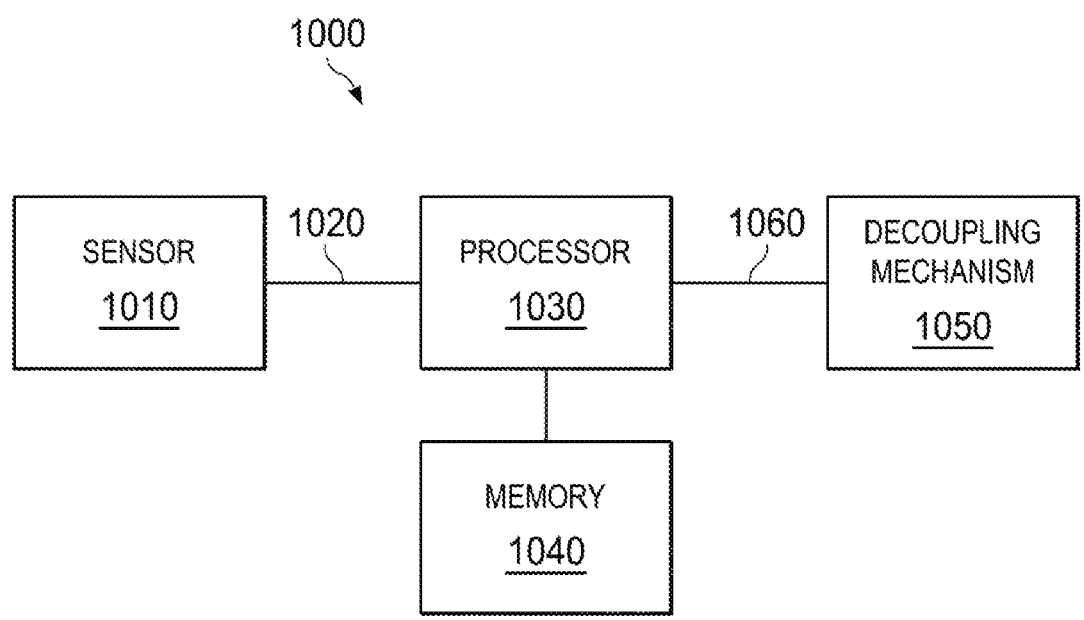

FIG. 11 illustrates a block diagram of a sensing mechanism according to an embodiment of the present disclosure.

Figure 12A:
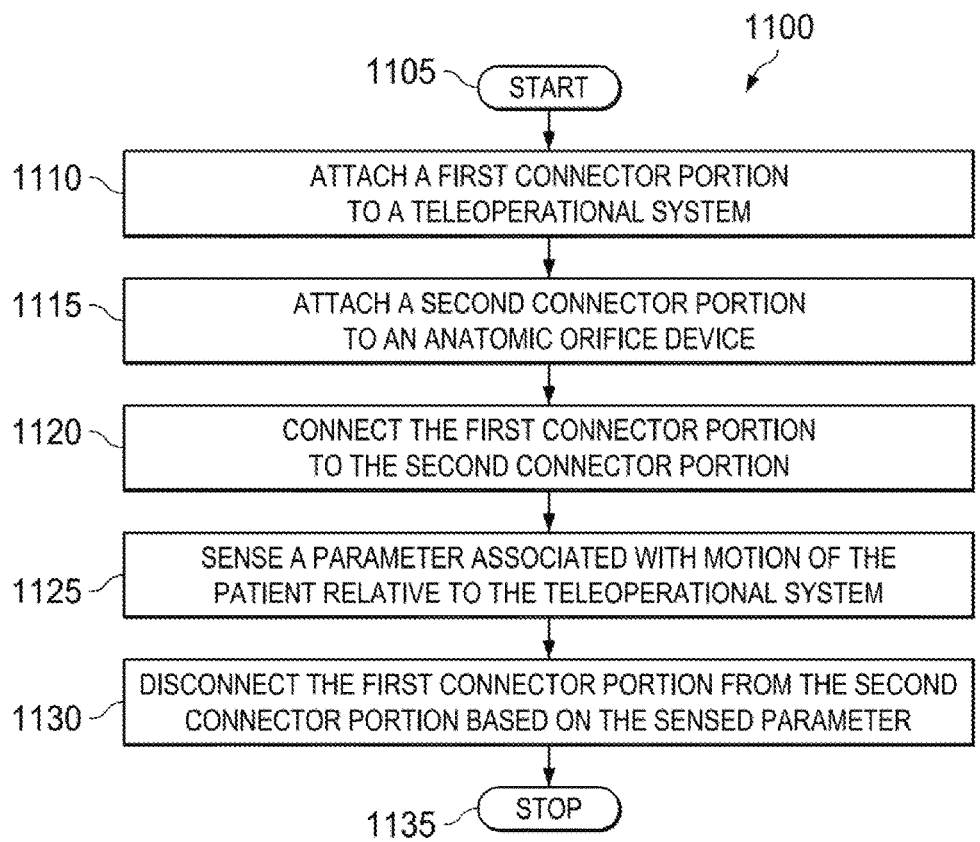

FIG. 12A illustrates a method according to an embodiment of the present disclosure.

Figure 12B:
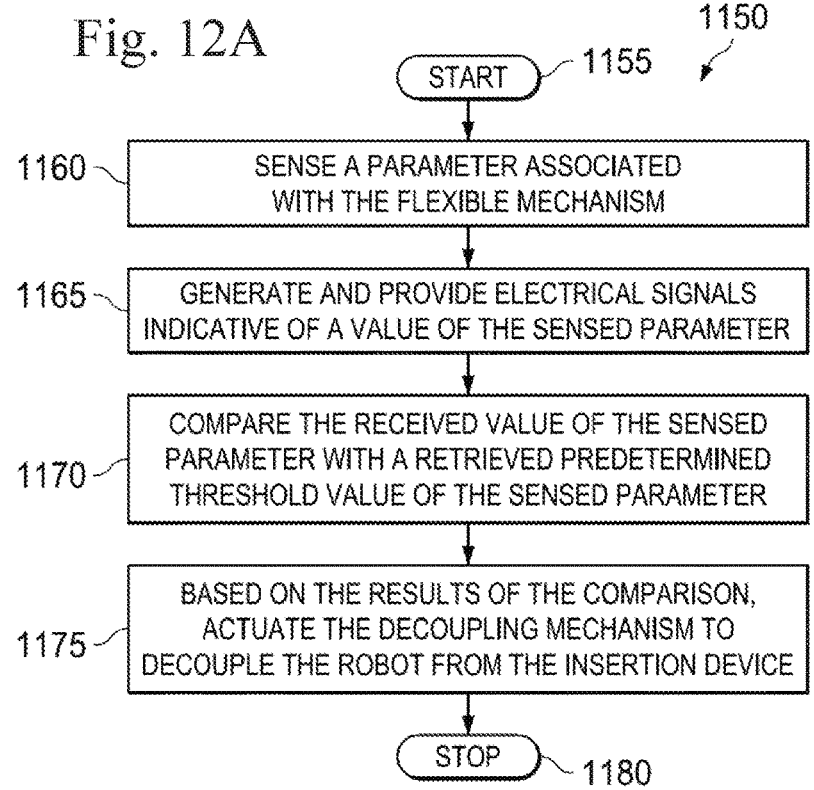

FIG. 12B illustrates a method performed by the sensing mechanism according to an embodiment of the present disclosure.

Figure 13:
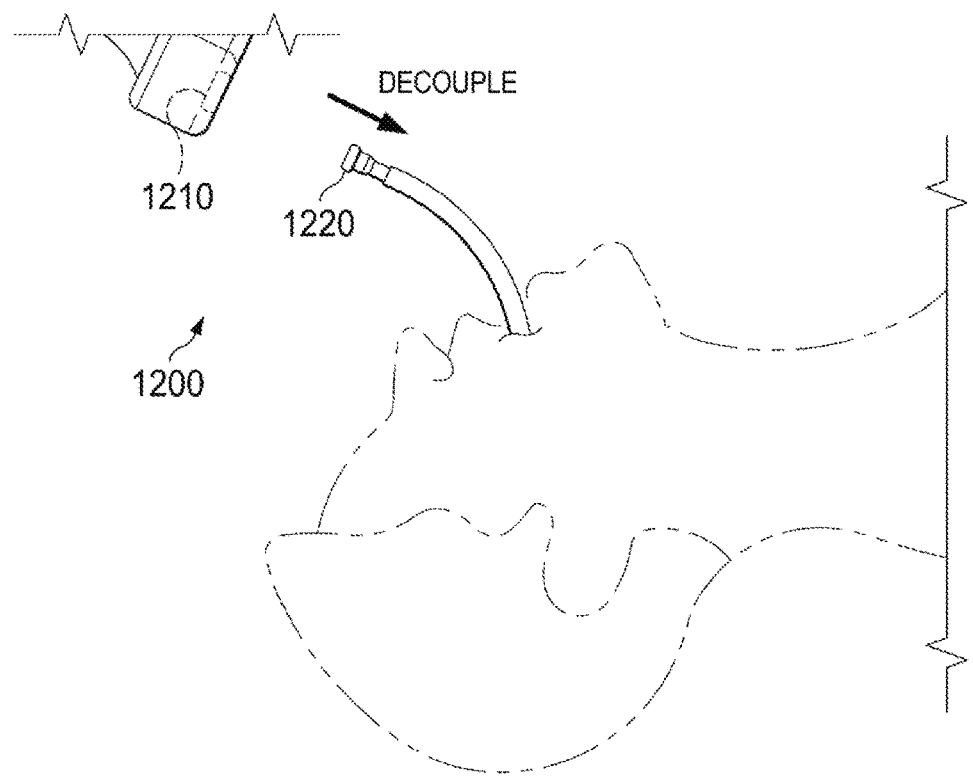

FIG. 13 illustrates a mechanism according to an embodiment of the present disclosure.

Figure 14:
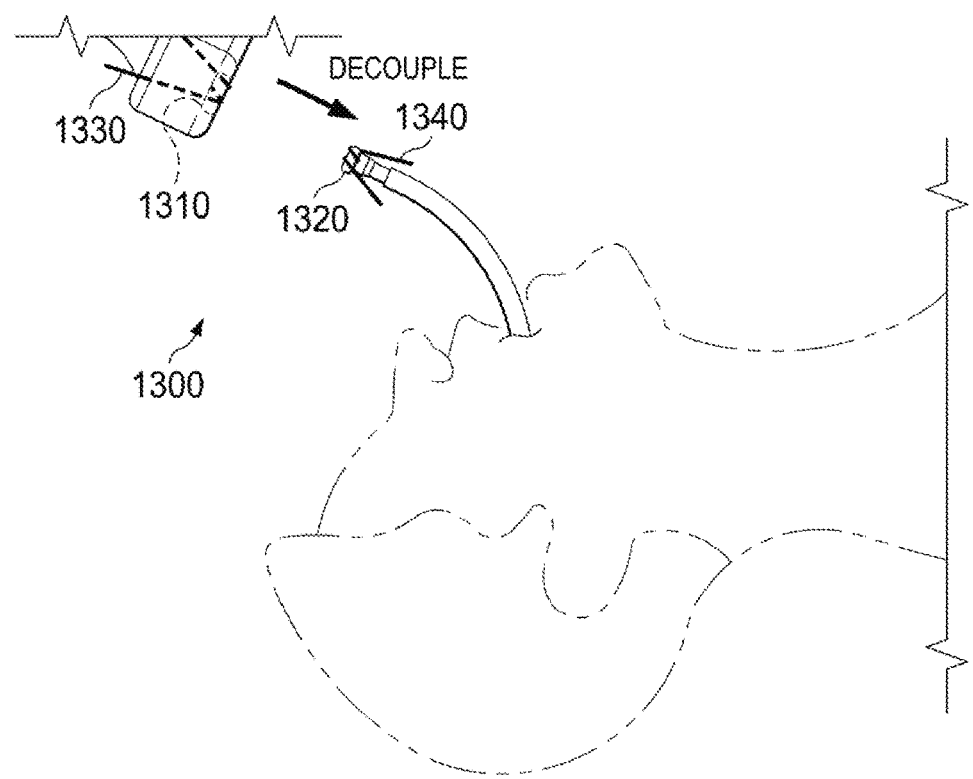

FIG. 14 illustrates a mechanism according to an embodiment of the present disclosure.

Figure 15:
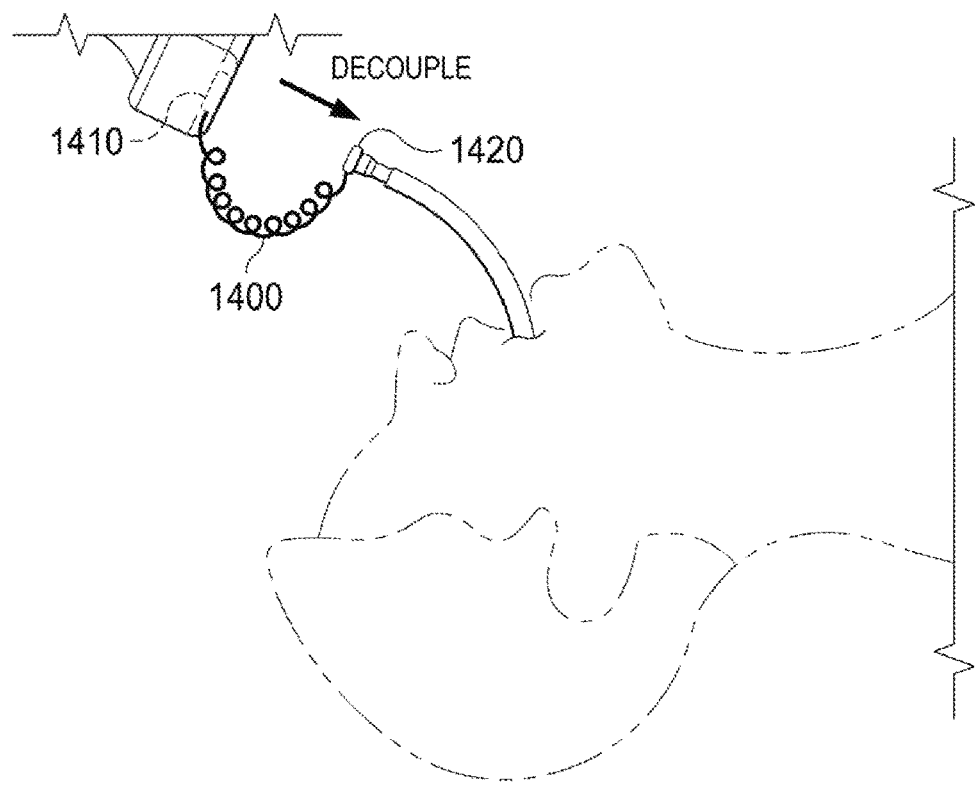

FIG. 15 illustrates a spring mechanism according to an embodiment of the present disclosure.

Figure 16:
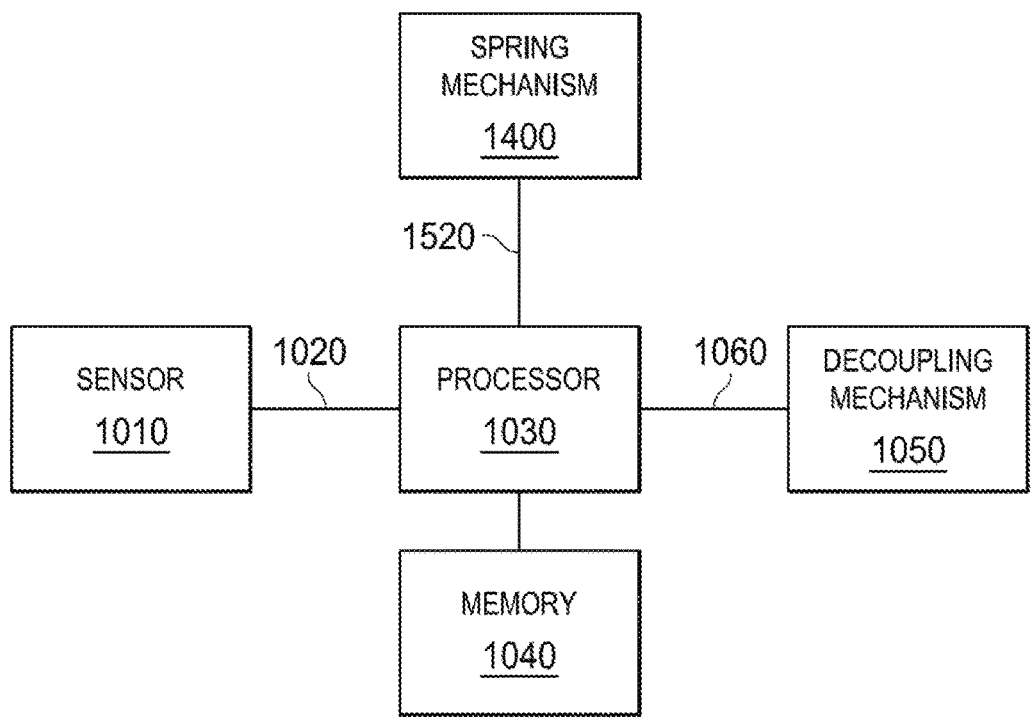

FIG. 16 illustrates a block diagram of system according to an embodiment of the present disclosure.

Figure 17:
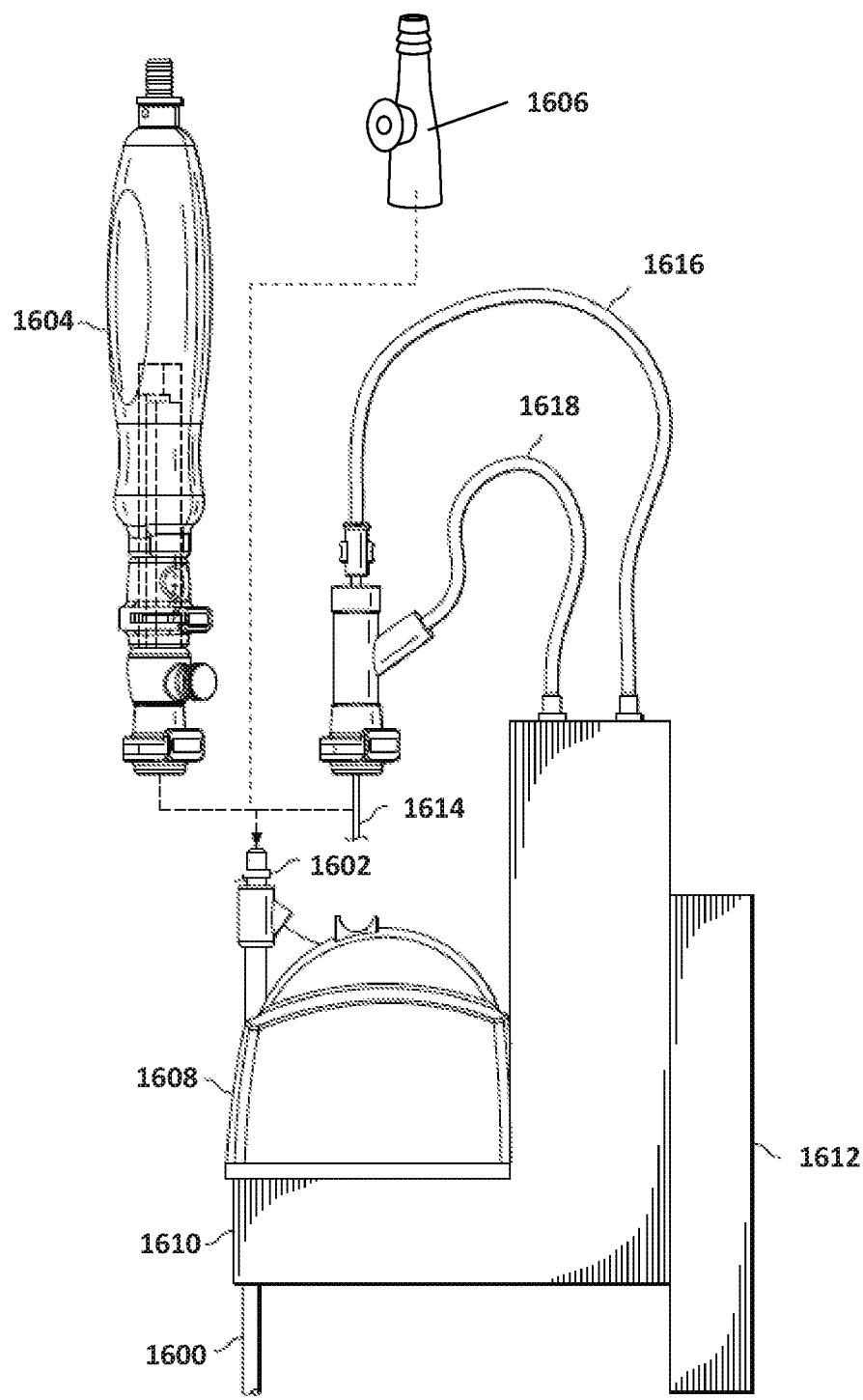

FIG. 17 illustrates couplings between an elongate device and other components via a device port according to an embodiment of the present disclosure.

FIG. 18 illustrates a suction adapter according to an embodiment of the present disclosure.

FIGS. 19A and 19B illustrate a connection mechanism according to some embodiments of the present disclosure.

Figure 20A:
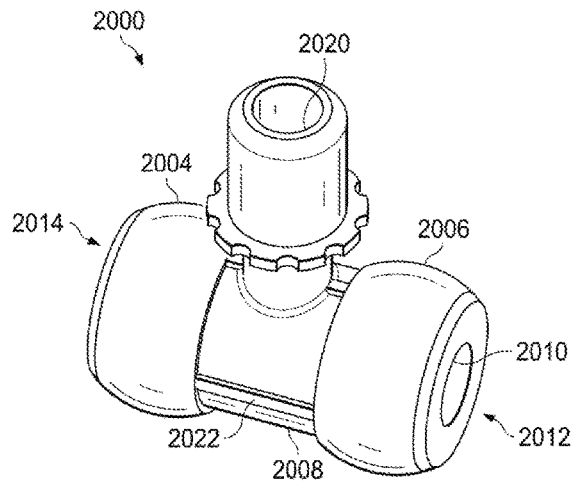
Figure 20B:
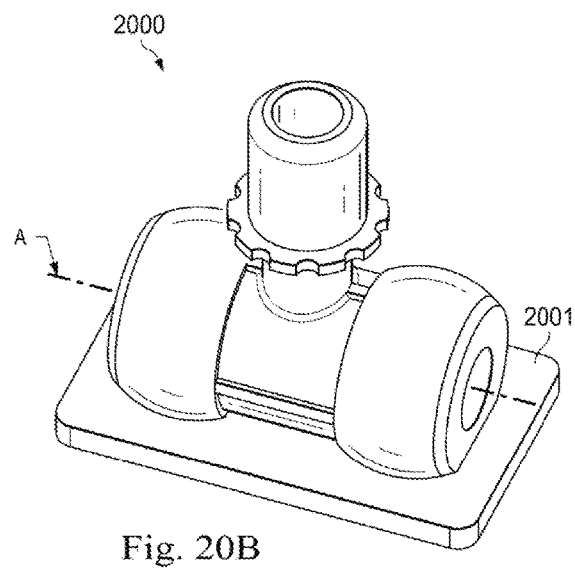

FIGS. 20A and 20B illustrate a connection mechanism according to some embodiments of the present disclosure.

Figure 21A:
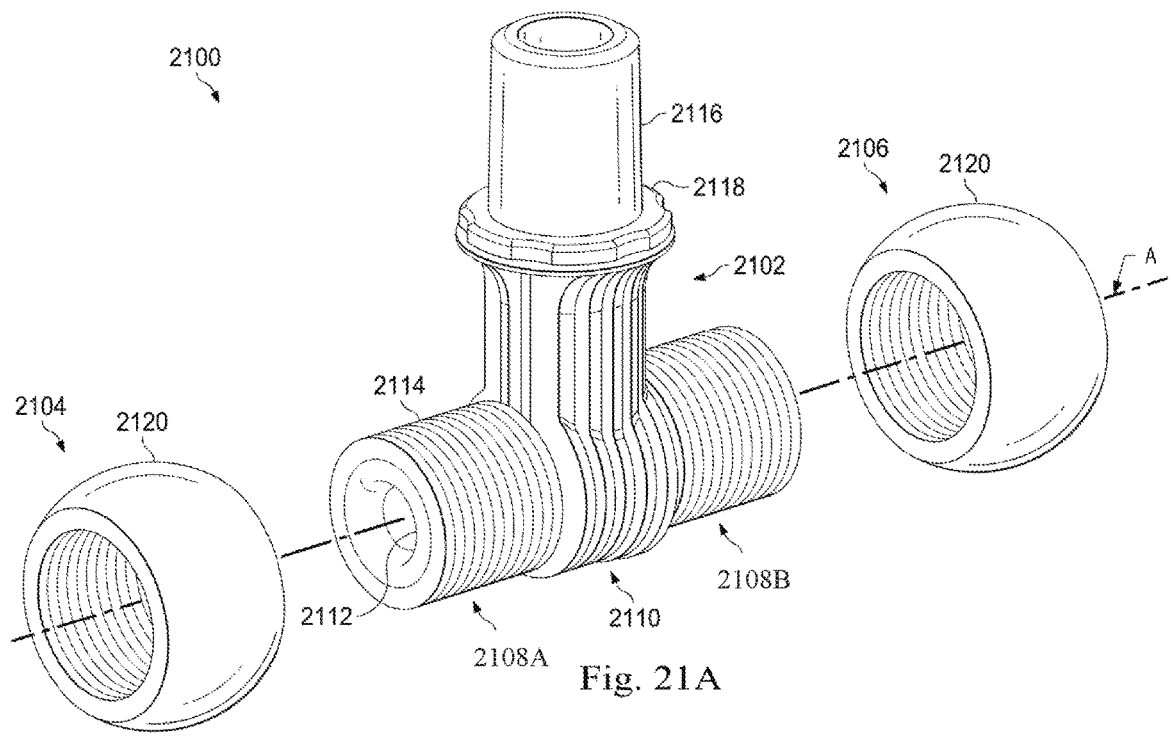

FIGS. 21A and 21B illustrate a connection mechanism at various stages of manufacture according to some embodiments of the present disclosure.

FIGS. 22A and 22B illustrate a connection mechanism at various stages of manufacture according to some embodiments of the present disclosure.

Figure 23A:
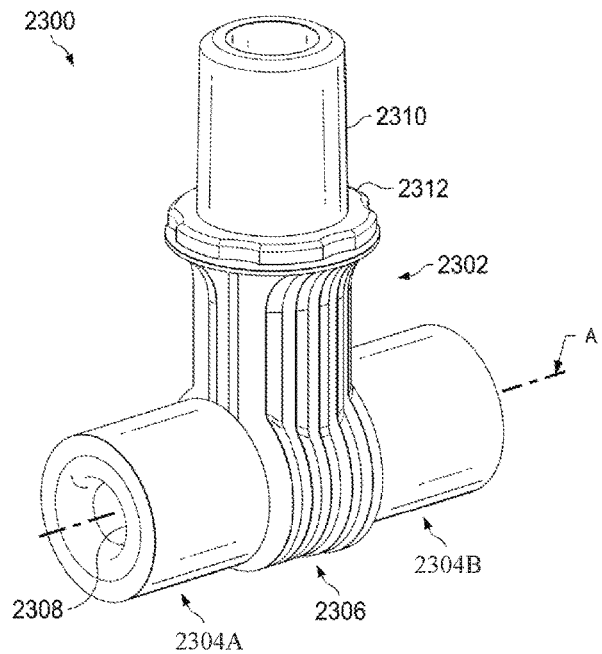
Figure 23B:
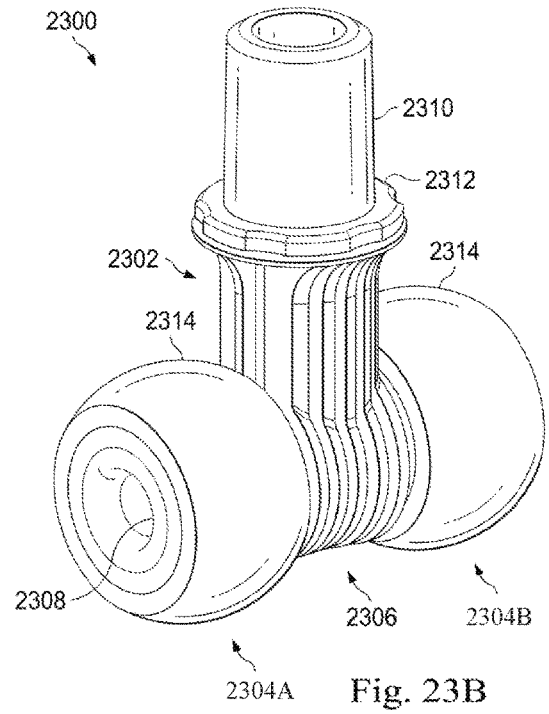

FIGS. 23A and 23B illustrate a connection mechanism at various stages of manufacture according to some embodiments of the present disclosure.

Figure 24A:
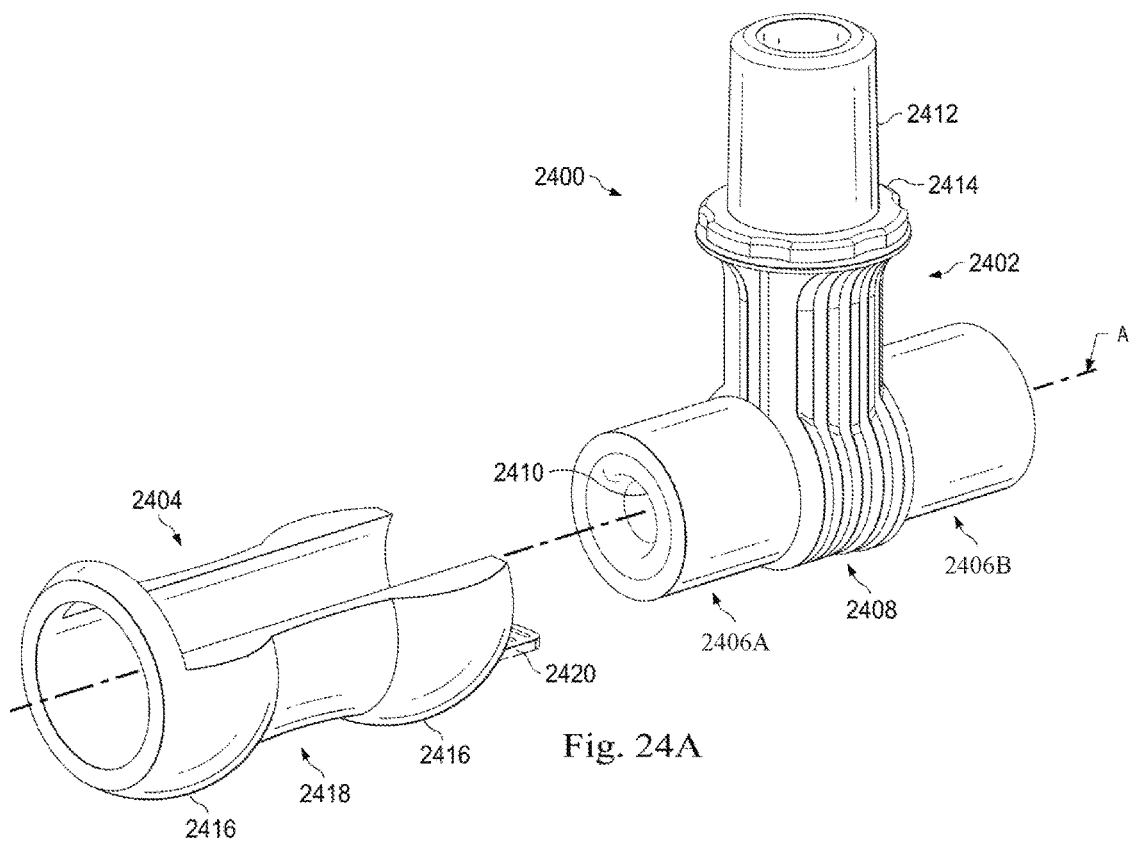
Figure 24B:
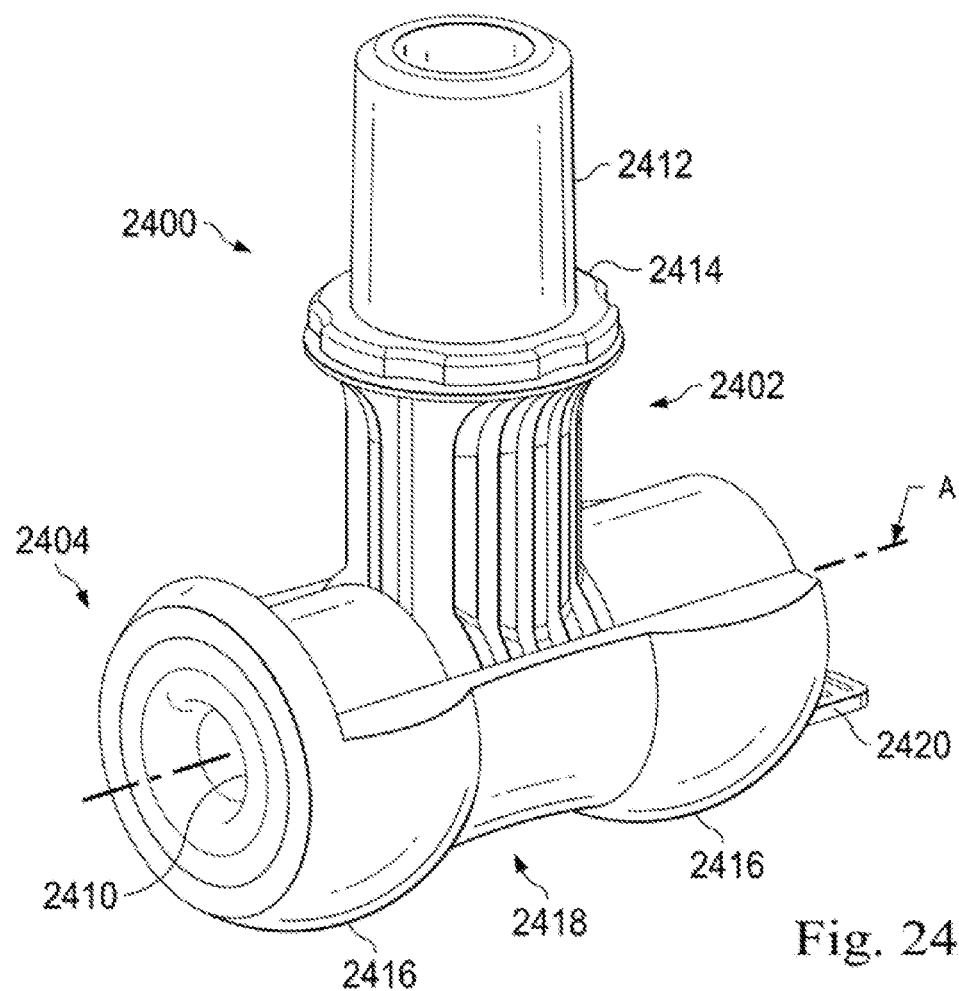

FIGS. 24A and 24B illustrate a two-part connector according to some embodiments of the present disclosure.

Figure 25A:
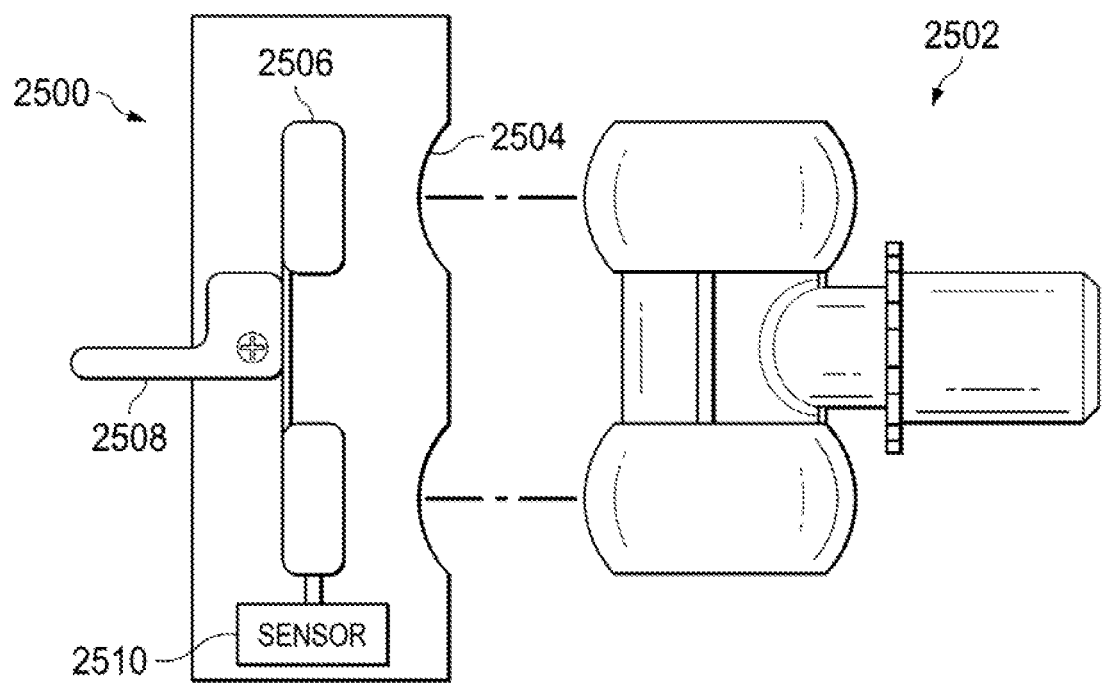
Figure 25B:
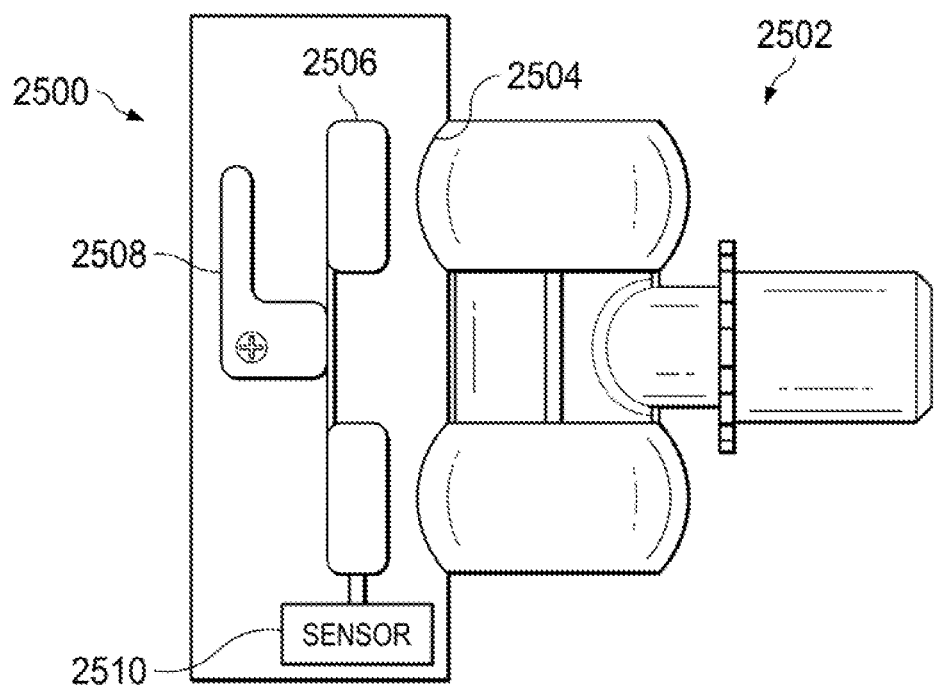

FIGS. 25A and 25B illustrate a bracket for mating to a connection mechanism according to some embodiments of the present disclosure.

Figure 26:
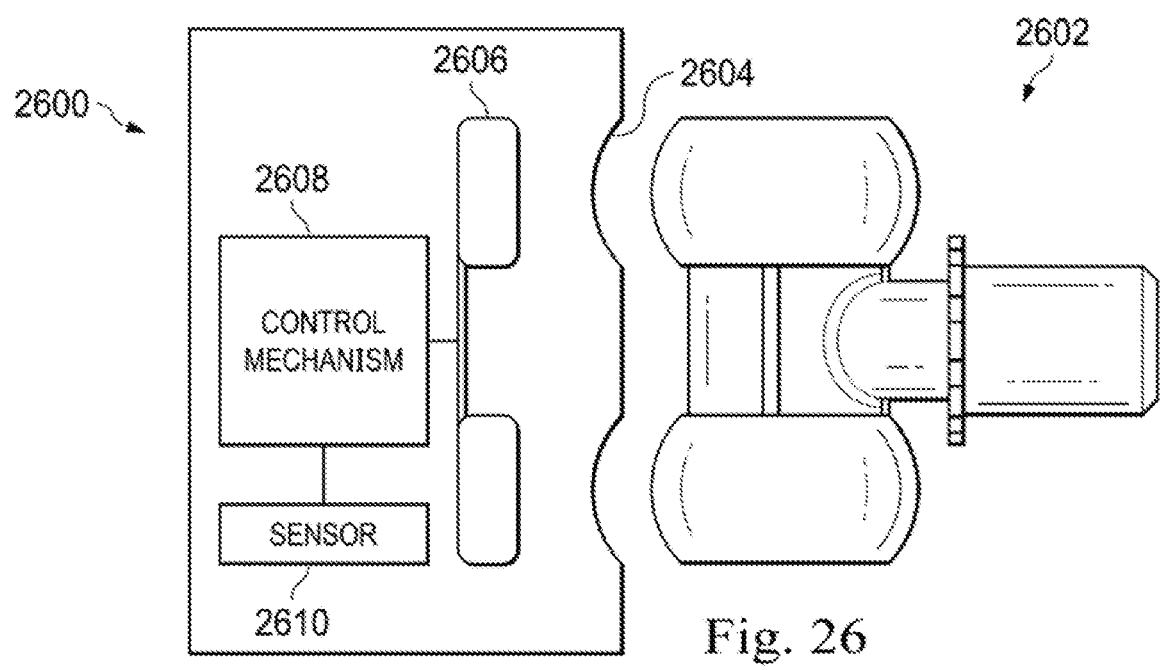

FIG. 26 illustrates a bracket for mating to a connection mechanism according to some embodiments of the present disclosure.

Figure 27:
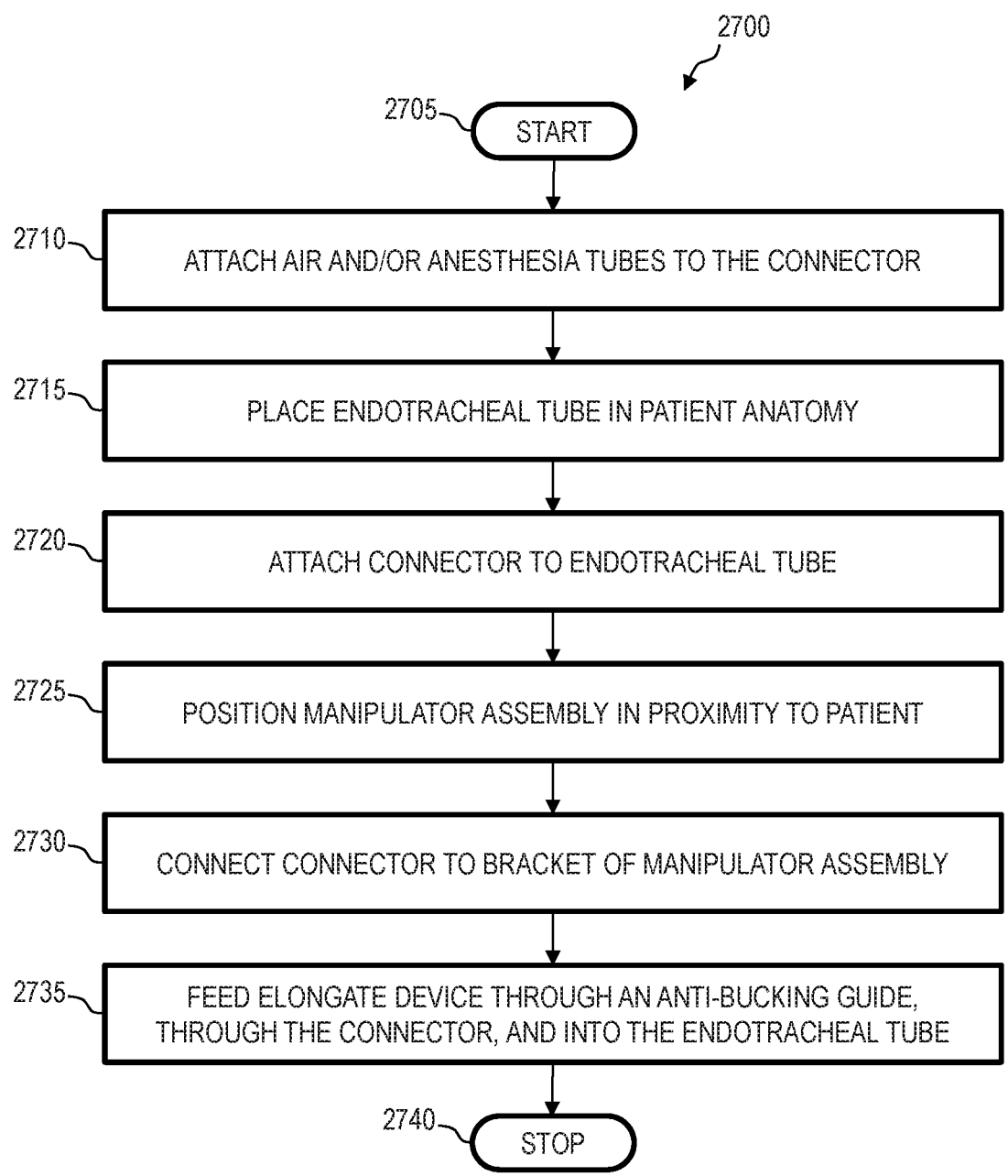

FIG. 27 illustrates a method for installing a connector according to an embodiment of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian X-, Y-, and Z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 6A:
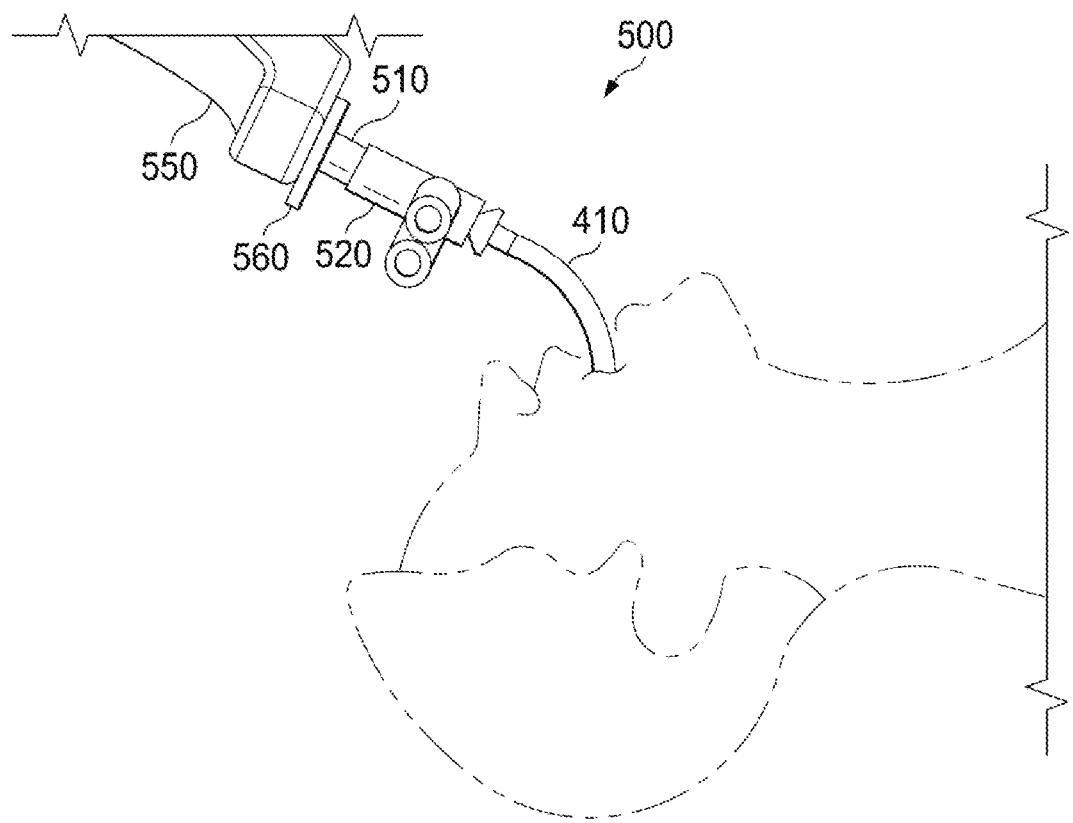
Figure 6B:
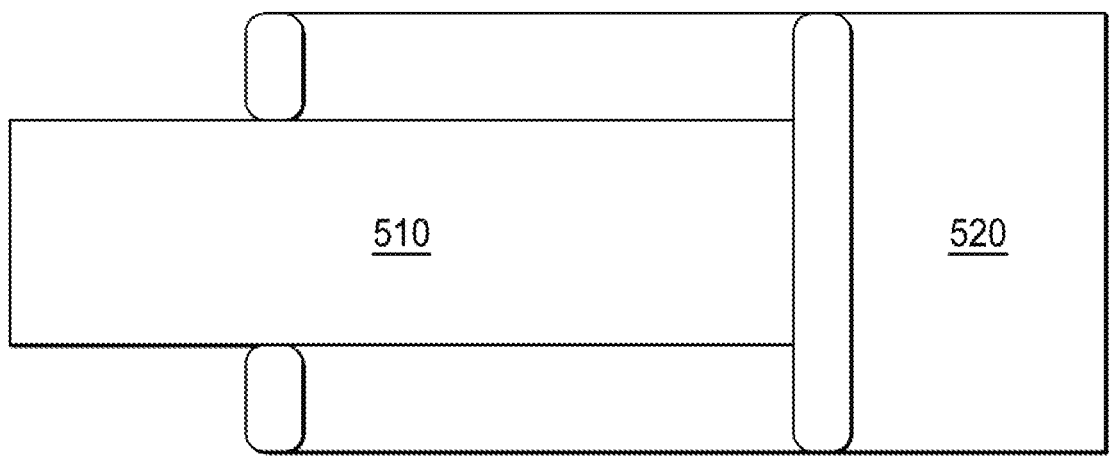
Figures 1, 6C:
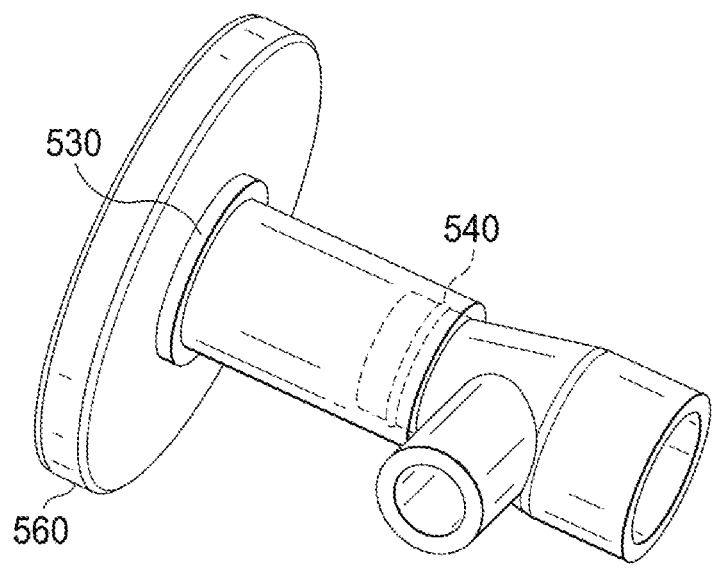
FIG. 1 is a simplified diagram of a robotic and/or teleoperated medical system according to some embodiments.

FIG. 1 is a simplified diagram of a robotic and/or teleoperated medical system 100 according to some embodiments. In some embodiments, medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator O (e.g., a surgeon, a clinician, and/or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

The manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. The manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may include components of an imaging system that records a concurrent or real-time image of a surgical site and provides the image to the operator or operator O through one or more displays of medical system 100, such as one or more displays of display system 110. The imaging system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence.

Medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided medical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery") and U.S. patent application Ser. No. 13/107,562 (filed May 13, 2011) (disclosing "Medical System Providing Dynamic Registration of a Model of an Anatomic Structure for Image-Guided Surgery"), each of which is incorporated by reference herein in its entirety, discloses such systems. Medical system 100 may further include optional operations and support systems (not shown) such as illumination systems, steering control systems, irrigation systems, and/or suction systems. In some embodiments, medical system 100 may include more than one manipulator assembly and/or more than one master assembly. The exact number of teleoperational manipulator assemblies will depend on the medical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
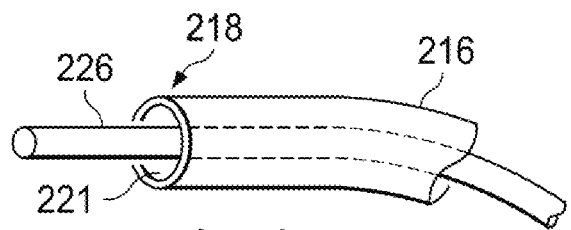
FIG. 2B is a simplified diagram of a medical instrument with an extended medical tool according to some embodiments.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an imaging instrument (e.g., an image capture probe) also within flexible body 216. In various embodiments, medical instrument 226 may itself be an imaging instrument (e.g., an image capture probe) that includes a distal portion with a stereoscopic or monoscopic camera at or near distal end 218 of flexible body 216 for capturing images (including video images) that are processed by a imaging system 231 for display and/or provided to tracking system 230 to support tracking of distal end 218 and/or one or more of the segments 224. The imaging instrument may include a cable coupled to the camera for transmitting the captured image data. In some examples, the imaging instrument may be a fiber-optic bundle, such as a fiberscope, that couples to imaging system 231. The imaging instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably bend the distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from imaging system 231 and/or the preoperatively obtained models to provide the operator with real-time position information. In some examples, the real-time position information may be displayed on display system 110 of FIG. 1 for use in the control of medical instrument system 200. In some examples, control system 112 of FIG. 1 may utilize the position information as feedback for positioning medical instrument system 200. Various systems for using fiber optic sensors to register and display a surgical instrument with surgical images are provided in PCT Publication WO 2016/191298 (published Dec. 1, 2016) (disclosing "Systems and Methods of Registration for Image Guided Surgery") and U.S. patent application Ser. No. 13/107,562 (filed May 13, 2011) (disclosing "Medical System Providing Dynamic Registration of a Model of an Anatomic Structure for Image-Guided Surgery"), each of which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
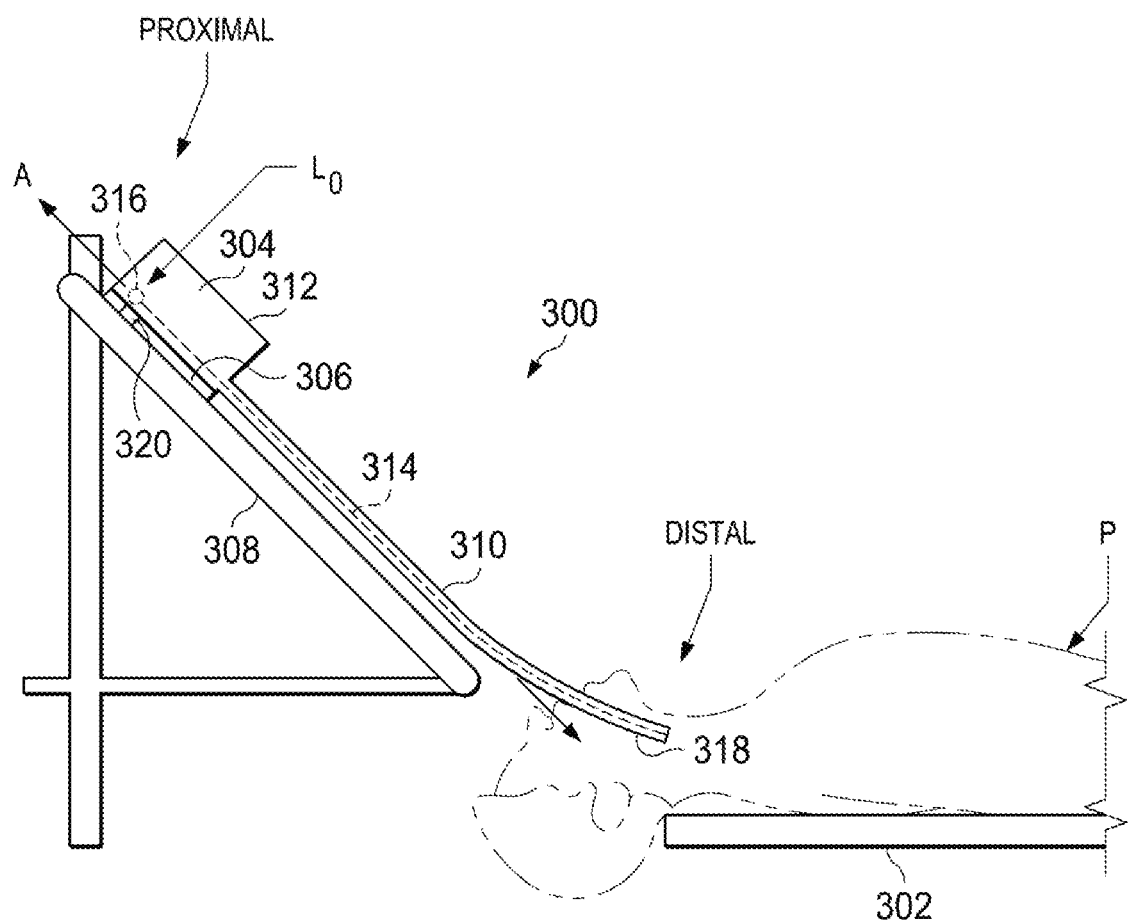
FIGS. 3A and 3B are simplified diagrams of side views of a patient coordinate space including a medical instrument mounted on an insertion assembly according to some embodiments.
Figure 3B:
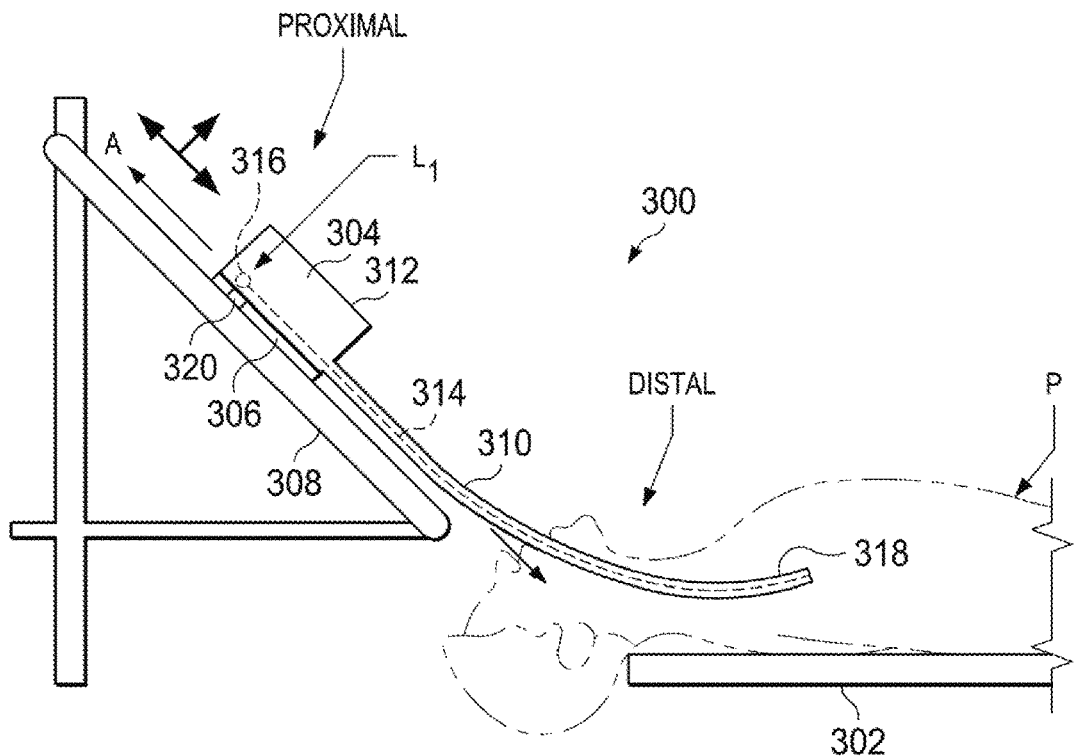

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath, or mechanical ventilation is paused, to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. An airway management device such as an endotracheal (ET)

tube 311 may be inserted in the patient's trachea through the patient's mouth to provide access to the patient's anatomy for the distal end 318 of the instrument body 312. Optionally, the endotracheal tube 311 may be releasably coupled with the insertion stage 308. Also in this position, position measuring device 320 may be set to a zero and/or another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

As discussed above, it would be desirable to provide a connection between the airway management device and a robotic medical system (e.g., a teleoperated medical system) to ensure patient safety during the medical procedure. While the robotic medical system does allow for movement of subassemblies of the robotic medical system relative to ground, the connection between the airway management device and the robotic medical system may be presumed to be in a stationary position to provide a stationary platform during portions of a medical procedure. The present disclosure proposes the use of flexible connectors between an anatomic orifice device, such as the airway management device, and the robotic medical system to accommodate expected and unexpected patient motion. Further, the present disclosure proposes decoupling mechanisms to decouple, when necessary, the flexible connectors between the airway management device and the robotic medical system to ensure patient safety.

In some examples of medical procedures, an airway management device such as an ET tube is inserted through the nose or mouth of a patient and placed within the trachea. The airway management device is connected to a ventilator or a breathing machine, and is used as a conduit to open the airway, and to carry air into the patient's lungs. The ventilator provides mechanical ventilation during the medical procedure. In other words, the airway management device facilitates artificial ventilation when a patient is unconscious or anesthetized during the medical procedure. The medical instrument may then be fed through the airway management device into the patient's airways to view the trachea and other bronchial passages, to diagnose lung diseases and infections, and/or to treat diseased or infected tissue.

Figure 4:
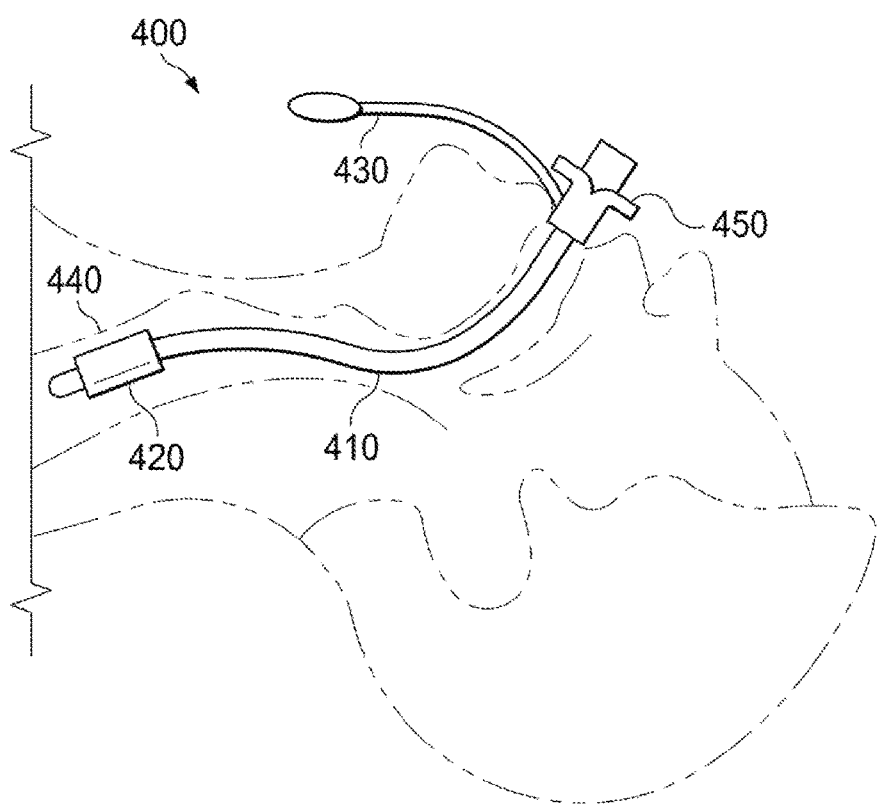
FIG. 4 illustrates an airway management device according to an embodiment of the present disclosure.

FIG. 4 illustrates an example of an airway management device 400 inserted into the patient's trachea through the patient's mouth while the patient lies on their back with the neck slightly extended. The airway management device 400 may comprise an elongated, flexible, and hollow tube 410 which may be curved between its distal and proximal ends for insertion through the upper airway passages into the trachea 440. The airway management device 400 may also include an inflatable balloon-like structure or cuff 420 disposed at the distal end that is inflated using a cuff-inflating tube 430. This balloon-like structure or cuff 420 seals the trachea and bronchial tree, thereby preventing air being pumped by a ventilator/breathing machine connected to the proximal end of the tube 410 from escaping backward through the trachea 440 and entering the oral and nasal passages. As shown, airway management device 400 is placed within the trachea of the patient. In one example, the airway management device 400 may be mounted or constrained near the mouth of the patient by using a mount 450 attached to the tube 410.

When the medical procedures are performed using medical instruments and a robotic medical system (e.g., a teleoperational system) such as the medical system 100 of FIG. 1, a connection is provided between the robotic medical system and the airway management device 400. In one embodiment, the robotic medical system includes a manipulator assembly, such as the manipulator assembly 102 of FIG. 1, and the connection is made between the airway management device 400 and the manipulator assembly. This connection allows the robotic medical system to couple to the airway management device 400, and to introduce surgical or bronchial instruments therein. To avoid trauma to the patient due to expected or unexpected patient motion during the medical procedure and/or to avoid dislodgement of the airway management device from the patient's trachea, in one embodiment, the present disclosure proposes introducing a flexible connection mechanism between the robotic medical system and the airway management device 400. The flexible connection mechanism is configured to move in various degrees of freedom to accommodate for the expected and unexpected patient motion. In cases where the patient motion causes a significant amount of displacement, and therefore force on the connection mechanism between the robotic medical system and the airway management device 400, the present disclosure proposes mechanisms to decouple the connection mechanism from either the robotic medical system or from the airway management device. The mechanisms may be purely mechanical or may include sensors to sense the forces on the connection, and decouple, when necessary, the connection when the forces exceed a predetermined threshold to ensure patient safety. Alternatively, patient motion may be sensed using sensors coupled to the patient.

Regarding the decoupling of the airway management device 400 from the robotic medical system, for all embodiments discussed below, the decoupling may occur at one or more of several different couplings. For example, the decoupling may occur between the robotic medical system and a medical system interface that is connected to the airway management device through a connection mechanism. Additionally or alternatively, the decoupling may occur between the interface and the connection mechanism at a first joint. In case there is no medical system interface, and the airway management device is directly connected to the robotic medical system, the decoupling may occur at the direct connection between the robotic medical system and the connection mechanism, leaving the connection mechanism coupled to the airway management device. The decoupling may also occur between a first end and a second end within the connection mechanism. Additionally or alternatively, the decoupling may occur between the connection mechanism and the airway management device at a second joint.

During robotic medical procedures, it is important to account for safety of the connection provided between the airway management device 400 and the manipulator assembly 102 (e.g., of a teleoperational or other robotic medical system). In the event that the patient moves from a default position relative to the robotic medical system, where the robotic medical system may be presumed to be stationary, the connection between the airway management device 400 and the robotic medical system should accommodate the patient's motion. The present disclosure proposes use of connection mechanisms to connect the airway management device 400 to the robotic medical system for accommodation of the patient's motion. The connection mechanisms may include mechanical assemblies which are compact, and connect the airway management device 400 to the robotic medical system by a combination of mechanical, electromechanical, magnetic, electromagnetic, and/or pneumatic mechanisms. A connection mechanism may include a short length or a service loop flexible medium such as an elastomer hose or a spiral corrugated hose able to enclose and support the bronchial instruments.

The connection mechanisms are configured to move in multiple degrees of freedom to accommodate the patient's motion. In this way, the connection mechanisms assist in controlling retention of the connection by avoiding unnecessary disconnection of the robotic medical system from the airway management device 400 when the patient motion causes only a minor displacement. The motion of the connection mechanisms also provides additional time before decoupling of the airway management device 400 from the robotic medical system. For instance, a decoupling procedure to release the airway management device 400 from the robotic medical system may be initiated upon motion of the connection mechanisms or of the patient. Accommodation of the patient's motions during this time significantly reduces risk of injury to the patient.

Figure 5:
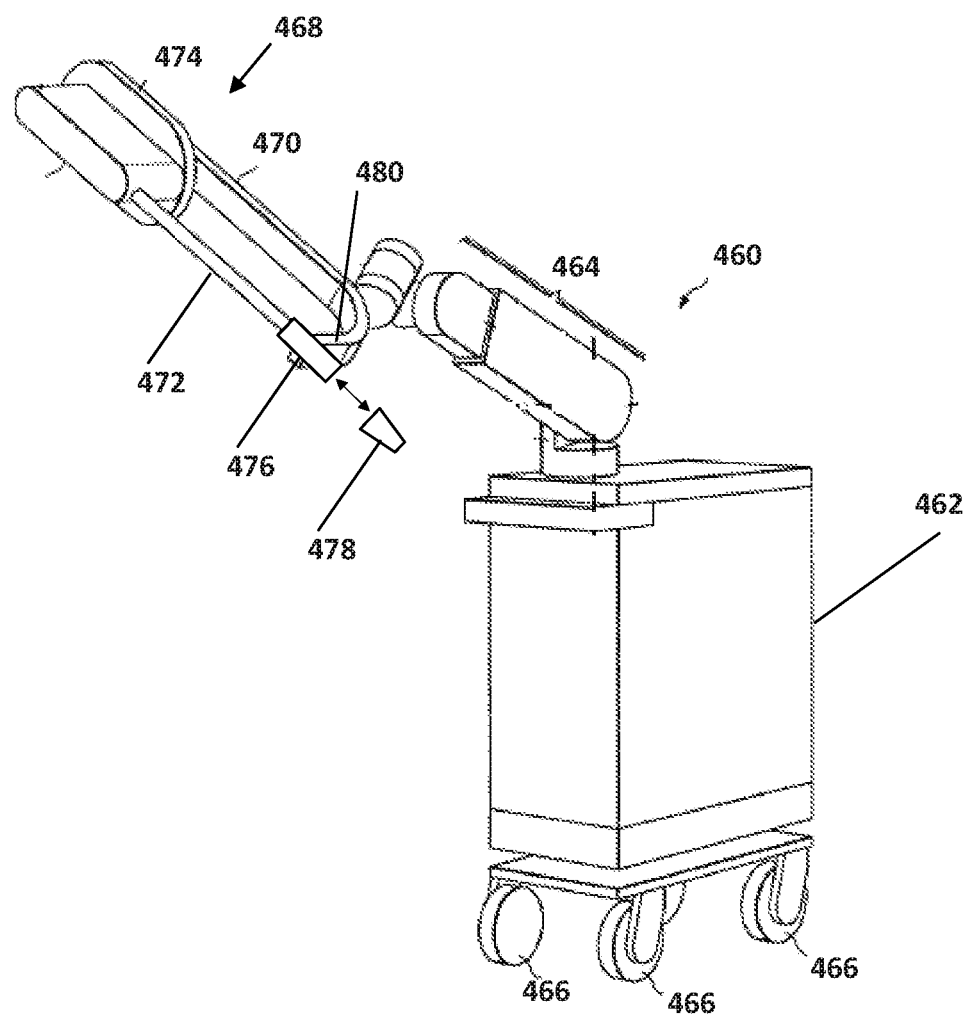
FIG. 5 illustrates a manipulator assembly according to an embodiment of the present disclosure.

FIG. 5 illustrates a manipulator assembly 460 that includes a cart 462 (e.g., a base) and a support structure 464. Optionally, the cart 462 may be mounted on a set of wheels 466 to allow positioning of the cart 462 at a desired location relative to the operating table T and the patient P. The cart 462 may also house various components including processors, monitors, vacuum equipment, air canisters, cables, etc. for performing various procedures on the patient P. A distal end of the support structure 464 may be coupled to a flexible instrument manipulator (FIM) 468 (e.g., a type of manipulator assembly 102) that includes an insertion stage 470 (e.g., insertion stage 308) and a carriage 474 (e.g., carriage 306) to which an elongate device 472 (e.g., elongate device 1600) is coupled. A movable connection mechanism 476 is coupled to a docking spar 480 at a distal end of the insertion stage 470. The movable connection mechanism 476 couples the elongate device 472 to an endotracheal tube 478 (e.g., endotracheal tube 311).

The endotracheal tube 478 is inserted into the mouth and trachea of the patient to help provide mechanical ventilation for the patient and to provide a conduit for the elongate device 472 to be inserted into the lungs of the patient. While the elongate device 472 is being navigated into the lungs to facilitate imaging, biopsy, and/or treatment, the patient may experience coughing, unexpected motion, or reduced sedation which may dislodge the endotracheal tube from the patient and disrupt ventilation. To minimize any consequences of this unexpected motion, the movable connection mechanism 476 may be releasable from the docking spar 480.

Examples of suitable connection mechanisms for coupling with the manipulator assembly 460 or other component of a robotic medical system are described with reference to the following figures. FIGS. 6A-D illustrate a connection mechanism 500 according to an embodiment of the present disclosure. As shown in FIG. 6A, the connection mechanism 500 includes a medial portion including a first flexible tube 510 and a second flexible tube 520 nested together in a telescopic configuration. One end of the first flexible tube 510 is connected to a robotic medical system 550 through a medical system interface 560. The robotic medical system 550 may be presumed to be in a stationary position to provide a stationary platform. One end of the second flexible tube 520 may be connected to the airway management device 400, which includes the tube 410 inserted into the patient's mouth for the medical procedure. Both flexible tubes 510, 520 may be made of medical grade materials such as polyurethane, silicone, flexible PVC, or the like. Also, the flexible tubes 510, 520 may be hollow to allow insertion of bronchial or other instruments through the tubes.

In the nested telescopic configuration, the first flexible tube 510 may be fitted within the second flexible tube 520 using a mechanical lip structure illustrated in FIG. 6B. The mechanical lip structure allows the first flexible tube 510 to move with full range of longitudinal motion along the entire length of the second flexible tube 520 without, in the absence of adequate force, decoupling from the second flexible tube 520. In addition to the flexibility in the longitudinal direction, both tubes 510, 520 are flexible tubes that provide 360° of freedom for flexibility in the lateral direction. Critically, the flexibility of the flexible tubes 510, 520 in the lateral direction may be a function of the diameter of the tubes 510, 520. In general, the smaller the diameter of a flexible tube, the higher the flexibility of the flexible tube in the lateral direction, and the larger the diameter of a flexible tube, the lower the flexibility of the flexible tube in the lateral direction. The first flexible tube 510 may have smaller diameter with respect to the second flexible tube 520 to facilitate the nested telescopic configuration. Additionally or alternatively, the flexibility of the flexible assembly may be a function of the diameter of the first flexible tube 510 relative to the second flexible tube 520. For example, a looser fit between the first and second flexible tubes 510, 520 may allow for more lateral flexibility than a tighter fit. Both flexible tubes 510, 520 may have substantially the same length. Alternatively, the first flexible tube 510 may have different length with respect to the second flexible tube 520. In further alternative embodiments, the connection mechanism 500 may include a plurality of flexible tubes, where the tubes increase in diameter from their proximal to distal ends, or decrees in diameter from the proximal to distal ends, or alternate in diameter along the length of the connection mechanism 500.

Figures 2, 6C:
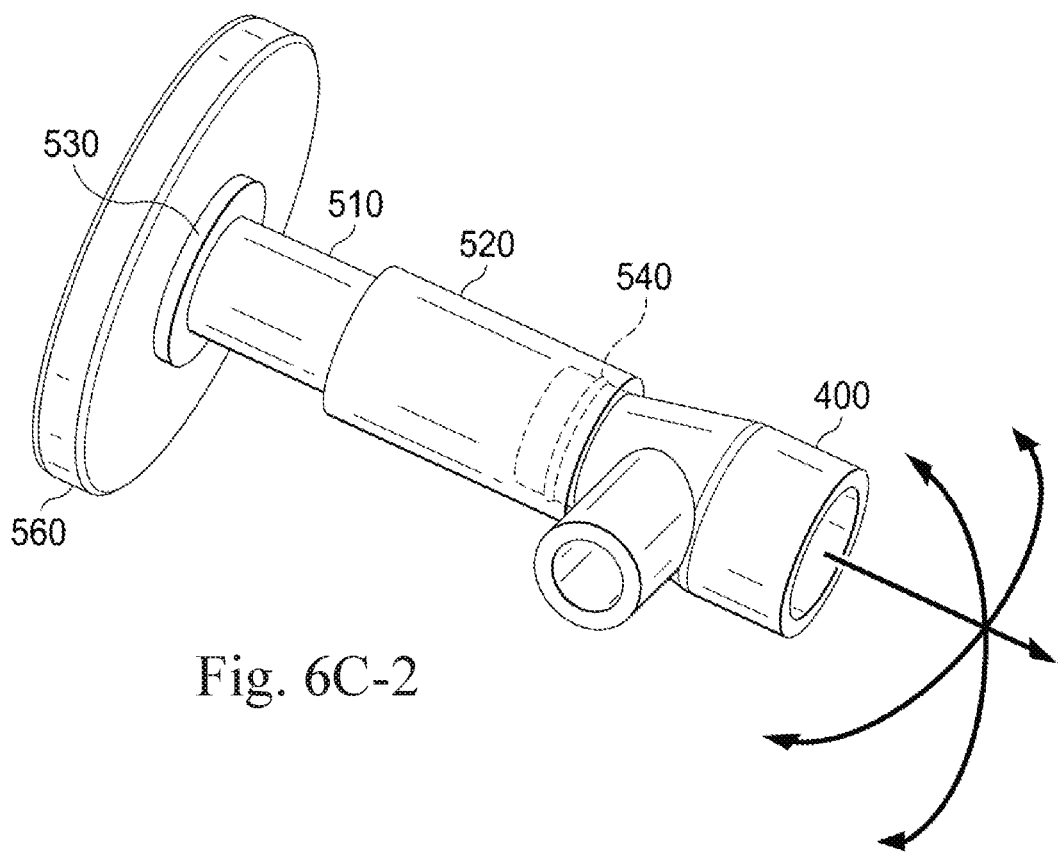
FIG. 2A is a simplified diagram of a medical instrument system according to some embodiments.

FIGS. 6C-1 and 6C-2 illustrate further details of the connection mechanism 500. In particular, FIG. 6C-1 illustrates a position of the connection mechanism 500 in which the first flexible tube 510 is completely inserted or covered by the second flexible tube 520. FIG. 6C-1 also illustrates the joint 530 at which a first end portion of the first flexible tube 510 is connected to the medical system interface 560, and joint 540 at which a second end portion of the second flexible tube 520 is connected to the airway management device 400. Both joints 530, 540 may be rigid connections about which the flexible tubes flex to provide multiple degrees of freedom for flexibility in the lateral direction. Alternatively, both joints 530, 540 may be flexible connections that provide multiple degrees of freedom for flexibility in the lateral direction in addition to the flexibility provided by the flexible tubes 510, 520. For example, the joint 530 may be movably connected to the medical system interface 560 to allow for movement of the joint 530 in multiple degrees of freedom in the lateral direction. Joints 530, 540 may be implemented using a mechanical lip structure similar to the mechanical lip structure discussed above. Alternatively, one or more of joints 530 and 540 may be implemented using other mechanical and/or electromechanical mechanisms and may be activated by a sensor, as discussed in further detail below. FIG. 6C-2 illustrates an extended position of the connection mechanism 500 in which the first flexible tube 510 extends out of the second flexible tube 520 to provide flexibility in the longitudinal direction.

During the medical procedure, when the patient moves expectedly or unexpectedly to cause a minor displacement, or when unexpected or inadvertent bumping of the robotic medical system causes a minor displacement, the connection mechanism 500 flexes in the lateral and longitudinal directions as much as necessary to accommodate the patient's motion. For example, the flexible tubes 510, 520 and/or the mechanisms used for the joints 530, 540 may flex as much as necessary to provide 360° of freedom in the lateral direction, and the first flexible tube 510 moves as much as necessary with full range of motion along the entire length of the second flexible tube 520 to provide flexibility in the longitudinal direction. In this way, the mechanical lip structure incorporated in the flexible tubes 510, 520 prevents inadvertent decoupling of the first flexible tube 510 from the second flexible tube 520 in the absence of adequate force.

Figure 6D:
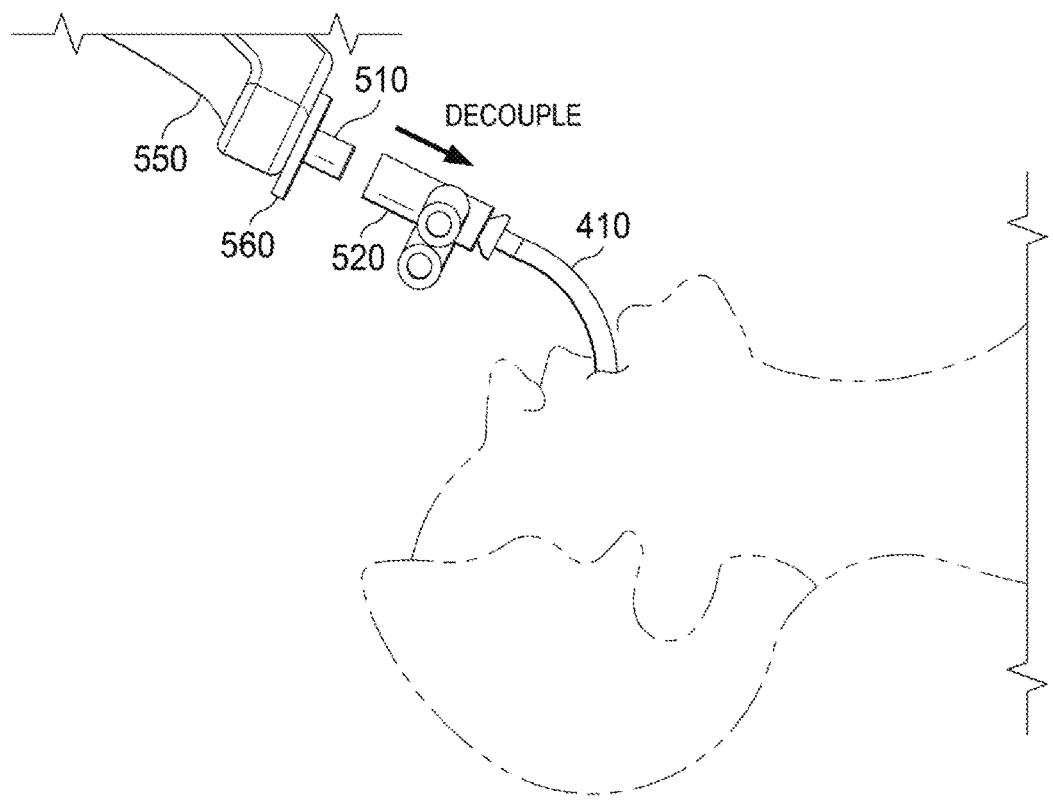

However, when the patient motion causes a major displacement, or when the unexpected or inadvertent bumping of the robotic medical system causes a significant relative displacement, which produces a significant force on the connection between the robotic medical system 550 and the airway management device 400, the connection mechanism 500 enables decoupling of the robotic medical system 550 from the airway management device 400. In an exemplary embodiment, as shown in FIG. 6D, the first flexible tube 510 decouples from the second flexible tube 520. In an alternative embodiment (not shown), the robotic medical system decouples from the medical system interface. Additionally or alternatively, a sensing mechanism senses the significant force at the connection and/or patient movement, and enables decoupling of the first end portion of the first flexible tube 510 from the medical system interface 560 at joint 530 or decoupling of the second end portion of the second flexible tube 520 from the airway management device 400 at joint 540. The sensing mechanism may also enable decoupling at the joint 530 to separate the flexible tube 510 from the medical system interface 560, or decoupling at the joint 540 to separate the flexible tube 520 from the airway management device 400. In this way, when necessary, the connection mechanism 500 that connects the airway management device 400 to the robotic medical system 550 decouples the patient from the robotic medical system to ensure safety of the patient during the medical procedure. Decoupling procedures are described in greater detail with reference to FIGS. 11-16.

Figure 7A:
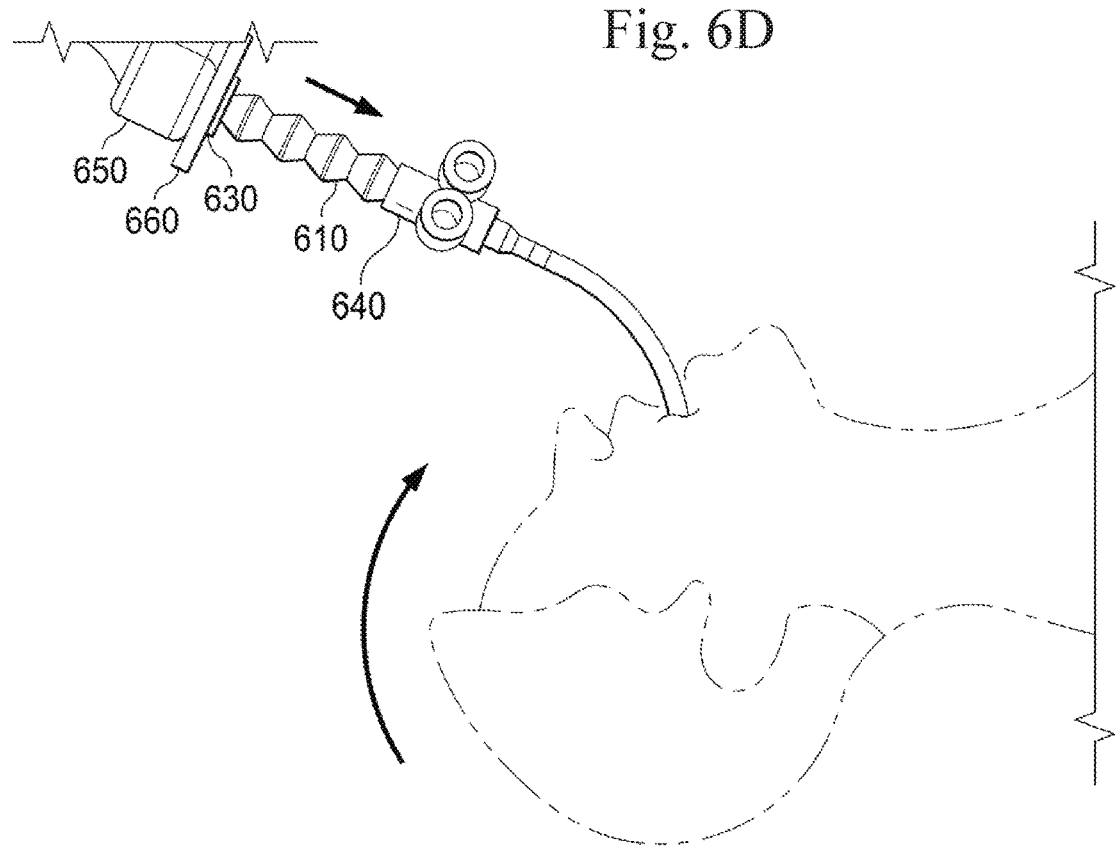

FIGS. 7A-D illustrate a connection mechanism 600 according to the present disclosure. As shown in FIG. 7A, the connection mechanism 600 includes a medial portion including a convoluted or bellowed tube 610 that provides accordion or bellows type movement. The bellowed tube 610 may be hollow and may provide a small, well constrained working channel for bronchial instruments. The bellowed tube 610 may be made, at least partially, of medical grade materials such as polyurethane, silicone, flexible PVC, thermoplastics, thermoset plastics, or the like. One end of the bellowed tube 610 is connected to a robotic medical system 650 at a first end portion of the connection mechanism 600 or through a medical system interface 660. The robotic medical system 650 may be presumed to be in a stationary position to provide a stationary platform. The other end of the bellowed tube 610 may be connected through an adaptor 670 to the airway management device 400, which includes the tube 410 inserted into the patient's mouth for the medical procedure. In this configuration, the bellowed tube 610 may fold or unfold along its entire length to provide flexibility in the longitudinal direction without, in the absence of adequate force, decoupling from the medical system interface 660. In addition to the flexibility in the longitudinal direction, the bellowed tube 610 is flexible to provide 360° of freedom in the lateral direction. Critically, the flexibility of the bellowed tube 610 in the lateral direction may be a function of its diameter. The smaller the diameter of the bellowed tube 610, the higher its flexibility in the lateral direction, and the larger the diameter of the bellowed tube 610, the lower its flexibility in the lateral direction. The bellowed tube 610 may also have a high aspect ratio. For instance, the ratio of the length of the bellowed tube 610 in its unfolded position to the length of the bellowed tube 610 in its folded position may be high.

FIG. 7A also illustrates the joint 630 at which the bellowed tube 610 is connected to the medical system interface 660, and joint 640 at which a second end portion of the bellowed tube 620 is connected to the airway management device 400. Both joints 630, 640 may be rigid connections about which the flexible bellowed tube 610 flexes to provide multiple degrees of freedom in the lateral direction. Alternatively, both joints 630, 640 may be flexible connections that provide multiple degrees of freedom for flexibility in the lateral direction in addition to the flexibility provided by the flexible bellowed tube 610. For example, the joint 630 may be movably connected to the medical system interface 660 to allow for movement of the joint 630 in multiple degrees of freedom in the lateral direction. Joints 630, 640 may be implemented using a mechanical lip structure similar to the mechanical lip structure discussed above. Alternatively, one or more of joints 630, 640, 660 may be implemented using other mechanical and/or electromechanical mechanisms that may be activated by a sensor, as discussed in further detail later on with respect to the sensing mechanism 1000.

Figure 7B:
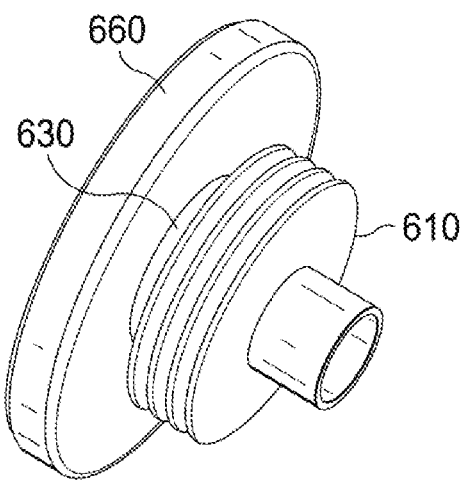
Figure 7C:
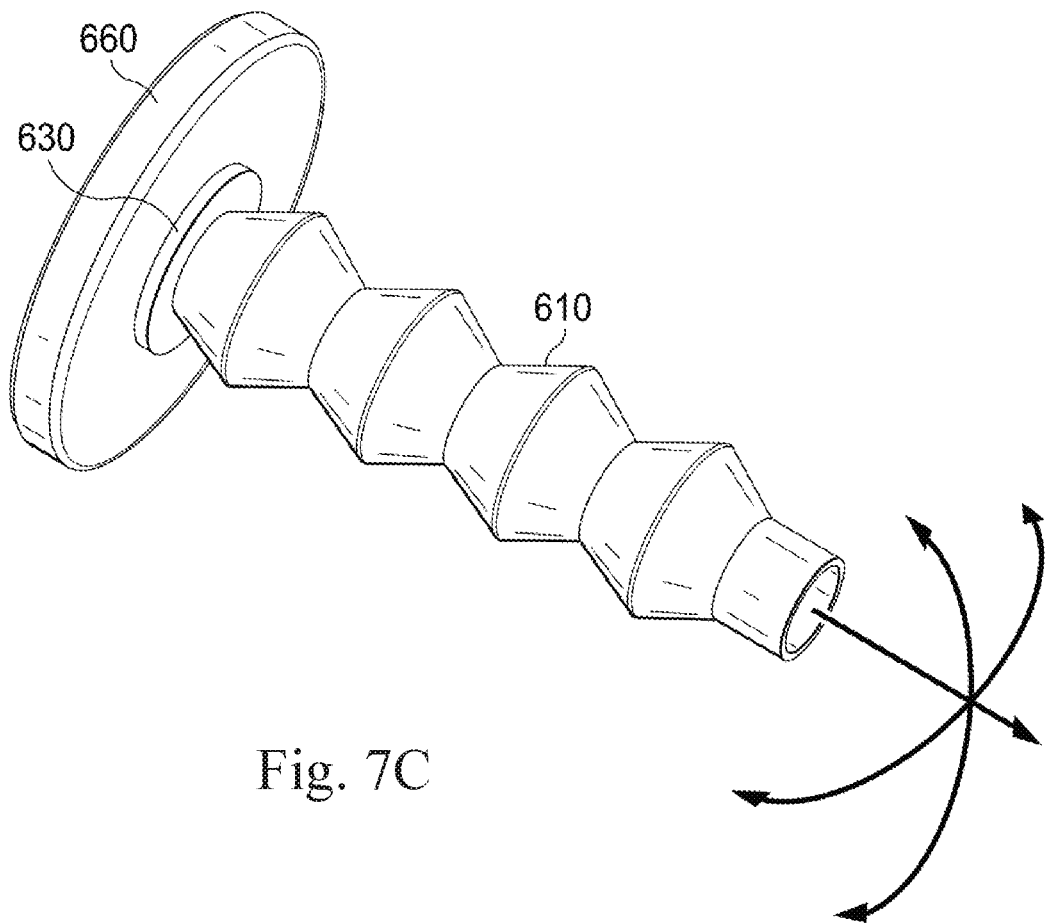

FIGS. 7B and 7C illustrate further details of the connection mechanism 600. In particular, FIG. 7B illustrates a contracted position of the connection mechanism 600 in which the bellowed tube 610 is completely folded. FIG. 7C illustrates an extended position of the connection mechanism 600 in which the bellowed tube 610 is unfolded to provide flexibility in the longitudinal direction.

During the medical procedure, when the patient moves expectedly or unexpectedly to cause a minor displacement, or when inadvertent bumping of the robotic medical system causes a minor displacement, the connection mechanism 600 flexes as much as necessary in the lateral and longitudinal directions to accommodate the patient's motion. For example, the bellowed tube 610 and/or the mechanisms used for the joints 630, 640 flex as much as necessary to provide 360° of freedom in the lateral direction, and the bellowed tube 610 unfolds as much as necessary from its default position along an entire length of the bellowed tube 610 to provide flexibility in the longitudinal direction. In this way, the mechanical lip structures and/or mechanical and electromechanical mechanisms prevent inadvertent decoupling of the bellowed tube 610 from either one of its connections at joints 630, 640 in the absence of adequate force.

Figure 7D:
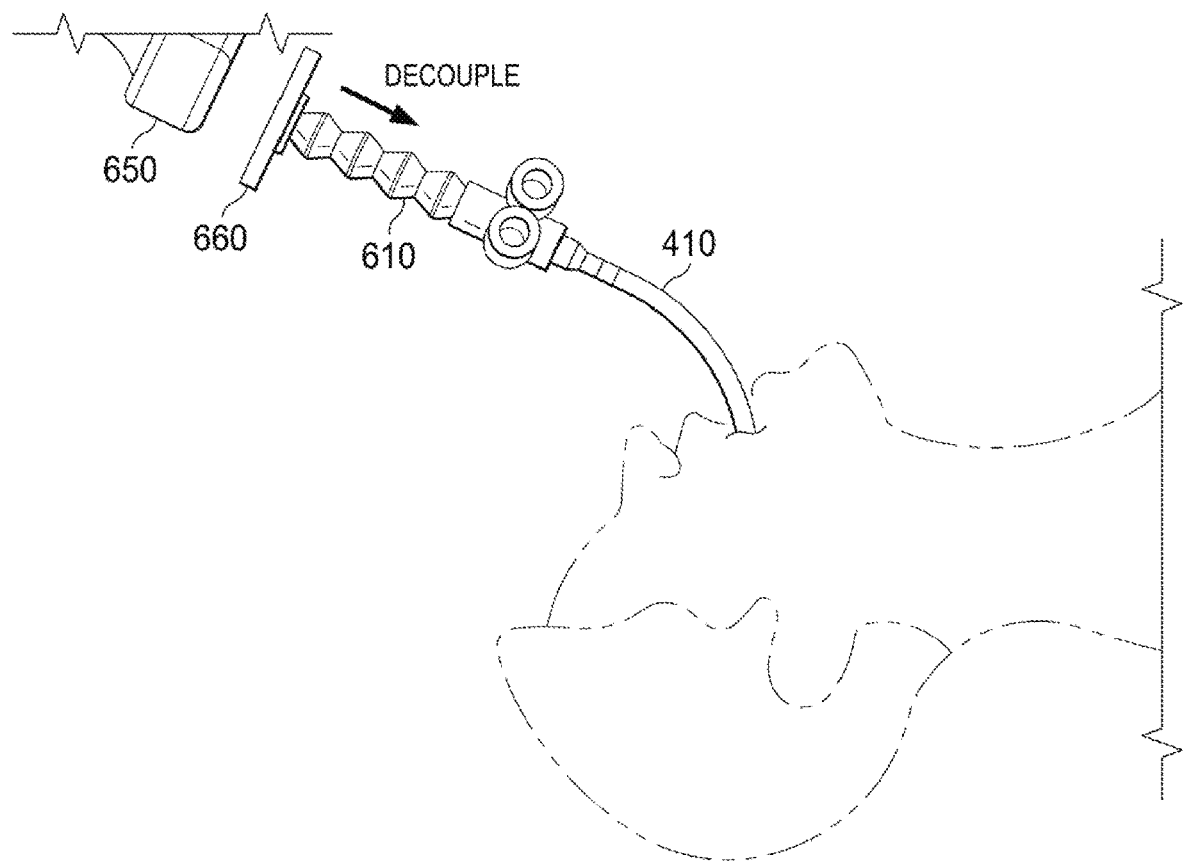

However, when the patient motion causes a major displacement, or when the unexpected or inadvertent bumping of the robotic medical system causes a significant relative displacement, which produces a significant force on the connection between the robotic medical system 650 and the airway management device 400, the mechanical lip structures and/or mechanical and electro-mechanical mechanisms enable decoupling of the robotic medical system 650 from the airway management device 400 as shown in, for example, FIG. 7D. In an exemplary embodiment, the sensing mechanism senses the significant force at the connection and/or patient movement, and enables decoupling of the bellowed tube 610 from the medical system interface 660 at joint 630 or decoupling of the medical system interface 660 from the robotic medical system 650. Additionally or alternatively, the sensing mechanism may enable decoupling of the bellowed tube 610 from the airway management device 400 at joint 640. In this way, when necessary, the connection mechanism 600 that connects the airway management device 400 to the robotic medical system 650 decouples the patient from the robotic medical system to ensure safety of the patient during the medical procedure.

Figure 8A:
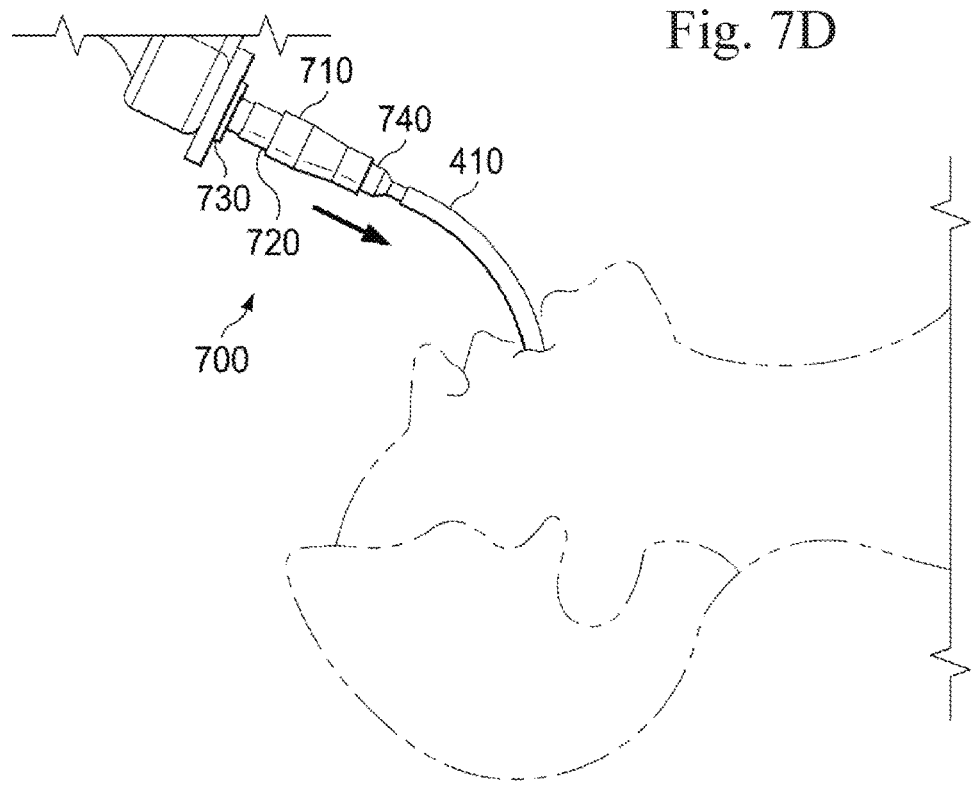

FIGS. 8A-D illustrate a connection mechanism 700 according to the present disclosure. As shown in FIG. 8A, the connection mechanism 700 includes a medial portion that includes a flexible rolling diaphragm. Rolling diaphragms provide high performance in harsh environments, such as a medical environment, by facilitating accurate and repeatable positioning. Rolling diaphragms are capable of withstanding high pressures because of the way they allow load distribution. The mechanism includes a distal portion 710 that at least partially fits over a portion of the rolling diaphragm 720. The rolling diaphragm 720 includes a conical section of flexible tubing which is inverted at one end to enable a low friction rolling behavior. The distal portion 710 is attached to the rolling diaphragm 720 to create a low-friction dynamic mechanism. One end of the internal hollow tube 725 may be connected to a robotic medical system 750 at a first end portion of the connection mechanism 700 or through a medical system interface 760. The robotic medical system 750 may be presumed to be in a stationary position to provide a stationary platform or a medical system interface. A second end portion of the rolling diaphragm 720 or of the distal portion 710 may be connected to the airway management device 400, which includes the tube 410 inserted into the patient's mouth for the medical procedure. The rolling diaphragm 720 may be made of medical grade elastomers and/or plastics. In addition to the internal hollow tube 725, the distal portion 710 and the rolling diaphragm 720 may be hollow to allow passage of bronchial instruments.

In this configuration, the distal portion 710 may move, and the rolling diaphragm 720 may roll, along an entire length of the hollow tube 725 to provide flexibility in the longitudinal direction without, in the absence of adequate force, decoupling from the robotic medical system 750. In addition to the flexibility in the longitudinal direction, the hollow tube 725, the rolling diaphragm 720, and the distal portion 710 are flexible to provide 360° of freedom in the lateral direction. Critically, the flexibility of the hollow tube 725, the rolling diaphragm 720, and the distal portion 710 in the lateral direction may be a function of the respective diameters. The smaller the diameter, the higher the flexibility in the lateral direction, and the larger the diameter, the lower the flexibility in the lateral direction.

FIG. 8A also illustrates joint 730 at which the hollow tube 725 is connected to the medical system interface 760, and joint 740 at which the distal portion 710 is connected through an adaptor 770 to the airway management device 400 Both joints 730, 740 may be rigid connections about which the connection mechanism 700 flexes to provide multiple degrees of freedom in the lateral direction. Alternatively, both joints 730, 740 may be flexible connections that provide multiple degrees of freedom for flexibility in the lateral direction in addition to the flexibility provided by the connection mechanism 700. For example, the joint 730 may be movably connected to the medical system interface 760 to allow for movement of the joint 730 in multiple degrees of freedom in the lateral direction. In addition, joint 730 may allow the hollow tube 725 to be fixedly connected to the medical system interface 760 such that when decoupling is necessary, the medical system interface 760 is decoupled from the robotic medical system 750 instead of the connection mechanism 700 being decoupled from the medical system interface 760. Joints 730, 740 may be implemented using a mechanical lip structure similar to the mechanical lip structure discussed above. Alternatively, one or more of joints 730, 740 may be implemented using other mechanical and/or electromechanical mechanisms that may be activated by a sensor, as discussed in further detail later on.

Figure 8B:
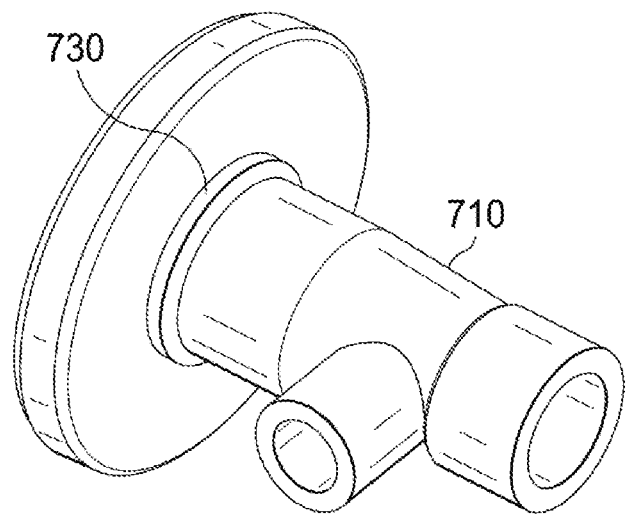
Figure 8C:
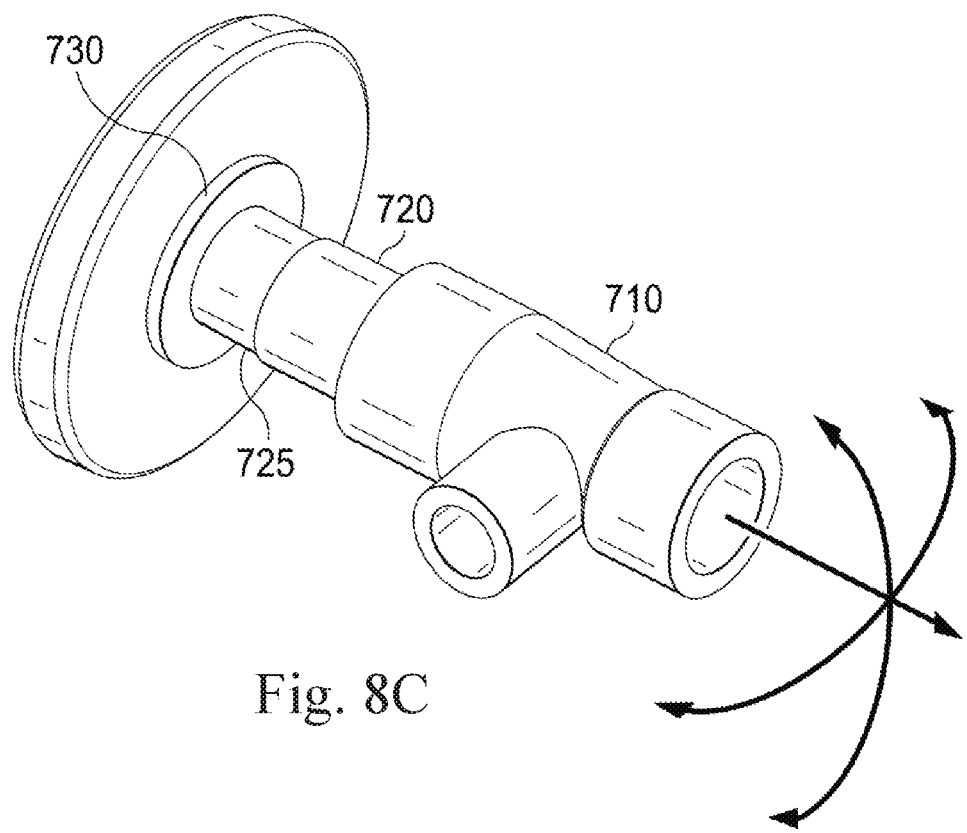

FIGS. 8B and 8C illustrate further details of the connection mechanism 700. In particular, FIG. 8B illustrates a contracted position of the connection mechanism 700 in which the rolling diaphragm 720 and the distal portion 710 are close to the medical system interface 760. FIG. 8C illustrates an extended position of the connection mechanism 700 in which the rolling diaphragm 720 and the distal portion 710 have moved along the entire length of the hollow tube 725 to provide flexibility in the longitudinal direction.

During the medical procedure, when the patient moves expectedly or unexpectedly to cause a minor displacement, or when inadvertent bumping of the robotic medical system causes a minor displacement, the connection mechanism 700 flexes as much as necessary in the lateral and longitudinal directions to accommodate the patient's motion. For example, the hollow tube 725, the rolling diaphragm 720, and the distal portion 710 and/or the mechanisms used for the joints 730, 740 flex as much as necessary to provide 360° of freedom in the lateral direction. Also, due to the minor displacement, the distal portion 710 may move relative to the robotic medical system. However, this minor displacement is accommodated by movement of the rolling diaphragm 720 and the distal portion 710 along the hollow tube 725 as much as necessary to provide flexibility in the longitudinal direction. In this way, the mechanical lip structures and/or other mechanical and electromechanical mechanisms prevent inadvertent decoupling of the connection mechanism 700 from either one of its connections at joints 730, 740 in the absence of adequate force.

Figure 8D:
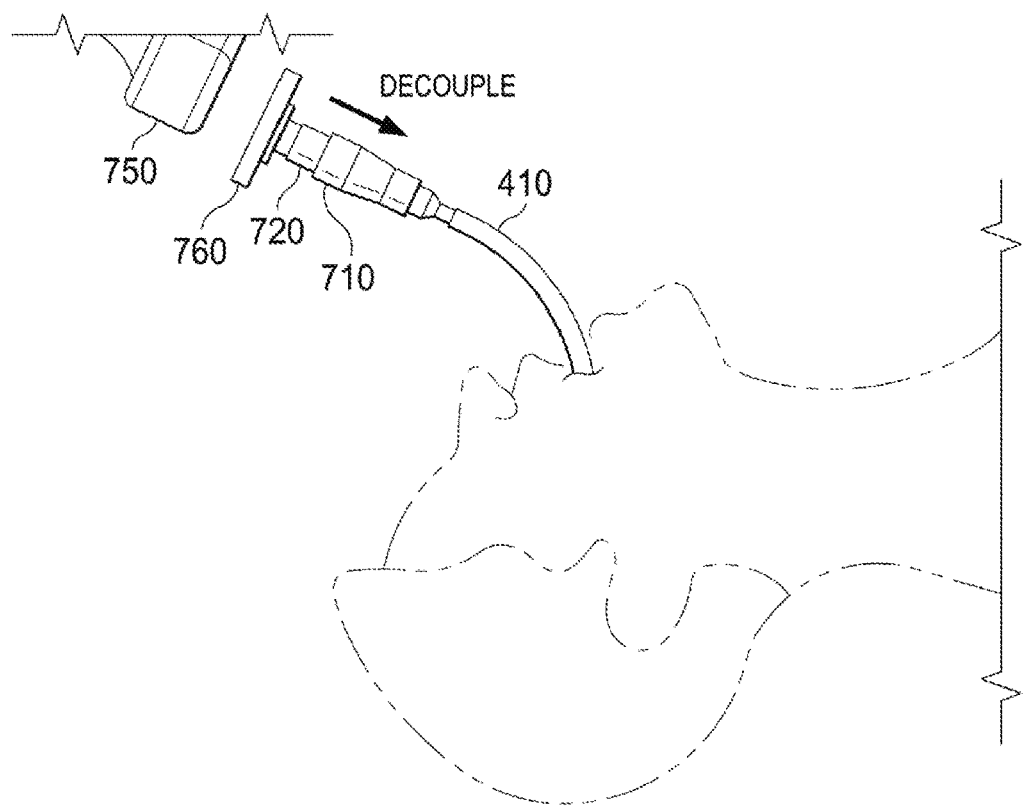

However, when the patient motion causes a major displacement, or when the unexpected or inadvertent bumping of the robotic medical system causes a significant relative displacement, which produces a significant force on the connection between the robotic medical system 750 and the airway management device 400, the mechanical lip structures and/or mechanical and electro-mechanical mechanisms enable decoupling of the robotic medical system 750 from the airway management device 400 as shown in, for example, FIG. 8D. In an exemplary embodiment, a sensing mechanism senses an amount of force at the connection and/or patient movement, and enables decoupling of the hollow tube 725 from the medical system interface 760 at joint 730 or decoupling of the medical system interface 760 from the robotic medical system 750. Additionally or alternatively, the sensing mechanism may enable decoupling of the distal portion 710 from the airway management device 400 at joint 740. In this way, when necessary, the connection mechanism 700 that connects the airway management device 400 to the robotic medical system 750 decouples the patient from the robotic medical system to ensure safety of the patient during the medical procedure.

Figure 9A:
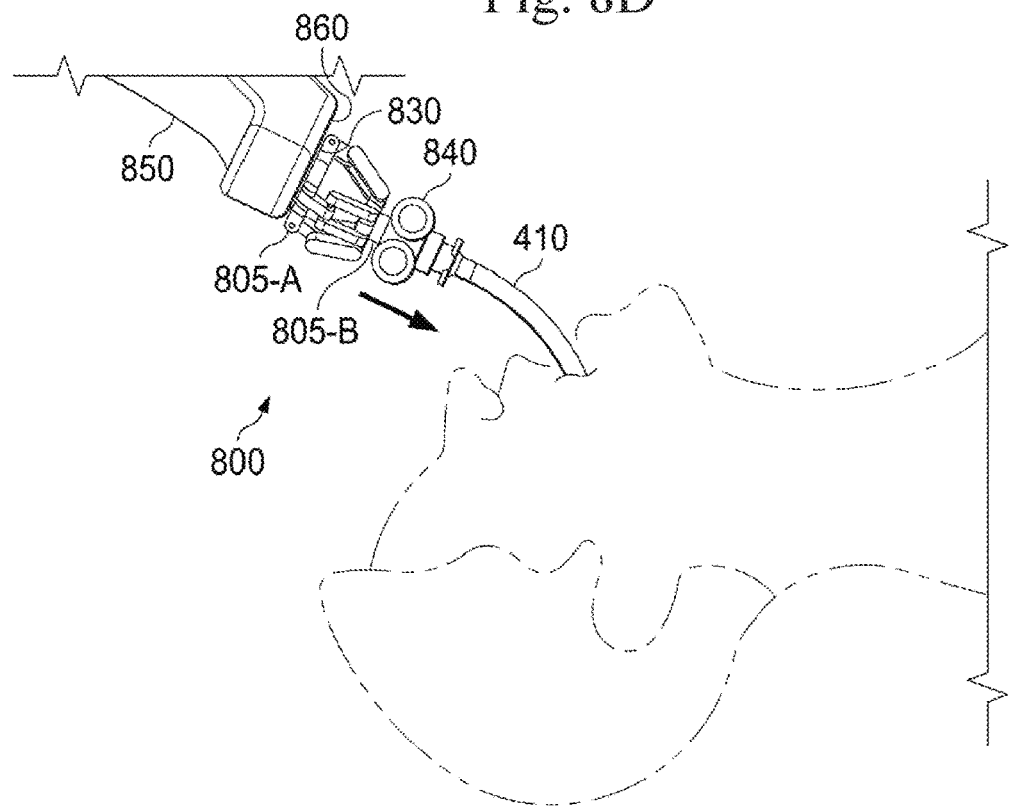

FIGS. 9A-D illustrate a kinematic connection mechanism 800 according to the present disclosure. As shown in FIG. 9A, the kinematic connection mechanism 800 may include a medial portion in the form of three flexible parallelogram linkages arranged in radial symmetry and each driven by a single rotary link. The kinematic connection mechanism 800 includes a multiple linkage mechanism, with, for example, three similar linkages 810-A, 810-B, 810-C having the same length and are parallel to each other. The multiple linkage mechanism connects two ends 805-A, 805-B of the parallelogram linkage. Each linkage 810-A, 810-B, 810-C includes two members movably attached to each other in a hinge configuration. Also, one of the members is movably attached to a first end 805-A of the parallelogram linkage in a hinge configuration, and the other member is movably attached to a second end 805-B of the parallelogram linkage in a hinge configuration.

The first end 805-A of the parallelogram linkage may be connected to a robotic medical system 850 through a medical system interface 860 at a first end portion of the kinematic connection mechanism 800. The robotic medical system 850 may be presumed to be in a stationary position to provide a stationary platform. The other end 805-B of the parallelogram linkage may be connected to the airway management device 400 at a second end portion, which includes the tube 410 inserted into the patient's mouth for the medical procedure. The components of the kinematic connection mechanism 800 may be made of medical grade thermoplastics, thermoset plastics, metals, or the like. The two ends 805-A, 805-B may include openings to allow passage of bronchial instruments for the procedure. In this configuration, the links 810-A, 810-B, 810-C may expand or contract to provide flexibility or kinematic freedom in the longitudinal direction without, in the absence of adequate force, decoupling from the robotic medical system 850. In addition to the flexibility or kinematic freedom in the longitudinal direction, the kinematics of the linkages allows for motion in two degrees of freedom in the lateral direction.

FIG. 9A also illustrates joint 830 at which the first end 805-A is connected to the medical system interface 860, and joint 840 at which the second end 805-B is connected to the airway management device 400 through an adaptor 870. Both joints 830, 840 may be rigid connections about which the kinematic connection mechanism 800 moves to provide multiple degrees of freedom in the lateral direction. Alternatively, both joints 830, 840 may be flexible connectors that provide multiple degrees of freedom for flexibility in the lateral direction in addition to the flexibility provided by the kinematic connection mechanism 800. For example, the joint 830 may be movably connected to the medical system interface 860 to allow for movement of the joint 830 in multiple degrees of freedom in the lateral direction. In addition, joint 830 may allow the first end 805-A to be fixedly connected to the medical system interface 860 such that when decoupling is necessary, the medical system interface 860 is decoupled from the robotic medical system 850 instead of the first end 805-A being decoupled from the medical system interface 860. Joints 830, 840 may be implemented using a mechanical lip structure similar to the mechanical lip structure discussed above. Alternatively, one or more of joints 830, 840 may be implemented using other mechanical and/or electromechanical mechanisms that may be activated by a sensor, as discussed in further detail later on.

Figure 9B:
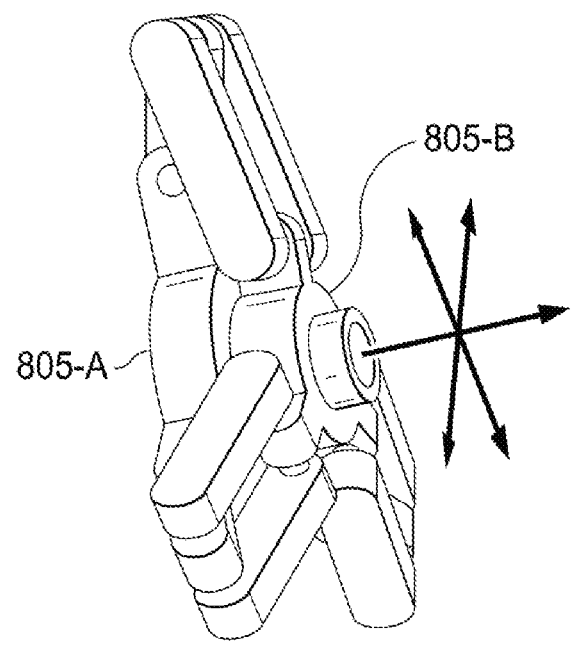
Figure 9C:
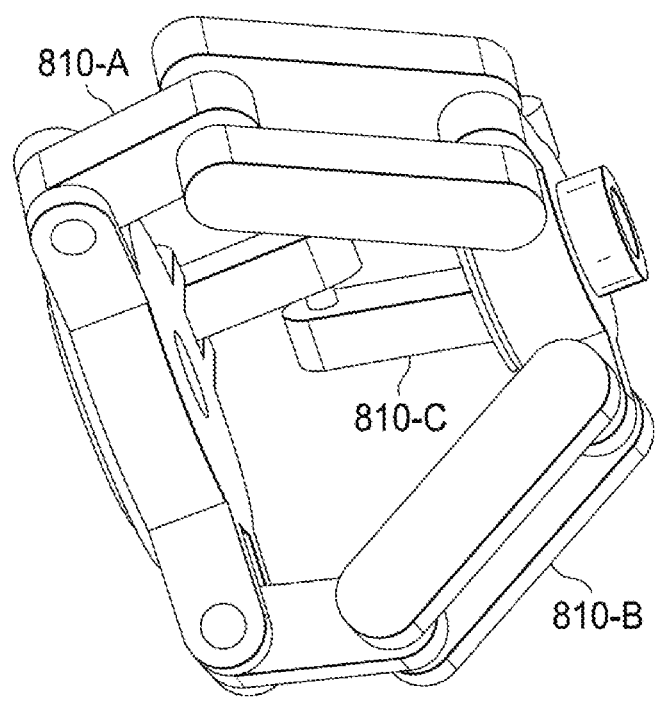

FIGS. 9B and 9C illustrate further details of the kinematic connection mechanism 800. In particular, FIG. 9B illustrates a contracted position of the kinematic connection mechanism 800 in which the linkages 810-A, 810-B, 810-C are in a compressed position close to the medical system interface 860. FIG. 9C illustrates an extended position of the kinematic connection mechanism 800 in which the linkages 810-A, 810-B, 810-C are extended to provide flexibility in the longitudinal direction.

During the medical procedure, when the patient moves expectedly or unexpectedly to cause a minor displacement, or when inadvertent bumping of the robotic medical system causes a minor displacement, the kinematic connection mechanism 800 moves as much as necessary in the lateral and longitudinal directions to accommodate the patient's motion, limiting the amount of force resolved in the connections at joints 830 and 840. In this way, the mechanical lip structures and/or the mechanical and electromechanical mechanisms prevent inadvertent decoupling of the kinematic connection mechanism 800 from either one of its connections at joints 830, 840 in the absence of adequate force.

Figure 9D:
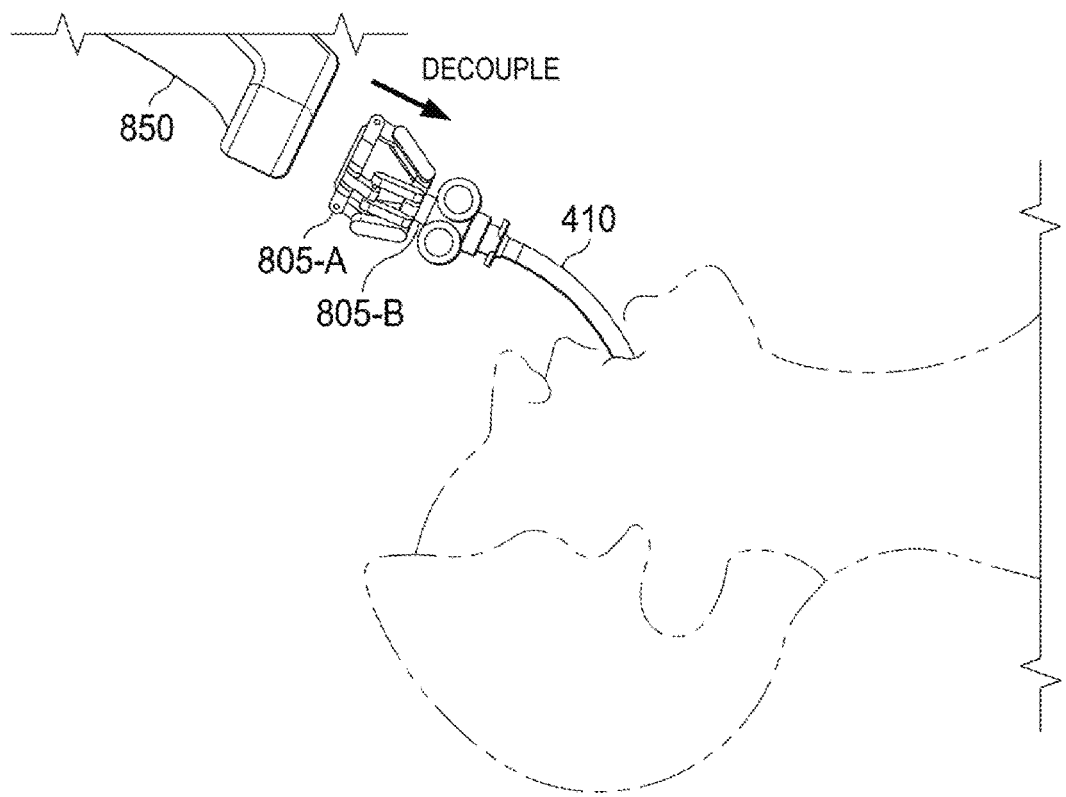

However, when the patient motion causes a major displacement, or when the unexpected or inadvertent bumping of the robotic medical system causes a significant relative displacement, which produces a significant force on the connection between the robotic medical system 850 and the airway management device 400, the mechanical lip structures and/or mechanical and electro-mechanical mechanisms enable decoupling of the robotic medical system 850 from the airway management device 400 as shown in, for example, FIG. 9D. In an exemplary embodiment, a sensing mechanism senses an amount force at the connection and/or patient movement, and enables decoupling of the first end 805-A from the medical system interface 860 at joint 830 or decoupling of the second end 805-B from the airway management device 400 at joint 840. Additionally or alternatively, the sensing mechanism may enable decoupling of the medical system interface 860 from the robotic medical system 850. In this way, the kinematic connection mechanism 800 that connects the airway management device 400 to the robotic medical system 850 decouples the patient from the robotic medical system to ensure safety of the patient during the medical procedure.

Figure 10A:
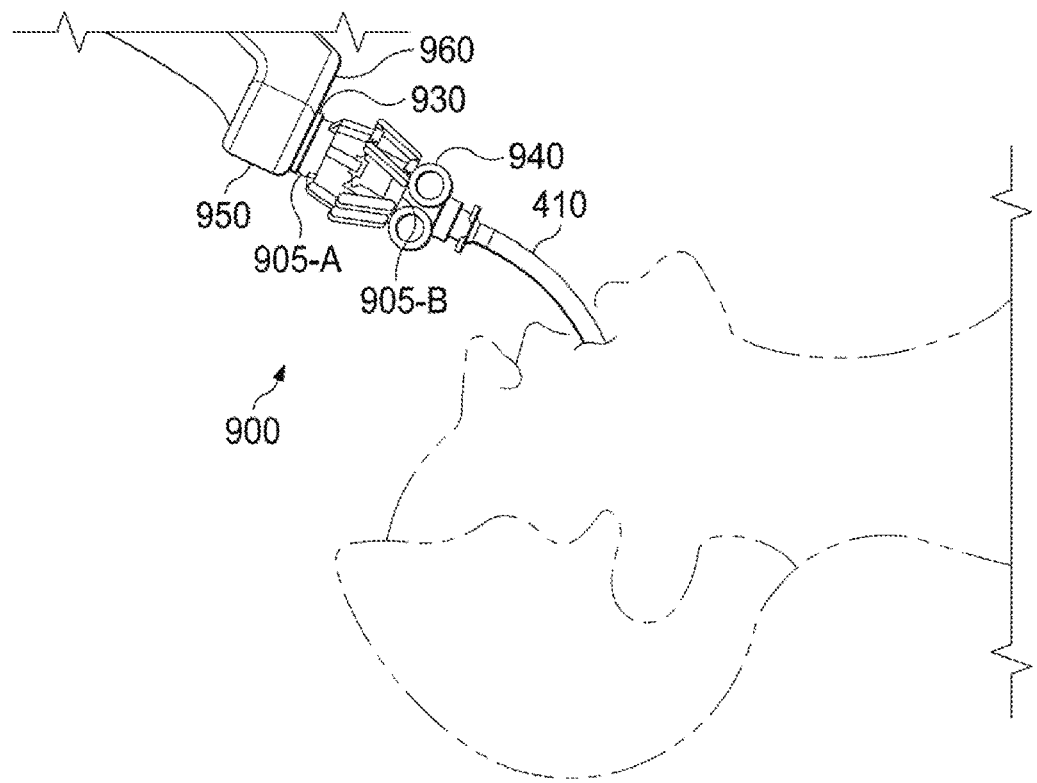

FIGS. 10A-D illustrate a kinematic connection mechanism 900 according to the present disclosure. As shown in FIG. 10A, the kinematic connection mechanism 900 may include a medial portion in the form of three parallelogram linkages arranged in radial symmetry, each driven by a single rotary link similar to the parallelogram linkages of the kinematic connection mechanism 800 except each pinned revolute joint has now been replaced by a flexure living hinge construction consisting of a thin portion of material that provides a localized region of high elastic flexibility. This region behaves mechanically equivalent to a revolute joint. The flexure linkage includes a multiple linkage mechanism, with, for example, three linkages 910-A, 910-B, 910-C that have the same length and are parallel to each other. The multiple linkage mechanism connects two ends 905-A, 905-B of the flexure linkage. Each linkage 910-A, 910-B, 910-C includes a base driving member that is connected to 905-A by means of a living hinge joint, and a parallelogram structure that connects the driving member to 905-B in both cases by a living hinge joint. The two structures may be formed of thin medical grade plastic material.

The first end 905-A of the flexure linkage may be connected to a robotic medical system 950 through a medical system interface 960 at a first end portion of the kinematic connection mechanism 900. The robotic medical system 950 may be presumed to be in a stationary position to provide a stationary platform. The second end 905-B of the flexure linkage may be connected to the airway management device 400 at a second end portion of the kinematic connection mechanism, which includes the tube 410 inserted into the patient's mouth for the medical procedure. The components of the kinematic connection mechanism 900 may be made of medical grade materials such as polyurethane, polyvinyl chloride, flexible PVC, or the like. The two ends 905-A, 905-B may include openings to allow passage of bronchial instruments for the procedure. In this configuration, the linkages 910-A, 910-B, 910-C may expand or contract to accommodate motion or provide flexibility in the longitudinal/lateral direction without, in the absence of adequate force, decoupling from the robotic medical system 950.

FIG. 10A also illustrates joint 930 at which the first end 905-A is connected to the medical system interface 960, and joint 940 at which the second end 905-B is connected to the airway management device 400 through an adaptor 970. Both joints 930, 940 may be rigid connections about which the kinematic connection mechanism 900 moves to provide multiple degrees of freedom in the lateral direction. Alternatively, both joints 930, 940 may be flexible connections that provide multiple degrees of freedom for flexibility in the lateral direction in addition to the flexibility provided by the kinematic connection mechanism 900. For example, the joint 930 may be movably connected to the medical system interface 960 to allow for movement of the joint 930 in multiple degrees of freedom in the lateral direction. In addition, joint 930 may allow the first end 905-A to be fixedly connected to the medical system interface 960 such that when decoupling is necessary, the medical system interface 960 is decoupled from the robotic medical system 950 instead of the first end 905-A being decoupled from the medical system interface 960. Joints 930, 940 may be implemented using a mechanical lip structure similar to the mechanical lip structure discussed above. Alternatively, one or more of joints 930, 940 may be implemented using other mechanical and/or electromechanical mechanisms that may be activated by a sensor, as discussed in further detail later on.

Figure 10B:
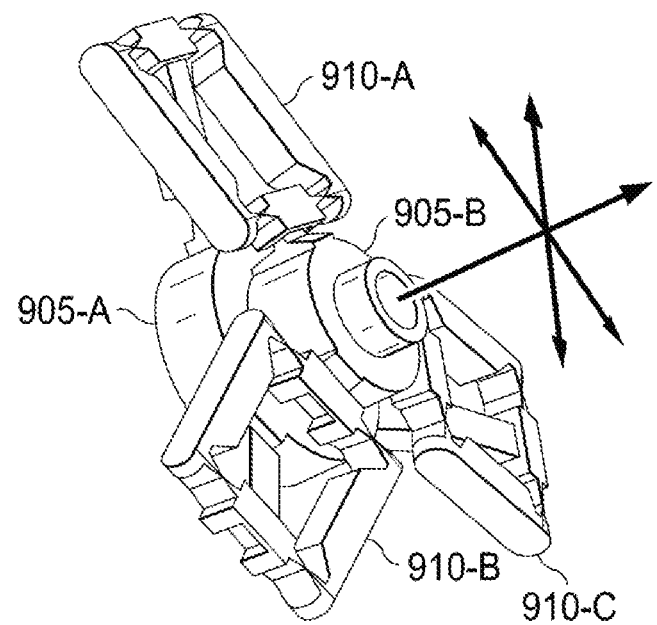
Figure 10C:
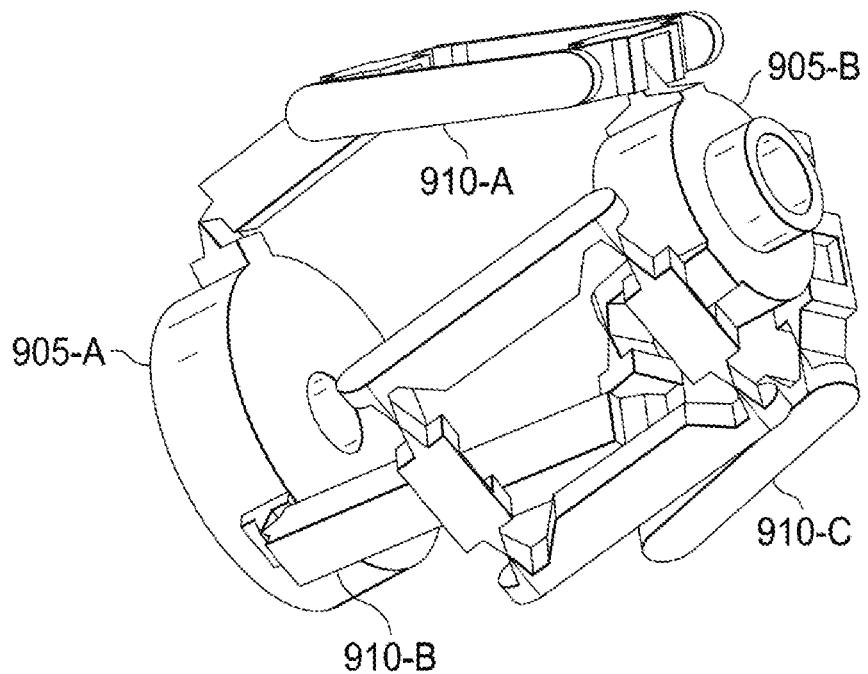

FIGS. 10B and 10C illustrate further details of the kinematic connection mechanism 900. In particular, FIG. 10B illustrates a compressed position of the kinematic connection mechanism 900 in which the linkages 910-A, 910-B, 910-C are in a folded position close to the medical system interface 960. FIG. 10C illustrates an extended position of the kinematic connection mechanism 900 in which the linkages 910-A, 910-B, 910-C are extended through their hinge configurations to provide flexibility in the longitudinal direction.

During the medical procedure, when the patient moves expectedly or unexpectedly to cause a minor displacement, or when inadvertent bumping of the robotic medical system causes a minor displacement, the kinematic connection mechanism 900 moves to provide some flexible movement in the lateral and longitudinal directions to accommodate the patient's motion limiting the amount of force resolved by the joints 930 and 940. In this way, the mechanical lip structures and/or the mechanical and electromechanical mechanisms prevent inadvertent decoupling of the kinematic connection mechanism 800 from either one of its connections at joints 930, 940 in the absence of adequate force.

Figure 10D:
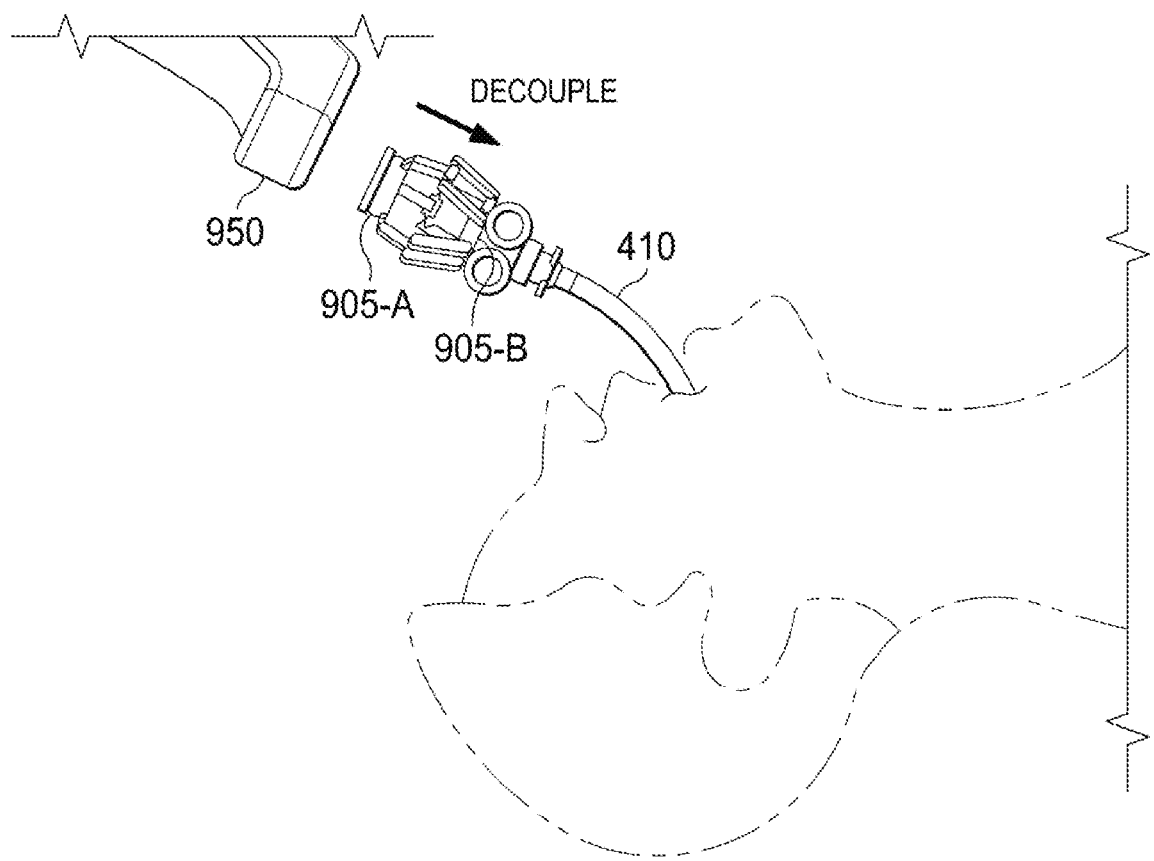

However, when the patient motion causes a major displacement, or when the unexpected or inadvertent bumping of the robotic medical system causes a significant relative displacement, which produces a significant force on the connection between the robotic medical system 950 and the airway management device 400, the mechanical lip structures and/or mechanical and electro-mechanical mechanisms enable decoupling of the robotic medical system 950 from the airway management device 400 as shown in, for example, FIG. 10D. In an exemplary embodiment, a sensing mechanism senses the significant force at the connection and/or patient movement, and enables decoupling of the first end 905-A from the medical system interface 960 at joint 930 or decoupling of the medical system interface 960 from the robotic medical system 950. Additionally or alternatively, the sensing mechanism may enable decoupling of the second end 905-B from the airway management device 400 at joint 940. In this way, the kinematic connection mechanism 900 that connects the airway management device 400 to the robotic medical system 950 decouples the patient from the robotic medical system to ensure safety of the patient during the medical procedure.

Now, the systems and methods that provide controlled retention and release of the flexibly connected elements during the medical procedure will be discussed. These systems and methods ensure patient safety during the medical procedure by decoupling the patient from the robotic medical system through release of the connection mechanism between the robotic medical system and the airway management device. In addition to ensuring patient safety, the various mechanical and electro-mechanical mechanisms assist in avoiding unnecessary release of the connection mechanism when patient motion causes only a minor displacement. In this way, unnecessary delay or interruption in conducting the medical procedure is avoided.

As described in detail below, various mechanical and electro-mechanical mechanisms may be used to decouple, when necessary, the connection mechanisms between the robotic medical system and the airway management device. These mechanisms may possess the ability to reliably retain, and automatically and quickly release the connection mechanism between the robotic medical system and the airway management device. The automatic quick release is critical because it may avoid the need for effective human intervention in response to developments that may endanger the safety of the patient and may provide for faster response than reliance on human intervention. Also, these mechanisms may include a sensing mechanism that senses parameters associated with the connection mechanism, and automatically actuates the decoupling of the connection mechanism based on a comparison of the sensed parameters with predetermined threshold parameters.

For mechanical mechanisms, when the patient motion causes a major displacement, it produces a significant force on the connection between the robotic medical system and the airway management device, and the mechanical mechanisms enable decoupling of the coupling. In this way, the connection mechanism that connects the airway management device to the robotic medical system decouples the patient from the robotic medical system to ensure safety of the patient during the medical procedure. With mechanical mechanisms, the mechanism for retention of the connection between the couplings is mechanical and also the mechanism for decoupling the couplings is mechanical.

In various embodiments, a mechanical mechanism such as the lip structure illustrated in FIG. 6B may be used to implement the above couplings. In the case of the mechanical lip structure, a mechanical force larger than the force that the lip structure is designed to handle will serve to decouple the connection. For example, as shown in FIG. 6B, a mechanical force larger than the force that the lip structure between the first flexible tube 510 and the second flexible tube 520 is designed to handle will serve to decouple the connection between the first flexible tube 510 in the second flexible tube 520.

FIG. 13 illustrates another mechanical mechanism 1200 according to an embodiment of the present disclosure. The mechanical mechanism 1200 includes implementing at least one of the above couplings using connector portions such as permanent magnets 1210, 1220. As discussed below with respect to FIG. 12, connector portions may also be electromagnetic cores 1310, 1320. In various embodiments, connector portions 1210, 1220 may be attached to two ends of a coupling (e.g., robotic medical system and medical system interface, medical system interface and an end of a connection mechanism, etc.). When permanent magnets are used, the permanent magnets of connector portions 1210, 1220 generate their respective, persistent magnetic fields to couple the two ends of the coupling. In various embodiments, only one of the connector portions may include a permanent magnet, while the other connector portion may include a component made of magnetic material to enable the coupling. For the mechanism 1200, a force large enough to overcome the strength of or forces generated by the respective magnetic fields of the magnets of the connector portions 1210, 1220 may decouple the connection between the two couplings. In addition, for decoupling, the strength of forces generated by the respective magnetic fields of the magnets of the connector portions 1210, 1220 may be nullified by providing electrical coils around the magnets. For example, current may be passed through the electrical coils in a direction such that a magnetic field is produced that opposes or nullifies the magnetic fields produced by the permanent magnets of the connector portions 1210, 1220. In various embodiments, one connector portion 1210 may be a permanent magnet while the other connector portion 1220 may be an electromagnetic component (e.g., steel alloy). In such cases, the electric coils may be provided around the other connector portion 1220 to nullify the magnetic field produced by the permanent magnet of connector portion 1210. In various embodiments, a separate electromagnetic component (e.g., steel alloy) may be placed in the vicinity of two permanent magnets of the connector portions 1210, 1220 to decouple the permanent magnets from each other by nullifying their magnetic fields through passage of current, as discussed above.

The present disclosure also contemplates use of electromechanical mechanisms in which the mechanism for retention of the connection between the couplings is mechanical, but the mechanism for decoupling the couplings is electrical. In these electro-mechanical mechanisms, the connection mechanisms may be designed to have breakaway parameters (e.g., force, pressure, displacement) larger than desired predetermined threshold parameters (e.g., force, pressure, displacement) at which a sensing mechanism 1000 (discussed below) actuates a decoupling mechanism 1050 (discussed below). This critically allows ensuring that the couplings do not unnecessarily break away during the medical procedure. Rather, the decoupling of the couplings is controlled by actuation through the decoupling mechanism 1050, as discussed below. FIG. 11 illustrates a block diagram of the sensing mechanism 1000 according to an embodiment of the present disclosure. The sensing mechanism 1000 includes a sensor 1010 strategically placed on or around the connection mechanism between a robotic medical system and an airway management device. The sensor 1010 may be electronically connected through a medium 1020 to a processor 1030 that is coupled to a memory 1040. The medium 1020 may electronically connect the sensor 1010 to the processor 1030 through a physical medium such as wires, or through a wireless medium utilizing wireless signals such as radiofrequency (RF) signals. The processor 1030 may be electronically connected, through medium 1060, to a decoupling mechanism 1050 that actuates decoupling of the connection mechanism. Similar to medium 1020, medium 1060 may be a wired or wireless medium.

In one embodiment, the sensor 1010 may be strategically placed and be configured to sense and/or measure a physical force or pressure exerted on or around the connection mechanism between the robotic medical system and the airway management device. The sensor 1010 may also be configured to generate and provide electrical signals regarding a measurement of the sensed force/pressure to the processor 1030 over the medium 1020. In an exemplary embodiment, the sensor 1010 may be configured to provide a sensed magnitude of the force/pressure on or around the connection mechanism. As one example, the sensor 1010 may be a force transducer configured to sense force/pressure on or around the connection mechanism between the robotic medical system and the airway management device, and generate and provide electrical signals with respect to sensed force. The processor 1030 may be configured to receive the sensed magnitude of the force/pressure over the medium 1020. Further, the processor 1030 may be configured to retrieve a predetermined threshold magnitude of force/pressure from the memory 1040. The processor 1030 may compare the received sensed magnitude with the retrieved threshold magnitude. Based on the results of the comparison, the processor 1030 may actuate the decoupling mechanism 1050 to decouple the connection mechanism provided between the robotic medical system and the insertion aid. For example, when the received magnitude of the sensed force is greater or equal to the threshold magnitude of force, the processor 1030 may generate and provide electrical signals to the decoupling mechanism 1050 over the medium 1060 to decouple the connection mechanism.

In various embodiments, the sensor 1010 may provide the processor 1030 with parameters in addition to the sensed force/pressure. For example, the sensor 1010 may be configured to sense and/or measure the rate of change of force/pressure, and generate and provide electrical signals informing the processor 1030 of the sensed rate of change of force/pressure. The processor 1030 may then compare the received rate of change of force/pressure with the retrieved rate of change of force/pressure from the memory 1040, and actuate, if necessary, the decoupling mechanism 1050 based on the results of the comparison. Similarly, in various embodiments, the sensor 1010 may be configured to sense an amount of force/pressure in a specific direction, and provide the same to the processor 1030. For example, the sensor 1010 may sense force/pressure with respect to orientation of the robotic medical system or the patient in relation to the connection mechanism between the robotic medical system and the airway management device. The processor 1030 may then compare the sensed amount of force/pressure in the specific direction with the retrieved amount of force/pressure in the specific direction from the memory 1040, and actuate, if necessary, the decoupling mechanism 1050 based on the results of the comparison.

Such decoupling criteria would critically allow the sensing mechanism 1000 to not unnecessarily actuate the decoupling mechanism.

In an alternative embodiment, the sensor 1010 may be strategically placed to measure a displacement of a patient from an initial position during the medical procedure. For example, the sensor 1010 may be strategically placed on the patient's chest or other body part such as the patient's head that may allow proper measurement of the patient's displacement. The sensor 1010 may also be strategically placed on the patient pad on which the patient is lying down. The sensor 1010 may be configured to provide electrical signals regarding a measurement of the sensed displacement of the patient from the initial position to the processor 1030 over the medium 1020. For instance, the sensor 1010 may be configured to provide a sensed magnitude of displacement. The processor 1030 may be configured to receive the sensed magnitude of the displacement over the medium 1020. Further, the processor 1030 may be configured to retrieve a predetermined threshold magnitude of displacement from the memory 1040. The processor 1030 may compare the received sensed magnitude of displacement with the retrieved threshold magnitude of displacement, and based on the results of the comparison, the processor 1030 may actuate the decoupling mechanism 1050 to decouple the connection mechanism provided between the robotic medical system and the insertion aid. For instance, when the received sensed magnitude is greater or equal to the threshold magnitude, the processor 1030 may generate and provide electrical signals to the decoupling mechanism 1050 over the medium 1060 to decouple the connection mechanism.

As one example, the sensor 1010 may include an accelerometer placed on the body (e.g., chest, head) of the patient to sense patient motion, including, in some examples, initial stages of the patient motion before the patient motion propagates through the patient's body to the airway management device. The accelerometer may include a high pass filter configured to sense high-frequency signals produced when, for example, the patient coughs. In this way, the accelerometer is configured to determine patient motion very early by sensing these high-frequency signals. As another example, the sensor 1010 may be a myoelectric sensor including electrodes placed on the body of the patient or implanted within the body of the patient. A myoelectric sensor may be configured to sense electrical signals within the patient's body that initiate muscle movement, and therefore motion, in the patient's body. This way, the myoelectric sensor is configured to determine patient motion very early by sensing these electrical signals. This may allow the processor to detect the onset of sudden patient motion such as a cough or other change in the patient's position, and, if necessary, actuate the decoupling mechanism 1050. A myoelectric sensor, by virtue of its placement proximate to the patient's body, and may allow earliest detection of onset of patient motion. Further examples of the sensor 1010 may include a band extensometer placed to surround the chest of the patient, a fiber-optic patient pad provided with an accelerometer or a fiber sensing mechanism, and other electro-mechanical displacement sensors to sense displacement in the patient's body due to patient motion.

In various embodiments, the sensor 1010 may provide the processor 1030 with parameters in addition to the sensed displacement. For example, the sensor 1010 may be configured to sense and/or measure the rate of change of displacement, and generate and provide electrical signals informing the processor 1030 of the sensed rate of change of displacement. The processor 1030 may then compare the received rate of change of displacement with the retrieved rate of change of displacement from the memory 1040, and actuate, if necessary, the decoupling mechanism 1050 based on the results of the comparison. Similarly as discussed above, such decoupling criteria would critically allow the sensing mechanism 1000 to not unnecessarily actuate the decoupling mechanism.

In summary, the sensing mechanism 1000 may actuate decoupling based on, for example, a maximum force/pressure/displacement, and/or rate of change of maximum force/pressure/displacement, and/or a maximum force/pressure/displacement in a specific direction. In some cases, both factors of force and rate of change of force may increase the likelihood of injury to the patient. In such cases, the sensing mechanism 1000 may include multiple sensors 1010, with one sensor sensing parameters associated with the force/pressure and the rate of the change of force/pressure and another sensor sensing parameters associated with patient displacement. The sensing mechanism 1000 may be programmed to include (e.g., in memory 1040) a predetermined weighted sum combination of the outputs from the multiple sensors to actuate the decoupling mechanism 1050. The predetermined weighted sum combination may be variable, and can be adjusted prior to starting the medical procedure based on factors such as the weight and/or height and/or body mass index of the patient, and the like. Further, the predetermined weighted sum combination may be dynamically adjusted during the medical procedure based on change in factors associated with performance of the medical procedure. For example, the patient might exhibit discomfort during the medical procedure, and the predetermined weighted sum may need to be dynamically adjusted to accommodate movements related to comforting the patient.

Decoupling criteria for the sensing mechanism 1000 may include one or more of initial rate of change (the onset), magnitude, direction(s), or time history of a force sensed by a sensor 1010 such as a single or multi-axis force transducer. The criteria may also include one or more of initial rate (onset), magnitude, direction, or time history of acceleration sensed by a sensor 1010 such as an accelerometer or a 6-axis inertial measurement unit (IMU) attached to the patient. In various embodiments, the criteria may include onset, pattern, and/or history of myoelectric signals. Along with displacement or velocity sensed in a given direction, the criteria may also include a predetermined weighted sum of two or more of the above measures or a weighting customized for specific operating conditions in accordance with characteristics of the patient (e.g. weight, height, BMI, etc.).

In this case, the processor 1030 may be configured to receive electrical signals from the multiple sensors, and calculate the sensed weighted sum combination based on the electrical signals received from the multiple sensors. The processor 1030 may then compare the calculated weighted sum combination with the retrieved weighted sum combination from, for example, the memory 1040. Based on the results of the comparison, as discussed above, the processor 1030 may actuate the decoupling mechanism 1050. The use of the weighted sum combination critically allows the processor 1030 to determine whether to actuate the decoupling mechanism 1050 in situations where the sensed displacement may warrant actuation of the decoupling mechanism 1050 but the sensed force/pressure may not warrant actuation of the decoupling mechanism 1050, and vice versa. In these situations, the use of the weighted sum combination allows the processor 1030 to properly determine actuation of the decoupling mechanism 1050 to ensure patient safety.

The sensing mechanism 1000 may work in combination with mechanical and electro-mechanical mechanisms to decouple, when necessary, the connection mechanism between the robotic medical system and the airway management device. With respect to the connection mechanisms discussed above in connection with FIGS. 5-10, the decoupling may take place at one or more of the couplings including the connection between the robotic medical system and the medical system interface, and/or at the joint connecting the medical system interface to the connection mechanism, and/or at connections within the connection mechanism, and/or at the joint connecting the connection mechanism to the airway management device. At least one of these couplings may be implemented using the various mechanical and electro-mechanical mechanisms that function in combination with the sensing mechanism 1000 to decouple the connection mechanism.

FIG. 12A illustrates a method 1100 according to an embodiment of the present disclosure. The method 1100 starts at a process 1105. At a process 1110, a first connector portion may be attached to the robotic medical system. In various embodiments, the first connector portion may be associated with a first end of the several different couplings discussed above. At a process 1115, a second connector portion may be attached to an anatomic orifice device. In various embodiments, the second connector portion may be associated with a second end of the several different couplings discussed above. At a process 1120, the first connector portion may be connected to the second connector portion. For example, the first connector portion may be connected to the second connector portion during the medical procedure on a patient to whom the anatomic orifice device is to be decoupled. At a process 1125, the sensing mechanism may sense a parameter associated with motion of the patient relative to the robotic medical system. In an optional process, the sensing mechanism may compare the received value of the sensed parameter with a retrieved predetermined threshold value of the sensed parameter, and then activate disconnection of the first connector portion from the second connector portion. At a process 1130, the sensing mechanism may disconnect the first connector portion from the second connector portion based on the sensed parameter. The method stops at a process 1135.

FIG. 12B illustrates a method 1150 performed by the sensing mechanism 1000 according to an embodiment of the present disclosure. The method 1150 starts at a process 1155. At a process 1160, the sensing mechanism 1000 senses a parameter associated with the connection mechanism. At a process 1165, the sensing mechanism 1000 generates and provides electrical signals indicative of a value of the sensed parameter. In an exemplary embodiment, the sensor 1010 of the sensing mechanism 1000 may sense the parameter associated with the connection mechanism, and generate and provide electrical signals indicative of the value of the sensed parameter to the processor 1030. At a process 1170, the sensing mechanism 1000 may compare the received value of the sensed parameter with a retrieved predetermined threshold value of the sensed parameter. At a process 1175, based on the results of the comparison, the sensing mechanism 1000 may actuate the decoupling mechanism 1050 to decouple the robotic medical system from the airway management device. In an exemplary embodiment, the processor 1030 may receive the electrical signals indicating the value of the sensed parameter, and retrieve a predetermined threshold value of the sensed parameter from the memory 1040. The processor 1030 may compare the received value of the sensed parameter and a retrieved predetermined threshold value, and based on the results of the comparison, the processor 1030 may actuate the decoupling mechanism 1050 to decouple the robotic medical system from the airway management device. The method stops at a process 1180.

FIG. 14 illustrates an electro-mechanical mechanism 1300 according to an embodiment of the present disclosure. The electro-mechanical mechanism 1300 includes implementing at least one of the above couplings using electro-magnets, magnets provided with electric coils. As shown in FIG. 14, electric coils 1330, 1340 may be provided via large number of closely spaced turns of wire wound around magnetic cores 1310, 1320, which may be made from a ferromagnetic material such as iron. In various embodiments, only one of the connector portions may include the electromagnet, while the other connector portion may include a component made of magnetic material to enable the coupling. In an electromagnet, the magnetic field is produced when the electric coils 1330, 1340 are excited by an electric current. Conversely, the magnetic field is nullified when the electric current in the electric coils 1330, 1340 is turned off. The electric current in the electric coils 1330, 1340 may be controlled by actuation through the decoupling mechanism 1050. The decoupling mechanism 1050 may include circuitry to turn on and turn off the electric current in the electric coils 1330, 1340.

When provided with electrical current by the decoupling mechanism 1050, the excited electrical coils produce respective magnetic fields in the magnetic cores 1310, 1320. When the magnetic fields are produced, the magnetic cores 1310, 1320 are coupled to each other under the force of the magnetic fields. However, when the decoupling mechanism 1050 disables the electrical currents in the electric coils 1330, 1340, the respective magnetic fields are nullified. When the magnetic fields are nullified, the magnetic cores 1310, 1320 freely decouple from each other. In this way, when necessary, the decoupling mechanism 1050 decouples the magnetic cores 1310, 1320, and allows the robotic medical system to disconnect from the patient to ensure patient safety during the medical procedure.

The present disclosure also contemplates including a spring mechanism between the robotic medical system and the airway management device for automatic reconnection of decoupled couplings. FIG. 15 illustrates a spring mechanism 1400 according to an embodiment of the present disclosure. The spring mechanism 1400 enables re-coupling of couplings that have been decoupled. In various embodiments, the spring mechanism 1400 is maintained in addition to the connection mechanisms discussed above. When the expected or unexpected motion (e.g., coughing) of the patient, that leads to the decoupling of the couplings, is complete, the spring mechanism may enable automatic coupling of the decoupled connection mechanism so that the medical procedure may be continued. For example, as shown in FIG. 15, the spring mechanism 1400 is configured to enable automatic re-coupling of decoupled magnets 1410, 1420 that are attached to the robotic medical system and the medical system interface, respectively.

In various embodiments, the spring mechanism 1400 may be electrically activated upon completion of the expected or unexpected patient motion or after a predetermined time thereafter. FIG. 16 illustrates a block diagram of system 1500 according to an embodiment of the present disclosure. The system 1500 (e.g., sensing mechanism) includes the previously discussed sensor 1010, medium 1020, processor 1030, memory 1040, decoupling mechanism 1050, and medium 1060. In addition, system 1500 includes a medium 1520 that electrically connects the processor 1030 to the spring mechanism 1400. Medium 1520 may be similar to the previously discussed mediums 1020, 1060.

Upon completion of the expected or unexpected patient motion that led to the decoupling of the connection mechanism, the sensor 1010 may continue to sense the parameters, and provide electrical signals regarding a measurement of the same to the processor 1030. The processor 1030 may compare the received parameter value with a retrieved predetermined parameter value from the memory 1040. Based on the results of the comparison, when the processor 1030 determines that the received parameter value is lower than the predetermined parameter value, the processor 1030 actuates the spring mechanism 1400 to automatically couple the decoupled couplings. In various embodiments, the processor 1030 may actuate the spring mechanism 1400 when the received parameter value is lower than the predetermined parameter value by a predetermined amount.

FIG. 17 illustrates couplings between an elongate device 1600 (e.g., elongate device 202 of FIG. 2) and other components via a device port 1602. For example, a handle assembly 1604 of a medical tool to be inserted through the catheter may be coupled at the device port 1602. Alternatively, a suction adapter 1606 may be coupled to the device port 1602 to provide a connection between a proximal end of the elongate device 1600 and a vacuum source used to remove debris from the elongate device 1600. The device port 1602 is coupled to or integral with a device housing 1608. The device housing 1608 is coupled to a proximal end of the elongate device 1600. The elongate device 1600 extends through an instrument carriage 1610 (e.g., carriage 306 of FIGS. 3A and 3B). The instrument carriage 1610 moves along an insertion stage 1612 (e.g., insertion stage 308 of FIGS. 3A and 3B) which may be part of a surgical manipulator (e.g., a teleoperational manipulator). Other types of medical tools, including for example an image capture probe 1614 or an ablation instrument may be connected to device port 1602 to access the elongate device 1600 (e.g., be received within a lumen of the elongate device 1600). The image capture probe 1614 may be communicatively coupled to the carriage 1610 by a cable 1616 that conveys power, image data, instruction signals or the like. The image capture probe 1614 may also be coupled through the carriage 1610 to a fluid source that may convey a cleaning fluid via a conduit 1618 to the probe 1614.

FIG. 18 illustrates the suction adapter 1606 in greater detail. The adapter 1606 includes a cannulated body 1650 with an end 1654 and an end 1656. A flow passage 1652 extends through the body 1650 between the ends 1654 and 1656. The body 1650 may be tapered from a wider diameter at the end 1654 to a smaller diameter at the end 1656. The body 1650 may be formed from a flexible and/or elastomeric material. The end 1656 includes a set of barbs 1658 that may provide a sealing attachment to a suction source such as a vacuum hose (not shown). The end 1654 may couple to the device port 1602. The interior of the passage 1652 at the end 1654 may be smooth to facilitate an easy slide-on/off coupling with the device port 1602. A port 1660 extends laterally from the body 1650 and provides a passage 1662 in communication with the passage 1652.

In use, before another instrument is coupled to the catheter or after another instrument has been removed from the catheter, the suction adapter 1606 may be coupled to the port 1660 and a vacuum source applied to the end 1656 to remove fluids and debris that may have become lodged in the catheter. This clearing of fluid and debris may provide a clear catheter working lumen for insertion of later instruments such as a biopsy tool. The user may manually regulate the air flow through passage 1662 by placing a finger over the port 1660, thus controlling suction through the adapter 1606.

Further examples of a connection mechanism are shown in FIGS. 19A and 19B, which illustrate a connection mechanism 1850 according to an embodiment of the present disclosure. The connection mechanism 1850 may rotatably or swivelly (e.g., rotateable about an axis) couple to a mating bracket 1852, which may be integrated into a docking spar (e.g., docking spar 480) of a flexible manipulator assembly 460 or other component of a robotic medical system. More specifically, the connection mechanism 1850 includes cylindrical coupling members 1854 and 1856 extending on opposite ends of a connector body 1858 located at a medial portion of the connection mechanism 1850. A passage 1870 extends through the body 1858. An end 1874 of the connection mechanism 1850 may couple to an elongate device (e.g., elongate device 472), and a second end 1872 of the connection mechanism 1850 may couple to an endotracheal tube (e.g., endotracheal tube 311 and/or 478).

A first end portion may include the coupling members 1854 and 1856. The members 1854 and 1856 have curved (e.g., cylindrical, toroidal, partially spherical, etc.) exterior surfaces to mate with curved surfaces 1860 and 1862, respectively, of the bracket 1852, ultimately coupling to the robotic medical system. The coupling members 1854 and 1856 may be retained magnetically, and accordingly, the members 1854 and 1856 and the bracket 1852 may each include magnets and/or a material responsive to a magnetic field. In some such examples, the bracket 1852 include magnets (e.g., permanent magnets, electromagnets, hybrid magnets, etc.) proximate to the curved surfaces 1860 and 1862, while the coupling members 1854 and 1856 include magnets or a material responsive to a magnetic field (e.g., iron, nickel, cobalt, a ferritic compound, etc.), or vice-versa.

When magnetically attached, as shown in FIG. 19B, the coupling members 1854 and 1856 may rotate about the longitudinal axis A, with respect to the bracket 1852, while the body 1858 remains laterally coupled to the bracket. The amount of rotation may be limited by contact with the bracket 1852 or the bracket 1852 may permit the connection mechanism 1850 to rotate a full 360°. Accordingly, in various embodiments, the connection mechanism 1850 may rotate between about 180° and about 360°. This rotation may occur in response to slight movement of the patient or manipulator assembly 460. A tube 1880 couples the connection mechanism 1850 to a source of air and/or anesthesia. The magnetic connection allows free rotation of the connector in response to forces from the air and anesthesia tubing. With the connection mechanism 1850 attached to the endotracheal tube 478, patient movement greater than a threshold may generate a force that causes the release of the magnetic members 1854 and 1856 from the bracket 1852. Thus, the connection mechanism 1850 coupled to the endotracheal tube 478 (all attached to the patient) separates from the bracket 1852 of the docking spar 1820. The magnets of the members 1854 and 1856 may be selected to release in response to a predetermined force or motion.

Optionally, the connection mechanism 1850 and/or the bracket 1852 may include Hall sensors to detect when the connection mechanism is completely seated, partially seated, or not seated to the bracket 1852. Various control modes of the robotic medical system may be activated depending on the detected seating of the connection mechanism 1850. Optionally, the connection mechanism 1850 may include a set of fins 1864 which create a tapered body profile that provides assistance with the directional mounting (i.e., prevents upside-down mounting). As shown in FIG. 19A, the curved surface 1860 is tapered to mate with a corresponding tapered body profile of the connection mechanism 1850.

In some embodiments, the portions of the connection mechanism 1850 that couple to the air source, the elongate device, and/or the endotracheal tube rotate or permit rotation relative to the connection mechanism 1850 to make the connections more compliant and to make it easier to complete the connections. In one such example, the tube 1880 that couples to the source of air and/or anesthesia rotates and/or permits rotation of the coupled source. In one such example, the first end 1874 of the connection mechanism 1850 that couples to the elongate device and the second end 1872 of the connection mechanism 1850 that couples to the endotracheal tube rotate and/or permit rotation of the coupled device. This may also prevent the coupled devices from inadvertently causing the connection mechanism 1850 to release from the bracket 1852 or from inadvertently preventing the connection mechanism 1850 from releasing.

Further embodiments of the connection mechanism 2000 are shown in FIGS. 20A and 20B. The connection mechanism 2000 may rotatably or swively couple to a mating bracket 2001 that is integrated into a docking spar (e.g., docking spar 480) or other component of a robotic medical system. In this embodiment, the connection mechanism 2000 may rotatably or swively couple to a mating bracket 2001. More specifically, the connection mechanism 2000 includes toroidal-shaped coupling members 2004 and 2006 extending on opposite ends of a connector body 2008. A passage 2010 extends through the body 2008. An end 2014 of the connection mechanism 2000 may couple to an elongate device (e.g., elongate device 472), and a second end 2012 of the connection mechanism 2000 may couple to an endotracheal tube (e.g., endotracheal tube 311 and/or 478). A third end portion may include the coupling members 2004 and 2006. The members 2004 and 2006 mate with curved surfaces of the mating bracket 2001. The coupling members 2004 and 2006 may be retained magnetically, and accordingly, the members 2004 and 2006 and the bracket 2001 may each include magnets and/or a material responsive to a magnetic field. In some such examples, the bracket 2001 includes magnets, while the coupling members 2004 and 2006 include magnets or a material responsive to a magnetic field, or vice-versa.

When magnetically attached, the coupling members 2004 and 2006 may rotate about the longitudinal axis A, with respect to the bracket 2001 and docking spar, while the body 2008 remains laterally coupled to the bracket/docking spar. The amount of rotation may be limited by contact with the bracket 2001 or the bracket 2001 may permit the connection mechanism 2000 to rotate a full 360°. This rotation may occur in response to slight movement of the patient or manipulator assembly 460. A tube 2020 couples the connection mechanism 2000 to a source of air and/or anesthesia. The magnetic connection allows free rotation of the connection mechanism in response to forces from the air and anesthesia tubing. With the connection mechanism 2000 attached to the endotracheal tube 478, larger patient movement may generate a force that causes the release of the magnetic members 2004 and 2006 from the bracket 2001. Thus, the connection mechanism 2000 coupled to the endotracheal tube 478 separates from the bracket 2001 leaving the connection mechanism. The magnets of the members 2004 and 2006 may be selected to release in response to a predetermined force or motion but not release accidentally during minor motions associated with regular operation.

In some embodiments, the portions of the connection mechanism 2000 that couple to the air source, the elongate device, and/or the endotracheal tube rotate or permit rotation relative to the connection mechanism 2000 to make the connections more compliant and to make it easier to complete the connections. In one such example, the tube 2020 that couples to the source of air and/or anesthesia rotates and/or permits rotation of the coupled source. In one such example, the first end 2014 of the connection mechanism 2000 that couples to the elongate device and the second end 2012 of the connection mechanism 2000 that couples to the endotracheal tube rotate and/or permit rotation of the coupled device. This may also prevent the coupled devices from inadvertently causing the connection mechanism 2000 to release from the bracket 2001 or from inadvertently preventing the connection mechanism 2000 from releasing.

In this embodiment, fins 2022 are untapered and thus the body 2008 is generally symmetric to allow for easier installation. The fins 2022 do not contact the bracket 2001 during rotation of the connection mechanism 2000 with respect to the bracket. The fins 2022 may provide added structural support and strength and may improve grip when manipulating the connection mechanism. The toroidal shape of the members 2004 and 2006 may provide for easier installation as compared to the cylindrical shaped members and may allow release of the connection mechanism in multiple radial directions. Other types of 360 degree magnetic surfaces may also be suitable.

Either of the connection mechanisms 1850 and 2000 may have electromagnetic connections that may have a variable magnetic force at different stages of the procedure. For example, during installation, the magnetic force may be relatively low so that the user does not experience too great of a force as the connection mechanism approaches the docking spar. During the procedure, the magnetic force may be increased. In another example, if patient movement is detected using sensors, the magnetic force may be decreased to allow for disconnect.

Optionally, a full or partial connect of the connection mechanism may be detected using sensors. For example, if the system senses the connection mechanism is disconnected, a signal can be sent to provide an error message to the operator to prevent further actuation or insertion motor movement. For this purpose, the connection mechanism 2000 and/or the bracket 2001 may include Hall sensors to detect when the connection mechanism 2000 is completely seated, partially seated, or not seated to the bracket 2001. Optionally, the connection mechanism may include one-way seals that prevent air and anesthesia from escaping from the endotracheal tube. The seal can allow for a catheter to be inserted through the connection mechanism and the endotracheal tube but seal around the outer surface of the catheter.

Examples of a connection mechanism 2100 (e.g., connection mechanism 1850 and/or 2000) at various stages of fabrication are shown in FIGS. 21A and 21B. The connection mechanism 2100 includes a body 2102 portion and caps 2104 and 2106 that couple to the body 2102. The body 2102 is shown prior to coupling the caps 2104 and 2106 in FIG. 21A and after coupling in FIG. 21B.

Referring first to FIG. 21A, the body 2102 is received. The body 2102 includes a pair of substantially cylindrical barrel portions 2108A and 2108B on opposing sides of a medial portion 2110 along a longitudinal axis A. The barrel portions 2108A and 2108B and the medial portion 2110 each have a hollow interior such that a passage 2112 extends through the body 2102 along the longitudinal axis A. In some embodiments, an end of one of the barrel portions 2108A is configured to couple to an endotracheal tube (e.g., endotracheal tube 311 and/or 478), while an end of the other barrel portion 2108B is configured to couple to an elongate device (e.g., elongate device 202, 310, 472, and/or 1600) such that the elongate device may extend longitudinally through the passage 2112. To this end, the barrel portions 2108A and 2108B may have different configurations (e.g., exterior diameter, passage diameter, exterior taper, passage taper, barbs, etc.) or may be symmetrical.

The exterior of the barrel portions 2108A and 2108B may include a retaining feature 2114 configured to retain the caps 2104 and 2106. For example, in an embodiment, the barrel portions 2108A and 2108B and the caps 2104 and 2106 are threaded for screw-on coupling. In some embodiments, the barrel portions 2108A and 2108B and/or the caps 2104 and 2106 include barbs for snap-fit coupling. In some embodiments, the barrel portions 2108A and 2108B and/or the caps 2104 and 2106 are tapered for coupling. In some embodiments, the barrel portions 2108A and 2108B and/or the caps 2104 and 2106 include clips or are configured to receive a clip for coupling.

To accommodate the barrel portions 2108A and 2108B, the medial portion 2110 may have a varying profile along the cylindrical axis (e.g., different exterior diameter, different passage diameter, exterior surface taper, passage taper, etc.) or may have a substantially uniform profile throughout. In some embodiments, the medial portion 2110 includes fins on the exterior surface for strength and/or grip. The fins may extend along the longitudinal axis A and/or perpendicular thereto. In further embodiments, the exterior of the medial portion 2110 is textured in addition to or instead of the fins.

The body 2102 may include a tube 2116 extending from the medial portion 2110 perpendicular to or at an angle to the longitudinal axis A. The tube 2116 may have a hollow interior that extends to the passage 2112 through the barrel portions 2108A and 2108B. The tube 2116 couples connection mechanism 2100 to a source of air and/or anesthesia and the hollow interior allows the flow of gas to and from the passage 2112. To control coupling depth, the tube 2116 may include an exterior flange 2118. In some embodiments, fins of the medial portion 2110 extend from the exterior flange 2118.

With respect to the caps 2104 and 2106, each may include a coupling member 2120 having a hollow cylindrical structure configured to enclose at least a portion of a corresponding barrel portion 2108. The coupling members 2120 of the caps 2104 and 2106 may rotatably or swively (e.g., rotateable about the longitudinal axis A) couple to a mating bracket, which may be integrated into a docking spar. Accordingly, the coupling members 2120 may be configured to magnetically couple to the mating bracket and may include a material responsive to a magnetic field (e.g., iron, nickel, cobalt, a ferritic compound, etc.) and/or a magnetic material. In some examples, this material is mixed with an elastic material (e.g., a plastic) to produce a magnetic plastic material. The magnetic connection allows free rotation of the connection mechanism 2100 in response to forces from the air and anesthesia tubing. With the connection mechanism 2100 attached to the endotracheal tube, larger patient movement may generate a force that causes the release of the coupling members 2120 from the bracket. The magnetic response of the coupling members 2120 may be selected to release in response to a predetermined force or motion.

The exterior of the coupling members 2120 may vary along the longitudinal axis A such that the profile provides assistance with the directional mounting. For example, the exterior diameter of one of the coupling members 2120 may be different from the other coupling member 2120 to mate with the corresponding bracket in a single orientation. The exterior surface of the coupling members 2120 may be toroidal, cylindrical, spherical, or partially spherical. Other types of 360 degree magnetic surfaces may also be suitable.

Referring to FIG. 21B, the caps 2104 and 2106 containing the coupling members 2120 are coupled to the barrel portions 2108A and 2108B using any suitable technique. For example, the caps 2104 and 2106 may be coupled to the barrel portions 2108A and 2108B of the body 2102 by screwing, snapping, and/or gluing the caps 2104 and 2106. In some embodiments, the caps 2104 and 2106 are coupled to the respective barrel portions 2108A and 2108B by clips. In some embodiments, the caps 2104 and 2106 are coupled to the respective barrel portions 2108A and 2108B by press fitting, ultrasonic welding, heat staking, and/or square-pin/round-hole fitment.

Examples of a connection mechanism 2200 (e.g., connection mechanism 1850 and/or 2000) at various stages of fabrication via an over-molding process are shown in FIGS. 22A and 22B. Referring to FIG. 22A, a pair of rings 2202 that will become part of coupling members are received. Similar to the coupling member above, the coupling members may be configured to magnetically couple to a mating bracket, and the rings 2202 may include a material responsive to a magnetic field and/or a magnetic material. In some examples, this material is mixed with a plastic to produce a magnetic plastic material. The rings 2202 may be complete cylinders or slotted cylinders to accommodate the flow of a moldable material. The exterior surfaces of the rings 2202 may vary along a cylindrical axis such that the profile provides assistance with the directional mounting. For example, the exterior diameter of one of the rings 2202 may be different from the other ring 2202 to mate with a corresponding bracket in a single orientation.

Referring to FIG. 22B, a flowable material of the connection mechanism 2200 (e.g., a plastic material) is molded over the rings 2202 in an over-molding process to form the connection mechanism 2200. The flowable material may encapsulate the rings 2202 to form coupling members 2204A and 2204B. In some embodiments, the flowable material covers the exterior surface of the rings 2202 so that the flowable material forms the exterior of the coupling members 2204. This may avoid open seams on the exterior surfaces. In some embodiments, the flowable material is controlled to expose the exterior surface of the rings 2202 so that the rings 2202 form the exterior surface of the coupling members 2204. This may promote better coupling with the mating bracket and may allow electrical as well as physical coupling between the connection mechanism 2200 and the bracket.

The remaining elements of the connection mechanism 2200 may be substantially as described above. For example, the hollow coupling members 2204 may extend along a longitudinal axis such that a passage 2206 extends through the connection mechanism 2200. The connection mechanism 2200 may include a tube 2208 extending perpendicular to or at an angle to the longitudinal axis. The tube 2208 may have a hollow interior that extends to the passage 2206. The tube couples connection mechanism 2200 to a source of air and/or anesthesia and the hollow interior allows the flow of gas to and from the passage 2206. To control coupling depth, the tube 2208 may include an exterior flange 2210.

The use of an over-molding process to form the connection mechanism 2200 produces a distinct structure that is free of seams between the coupling members 2204 and the remainder of the connection mechanism 2200, unlike embodiments where the coupling members 2204 are attached as caps. This may eliminate a potential point of failure and/or leakage at the cap seam. Over-molding may also be more cost effective than other methods of fabricating the connection mechanism.

Examples of a connection mechanism 2300 (e.g., connection mechanism 1850 and/or 2000) at various stages of fabrication via a multiple shot molding process are shown in FIGS. 23A and 23B. Referring to FIG. 23A, a body 2302 portion of the connection mechanism 2300 is formed in a first process, such as a first molding process. The body 2302 may be substantially as described above and may include a pair of substantially cylindrical barrel portions 2304A and 2304B on opposing sides of a medial portion 2306 along a longitudinal axis A. The barrel portions 2304A and 2304B and the medial portion 2306 each have a hollow interior such that a passage 2308 extends through the body 2302 along the longitudinal axis A. The barrel portions 2304A and 2304B may have different configurations (e.g., exterior diameter, passage diameter, exterior taper, passage taper, barbs, etc.) or may be symmetrical. In some examples, the exterior surfaces of the barrel portions 2304A and 2304B are configured to promote bonding and/or flow during subsequent molding processes by including fins and/or texture.

The body 2302 may include a tube 2310 extending from the medial portion 2306 perpendicular to or at an angle to the longitudinal axis A. The tube 2310 may have a hollow interior that extends to the passage 2308 through the barrel portions 2304A and 2304B. The tube couples connection mechanism 2300 to a source of air and/or anesthesia and the hollow interior allows the flow of gas to and from the passage 2308. To control coupling depth, the tube 2310 may include an exterior flange 2312.

Referring to FIG. 23B, a subsequent process, such as a subsequent molding process, forms coupling members 2314 on the barrel portions 2304A and 2304B. The coupling members 2314 may rotatably or swivelly couple to a mating bracket. Accordingly, the coupling members 2314 may be configured to magnetically couple to the mating bracket and may include a material responsive to a magnetic field and/or a magnetic material. In some examples, this material is mixed with an elastic material (e.g., a plastic) to produce a magnetic plastic material. The magnetic response of the coupling members 2314 may be selected to release in response to a predetermined force or motion.

The exterior of the coupling members 2314 may vary along the longitudinal axis A such that the profile provides assistance with the directional mounting. For example, the exterior diameter of one of the coupling members 2314 may be different from the other coupling member 2314 to mate with the corresponding bracket in a single orientation. The exterior surface of the coupling members 2314 may be toroidal, cylindrical, spherical, or partially spherical. Other types of 360 degree magnetic surfaces may also be suitable.

Multiple shot molding produces a distinct structure that is free of seams between the coupling members 2314 and the remainder of the connection mechanism 2300. This may eliminate a potential point of failure and/or leakage at the cap seam. Multiple shot molding may also be more cost effective than other methods of fabricating the connection mechanism.

Further examples of the connection mechanism 2400 are shown in FIGS. 24A and 24B. The connection mechanism 2400 includes a body 2402 portion and a shell 2404 that couples to the body 2402. The body 2402 and the shell 2404 are shown in an uncoupled configuration in FIG. 24A and in a coupled configuration in FIG. 24B.

With respect to the body 2402, this portion of the connection mechanism 2400 includes a pair of substantially cylindrical barrel portions 2406A and 2406B on opposing sides of a medial portion 2408 along a longitudinal axis A. The barrel portions 2406A and 2406B and the medial portion 2408 each have a hollow interior such that a passage 2410 extends through the body 2402 along the longitudinal axis A. In some embodiments, an end of one of the barrel portions 2406A is configured to couple to an endotracheal tube (e.g., endotracheal tube 311 and/or 478), while an end of the other barrel portion 2406B is configured to couple to an elongate device (e.g., elongate device 202, 310, 472, and/or 1600) such that the elongate device may extend longitudinally through the passage 2410. To this end, the barrel portions 2406 may have different configurations (e.g., exterior diameter, passage diameter, exterior taper, passage taper, barbs, etc.) or may be symmetrical.

To accommodate the barrel portions 2406, the medial portion 2408 may have a varying profile along the cylindrical axis (e.g., different exterior diameter, different passage diameter, exterior surface taper, passage taper, etc.) or may have a substantially uniform profile throughout. In some embodiments, the medial portion 2408 includes fins on the exterior surface for strength and/or grip. The fins may extend along the longitudinal axis A and/or perpendicular thereto. In further embodiments, the exterior of the medial portion 2408 is textured in addition to or instead of the fins.

The body 2402 may include a tube 2412 extending from the medial portion 2408 perpendicular to or at an angle to the longitudinal axis A. The tube 2412 may have a hollow interior that extends to the passage 2410 through the barrel portions 2406. The tube couples connection mechanism 2400 to a source of air and/or anesthesia and the hollow interior allows the flow of gas to and from the passage 2410. To control coupling depth, the tube 2412 may include an exterior flange 2414. In some embodiments, fins of the medial portion 2408 extend from the exterior flange 2414.

Turning next to the shell 2404, this portion of the connection mechanism 2400 includes a pair of coupling members 2416 disposed on opposite sides of a medial portion 2418. The coupling members 2416 may include hollow cylindrical portions and/or horizontal cylindrical segments (e.g., rings) configured to couple to the barrel portions 2406 of the body 2402. In one such embodiment, a first coupling member 2416 includes a cylindrical portion and a horizontal cylindrical segment configured to enclose more than half of a first barrel portion 2406, while the second coupling member 2416 includes a horizontal cylindrical segment configured to enclose more than half of a second barrel portion 2406. In this way, the coupling members 2416 couple to the barrel portions 2406 to secure the shell 2404 to the body 2402. The material of the shell 2404 may be elastically deformable to expand while coupling and to contract when coupled. In some such embodiments, the inner surface of a coupling member in the relaxed state has substantially the same radius as an outer surface of a barrel portion to which it couples. In some embodiments, the shell 2404 includes a tab 2420 extending from one or both of the coupling members 2416 to assist in applying coupling and/or uncoupling force.

The medial portion 2418 of the shell 2404 may or may not contact the medial portion 2408 of the body 2402. Accordingly, in some embodiments, the medial portion 2418 of the shell 2404 includes a horizontal cylindrical segment configured to enclose more than half of the medial portion 2408 of the body 2402 to couple and secure the shell 2404 to the body 2402. In further embodiments, the medial portion 2418 of the shell 2404 does not enclose the body 2402.

The coupling members 2416 of the shell 2404 may rotatably or swivelly (e.g., rotateable about the longitudinal axis A) couple to a mating bracket, which may be integrated into a docking spar. In some such embodiments, the coupling members 2416 are configured to magnetically couple to the mating bracket and may include a material responsive to a magnetic field and/or a magnetic material. In some examples, this material is mixed with an elastic material to aid in coupling to the body 2402.

The magnetic connection allows free rotation of the connection mechanism 2400 in response to forces from the air and anesthesia tubing. With the connection mechanism 2400 attached to the endotracheal tube, larger patient movement may generate a force that causes the release of the coupling members 2416 from the bracket. Thus, the connection mechanism 2400 coupled to the endotracheal tube separates from the bracket of the docking spar, leaving the connection mechanism 2400 and endotracheal tube fixed to the patient. The magnetic response of the coupling members 2416 may be selected to release in response to a predetermined force or motion.

Optionally, the connection mechanism 2400 may include Hall sensors to detect when the connection mechanism is completely seated, partially seated, or not seated to the bracket. Various control modes of the robotic medical system may be activated depending on the detected seating of the connection mechanism 2400. The exterior of the connection mechanism shell 2404 may vary along the longitudinal axis A such that the profile provides assistance with the directional mounting. For example, the exterior diameter of one of the coupling members 2416 may be different from the other coupling member 2416 to mate with the corresponding bracket in a single orientation. The exterior surface of the coupling members 2416 may be toroidal, cylindrical, spherical, or partially spherical. Other types of 360 degree magnetic surfaces may also be suitable.

The two-part connection mechanism 2400 may simplify fabrication, reduce cost, and promote reuse. For example, as the body 2402 and the shell 2404 may include different materials, in some embodiments, it is more direct to assemble and/or lower cost to manufacture them as two separate pieces. In some embodiments, at least the shell 2404 may be reused. Particularly in examples where the shell 2404 is more expensive to manufacture than the body 2402, cost savings by reusing the shell 2404 may justify a cost increase associated with manufacturing two pieces.

FIGS. 25A and 25B illustrate a bracket 2500 for mating to a connection mechanism 2502, such as any of those above (e.g., connection mechanism 1850, 2000, 2100, 2200, 2300, and/or 2400). Specifically, FIG. 25A illustrates the mating bracket 2500 and the connection mechanism 2502 in an uncoupled configuration, and FIG. 25B illustrates the mating bracket 2500 and the connection mechanism 2502 in a coupled and locked configuration. The mating bracket 2500 may be coupled to a portion of a robotic medical system, such as the docking spar of a manipulator assembly, and may couple the connection mechanism 2502 to the system.

The mating bracket 2500 may include a mating surface 2504 for interfacing with the connection mechanism 2502 and a magnetic or magneto-reactive retaining element 2506 for retaining the connection mechanism 2502 against the mating surface 2504. In some examples, the mating bracket 2500 retains the connection mechanism 2502 by magnetically coupling to coupling members of the connection mechanism 2502, and accordingly, the retaining element 2506 produces a magnetic field to couple to the connection mechanism 2502 and/or includes a material that reacts with a magnetic field to couple with magnets in the connection mechanism 2502. In various such examples, the retaining element 2506 may include one or more permanent magnets, electromagnets, and/or hybrid magnets that combine a permanent magnet and an electromagnet.

The retaining element 2506 may be fixed or may be movable relative to the mating surface 2504. In some embodiments, the retaining element 2506 is movable to change the amount of coupling force between the mating bracket 2500 and the connection mechanism 2502. In one such embodiment, the retaining element 2506 is coupled to a mechanical actuator (e.g., a lever) 2508 that moves the retaining element 2506 closer to the mating surface 2504 to increase the magnetic coupling force and further from the mating surface 2504 to decrease the magnetic coupling force. In particular, the retaining element 2506 may be relatively further from the mating surface 2504 while the connection mechanism 2502 is being connected or disconnected, as shown in FIG. 25A, to reduce the tendency of the connection mechanism 2502 to snap towards and impact the mating surface 2504 and to make disconnecting easier. Once the connection mechanism 2502 contacts the mating surface 2504, the retaining element 2506 may be moved closer to the mating surface 2504 to increase the coupling force as shown in the locked configuration of FIG. 25B. In examples where the retaining element 2506 includes an electromagnet, the mechanical actuator 2508 may also affect the power supplied to the electromagnet to decrease the coupling force in the unlocked configuration while the connection mechanism 2502 is being connected or disconnected and to increase the power supplied in the locked configuration. In examples where the retaining element 2506 includes a hybrid magnet, the electromagnetic portion of the hybrid magnet may be powered to enhance or accelerate the release of the connection mechanism by providing a neutralizing or repulsive force.

In some examples, the mating bracket 2500 includes a sensor 2510 to sense when the connection mechanism 2502 is proximate to or contacting the mating surface 2504. In one such embodiment, the sensor 2510 includes a Hall sensor to detect a change in a magnetic field when the connection mechanism 2502 is completely seated, partially seated, or not seated to the mating bracket 2500. The sensor 2510 may be coupled to the mechanical actuator 2508 and the retaining element 2506 to move in tandem with the retaining element 2506. That is, the sensor 2510 may be moved relatively further from the mating surface 2504 while the connection mechanism 2502 is being connected or disconnected in the unlocked configuration. Once the connection mechanism 2502 contacts the mating surface 2504, the sensor 2510 may be moved closer to the mating surface 2504 in the locked configuration.

FIG. 26 illustrates a bracket 2600 for mating to a connection mechanism 2602, such as any of those above, with electronic control of the coupling force. The mating bracket 2600 may be coupled to a portion of a robotic medical system, such as the docking spar of a manipulator assembly, and may couple the connection mechanism 2602 to the system.

The mating bracket 2600 may be similar to those described above in many aspects. For example, it may include a mating surface 2604 for interfacing with the connection mechanism 2602 and a magnetic or magnetoreactive retaining element 2606 for retaining the connection mechanism 2602 against the mating surface 2604. In some examples, the mating bracket 2600 retains the connection mechanism 2602 by magnetically coupling to coupling members of the connection mechanism 2602, and the retaining element 2606 produces a magnetic field to couple to the connection mechanism 2602 and/or includes a material that reacts with a magnetic field to couple with magnets in the connection mechanism 2602. In various such examples, the retaining element 2606 may include one or more permanent magnets, electromagnets, and/or hybrid magnets.

The mating bracket 2600 may include a control mechanism 2608 for controlling the amount of coupling force between the mating bracket 2600 and the connection mechanism 2602. In some embodiments, the retaining element 2606 includes an electromagnet and the control mechanism 2608 includes a switch, shunt, variable resistor, and/or other power control element to control voltage and/or current through the electromagnet and thereby adjust the coupling force. The control mechanism may maintain a relatively low amount of force while connecting or disconnecting the connection mechanism 2602 to reduce the tendency of the connection mechanism 2602 to snap towards the mating surface 2604. In an example with a hybrid magnet, the low amount of force may be provided by the permanent magnet. Once the connection mechanism 2602 contacts the mating surface 2604, the control mechanism may increase the amount of coupling force provided by the retaining element 2606 to secure the connection mechanism 2602 by increasing the power supplied to an electromagnet of the retaining element 2606. In some embodiments, the control mechanism 2608 includes a solenoid, linear actuator, or other electromechanical actuator to control the distance between the retaining element 2606 and the mating surface 2604 and thereby adjust the coupling force substantially as described above.

The mating bracket 2600 may also include a sensor 2610 coupled to the control mechanism 2608 to sense when the connection mechanism 2602 is proximate to or contacting the mating surface 2604 and to instruct the control mechanism 2608 to adjust the coupling force accordingly. In an embodiment, the control mechanism 2608 increases the coupling force provided by the retaining element 2606 when the sensor 2610 indicates that the connection mechanism 2602 is proximate to or contacting the mating surface 2604 and decreases the coupling force provided by the retaining element 2606 when the sensor 2610 indicates that the connection mechanism 2602 is not proximate to or contacting the mating surface 2604. The sensor 2610 may include a Hall sensor to detect a change in a magnetic field when the connection mechanism 2602 is completely seated, partially seated, or not seated to the mating bracket 2600. Other suitable sensors 2610 include pressure sensors, contact sensors, and other suitable sensing mechanisms.

FIG. 27 illustrates a method 2700 according to an embodiment of the present disclosure. The method 2700 includes a workflow for installing a connection mechanism (e.g., connection mechanism 1850, 2000, 2100, 2200, 2300, 2400, 2502 and/or 2602). The method 2700 is illustrated in FIG. 27 as a set of operations or processes 2705 through 2740. Not all of the illustrated processes 2705 through 2740 may be performed in all embodiments of method 2700. Additionally, one or more processes that are not expressly illustrated in FIG. 27 may be included before, after, in between, or as part of the processes 2705 through 2740. In some embodiments, one or more of the processes 2705 through 2740 may be implemented, at least in part, in the form of executable code stored on non-transitory, tangible, machine-readable media that when run by one or more processors (e.g., the processors of control system) may cause the one or more processors to perform one or more of the processes. The method 2700 starts at a process 2705. At a process 2710, air and anesthesia tubes may be attached to the connection mechanism. At a process 2715, an endotracheal tube (e.g., endotracheal tube 311 and/or 478) may be placed in the patient anatomy. At a process 2720, the connection mechanism may be attached to the endotracheal tube. At a process 2725, a portion of a manipulator assembly (e.g., cart 462 of manipulator 460) may be positioned in proximity to the patient. The portion of the manipulator assembly may include a bracket (e.g., mounting bracket 1852 on docking spar 480 and/or bracket 2001, 2500, and/or 2600). At a process 2730, the connection mechanism may be connected to the bracket. At a process 2735, an elongate device (e.g., elongate device 202, 310, 472, and/or 1600) is fed through the connection mechanism and through the endotracheal tube. The method 2700 may end at a process 2740.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An apparatus for movably coupling a robotic medical system to an anatomic orifice device, the apparatus comprising:
   a first end portion configured to be connected to the robotic medical system, wherein the first end portion is configured to be disconnected from the robotic medical system when a parameter associated with motion of the anatomic orifice device relative to the robotic medical system is greater than a threshold parameter;

a second end portion configured to be connected to the anatomic orifice device, the anatomic orifice device being fixedly coupled to a patient; and a medial portion between the first end portion and the second end portion, the medial portion being configured to accommodate motion between the robotic medical system and the anatomic orifice device in at least one degree of freedom.

2. The apparatus of claim 1, wherein the medial portion is configured to accommodate motion in multiple degrees of freedom.

3. The apparatus of claim 1, wherein when the parameter associated with motion of the anatomic orifice device relative to the robotic medical system is less than the threshold parameter, the medial portion accommodates motion between the robotic medical system and the anatomic orifice device.

4. The apparatus of claim 1, wherein the medial portion includes a bellowed tube configured to contract and expand to accommodate the motion in the at least one degree of freedom.

5. The apparatus of claim 1, wherein the medial portion includes a rolling diaphragm configured to provide flexibility in the at least one degree of freedom.

6. The apparatus of claim 1, wherein:

the medial portion includes multiple linkage sets, each linkage set including a first link connected to the first end portion by a first hinge, and a second link connected to the second end portion by a second hinge, and the first and second links are connected by a parallelogram linkage.

7. The apparatus of claim 6, wherein the medial portion includes at least three linkage sets.

8. The apparatus of claim 6, wherein at least one of the first and second hinges includes a living hinge.

9. The apparatus of claim 1, further comprising a sensing mechanism including a processor, the processor configured to determine when the parameter associated with motion of the anatomic orifice device relative to the robotic medical system is greater than the threshold parameter.

10. The apparatus of claim 9, wherein the processor is further configured to actuate a decoupling mechanism to disconnect the first end portion from the robotic medical system.

11. An apparatus for movably coupling a robotic medical system to an anatomic orifice device, the apparatus comprising:

a medical system interface coupled to the robotic medical system;

a first end portion configured to be connected to the robotic medical system, the first end portion being movably connected to the medical system interface at a first joint;

a second end portion configured to be connected to the anatomic orifice device, the anatomic orifice device being fixedly coupled to a patient; and a medial portion between the first end portion and the second end portion, the medial portion being configured to accommodate motion between the robotic medical system and the anatomic orifice device in at least one degree of freedom.

12. The apparatus of claim 11, wherein the medial portion includes a first tubular portion connected to a second tubular portion, wherein the second tubular portion is configured to slideably receive the first tubular portion in a telescopic configuration.

13. The apparatus of claim 12, wherein the first tubular portion is configured to decouple from the second tubular portion.

14. The apparatus of claim 11, wherein the first end portion is configured to decouple from the medical system interface at the first joint.

15. The apparatus of claim 11, wherein the second end portion is movably connected to the anatomic orifice device at a second joint.

16. An apparatus for movably coupling a robotic medical system to an anatomic orifice device, the apparatus comprising:

a first end portion configured to be connected to the robotic medical system, the first end portion comprising a coupling member with a curved exterior surface configured to rotatably connect the first end portion to the robotic medical system;

a second end portion configured to be connected to the anatomic orifice device, the anatomic orifice device being fixedly coupled to a patient; and a medial portion between the first end portion and the second end portion, the medial portion being configured to accommodate motion between the robotic medical system and the anatomic orifice device in at least one degree of freedom.

17. The apparatus of claim 16, wherein the coupling member includes a magnetic material or a material responsive to a magnetic field.

* * * * *